(12) United States Patent
Yu et al.

(10) Patent No.: US 11,975,034 B2
(45) Date of Patent: May 7, 2024

(54) PROBIOTIC COMPOSITIONS FOR TREATING AND PREVENTING COLORECTAL CANCER

(71) Applicant: The Chinese University of Hong Kong, Shatin (CN)

(72) Inventors: Jun Yu, Ma On Shan (CN); Ka Kei Wu, Tai Po (CN); Qing Li, Shatin (CN)

(73) Assignee: The Chinese University of Hong Kong, Hong Kong SAR (CN)

( * ) Notice: Subject to any disclaimer, the term of this patent is extended or adjusted under 35 U.S.C. 154(b) by 0 days.

(21) Appl. No.: 17/881,498

(22) Filed: Aug. 4, 2022

(65) Prior Publication Data

US 2023/0158086 A1    May 25, 2023

Related U.S. Application Data

(60) Provisional application No. 63/229,933, filed on Aug. 5, 2021.

(51) Int. Cl.
*A61K 35/744* (2015.01)
*A61K 35/74* (2015.01)
*A61P 35/00* (2006.01)

(52) U.S. Cl.
CPC ............ *A61K 35/744* (2013.01); *A61K 35/74* (2013.01); *A61P 35/00* (2018.01)

(58) Field of Classification Search
CPC .... A61K 35/744; A61K 35/74; A61K 31/405; A61K 35/747; A61P 35/00; A61P 1/00
See application file for complete search history.

(56) References Cited

FOREIGN PATENT DOCUMENTS

| CA | 3104023 A1 | * | 11/2019 | .......... A23C 9/1234 |
| JP | 2020164493 A | * | 10/2020 | |

OTHER PUBLICATIONS

Roquette, Modern Formulation Solutions for Advanced Probiotic Supplements, Oct. 29, 2019 (Year: 2019).*
Dai, Zhenwei, et al. "Multi-cohort analysis of colorectal cancer metagenome identified altered bacteria across populations and universal bacterial markers." Microbiome 6.1 (2018): 1-12 (Year: 2018).*
Sugimura, Naoki. Lactobacillus gallinarum Protects against Colorectal Tumorigenesis through Secretion of Anti-tumor Metabolites. Diss. The Chinese University of Hong Kong (Hong Kong), 2020 (Year: 2020).*

* cited by examiner

*Primary Examiner* — Louise W Humphrey
*Assistant Examiner* — Mary A Crum
(74) *Attorney, Agent, or Firm* — Kilpatrick Townsend & Stockton LLP

(57) ABSTRACT

The present invention provides for compositions and methods for treating colorectal cancer or for reducing the risk of developing the disease in an individual. More specifically, compositions comprising an effective amount of beneficial bacteria such as *Lactobacillus gallinarum*, *Lactococcus lactis*, and *Carnobacterium maltaromaticum* are provided for the purpose of treating colorectal cancer in a person or for the purpose of reducing a person's risk of later developing colorectal cancer. Corresponding kits and methods are also provided.

13 Claims, 35 Drawing Sheets

Specification includes a Sequence Listing.

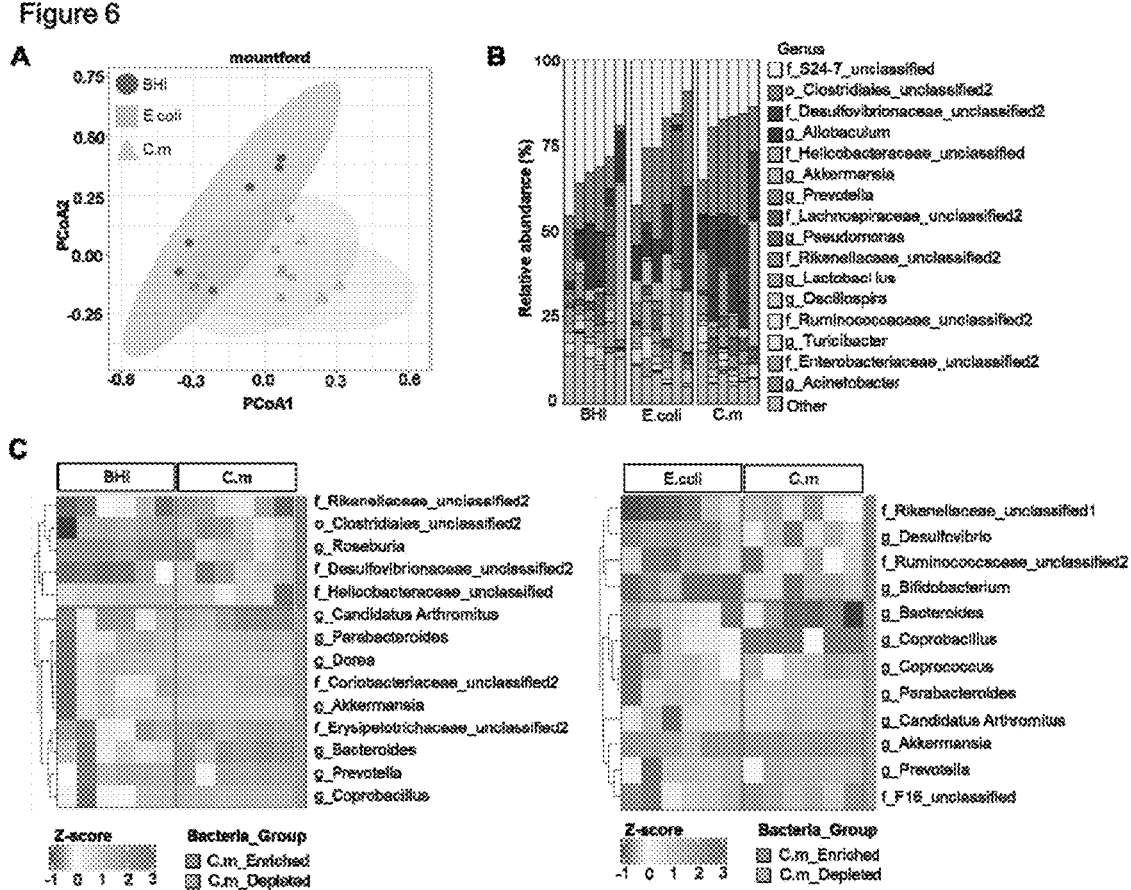

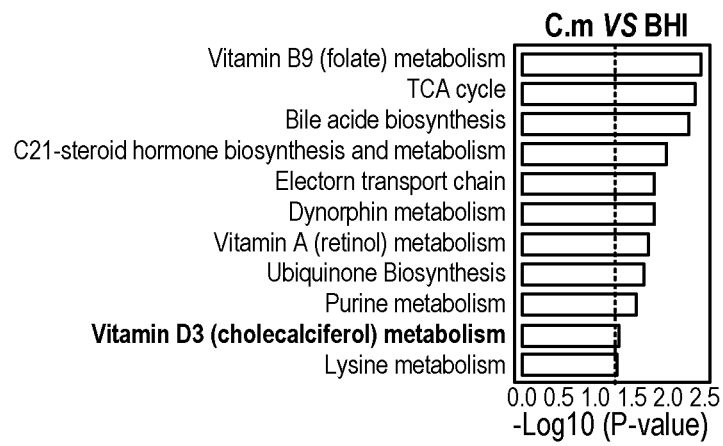
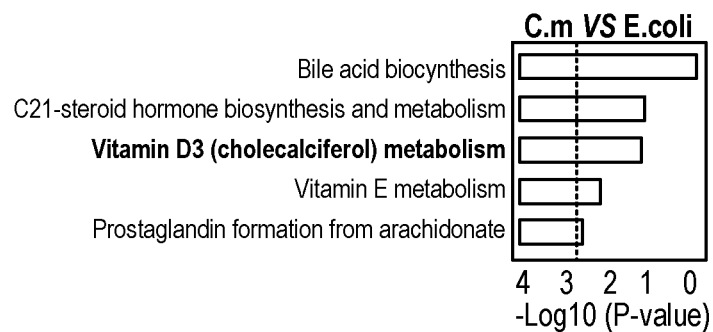
FIG. 7C

Figure 17
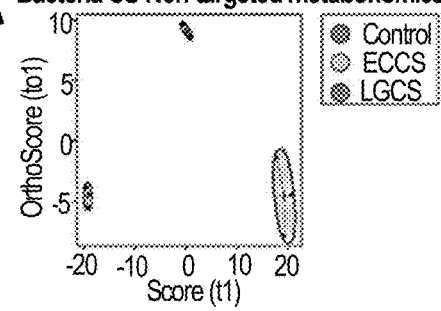
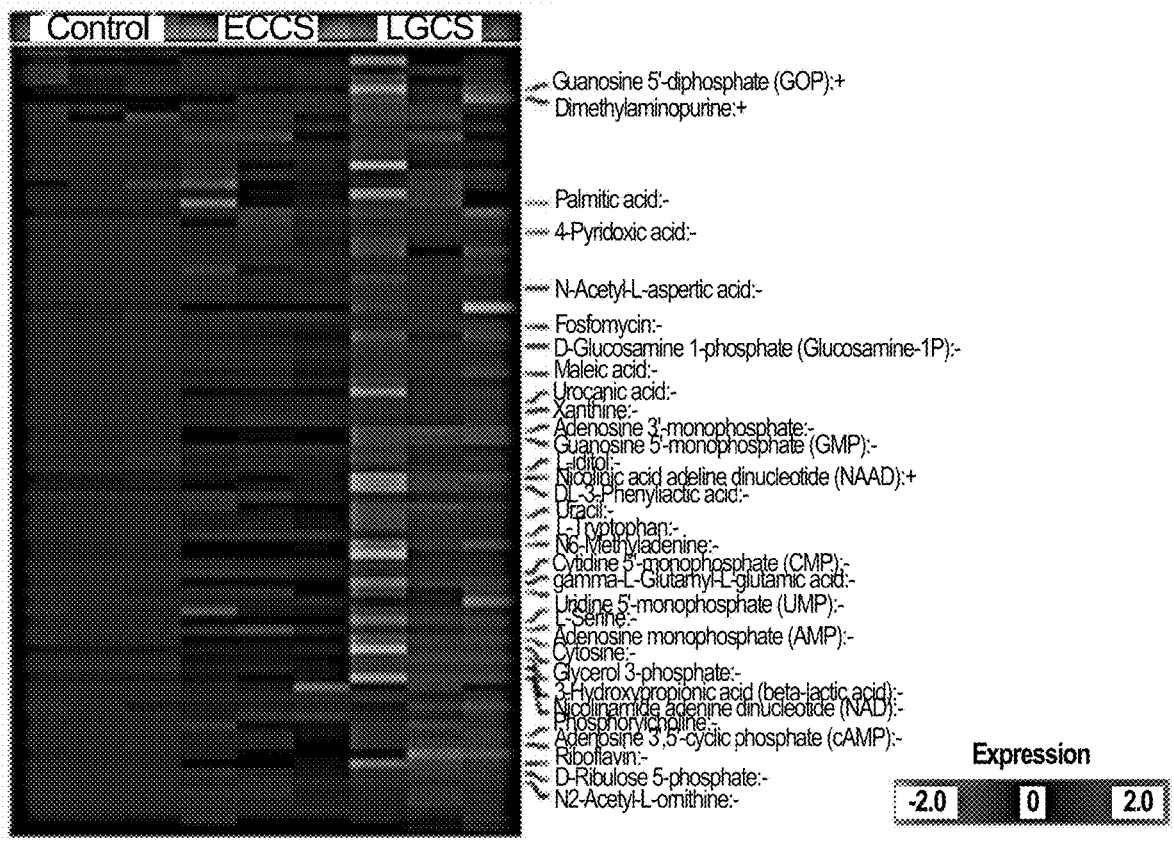
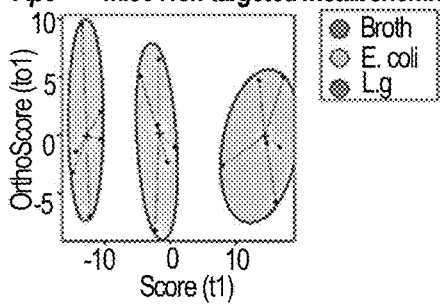

Figure 17 (cont.)
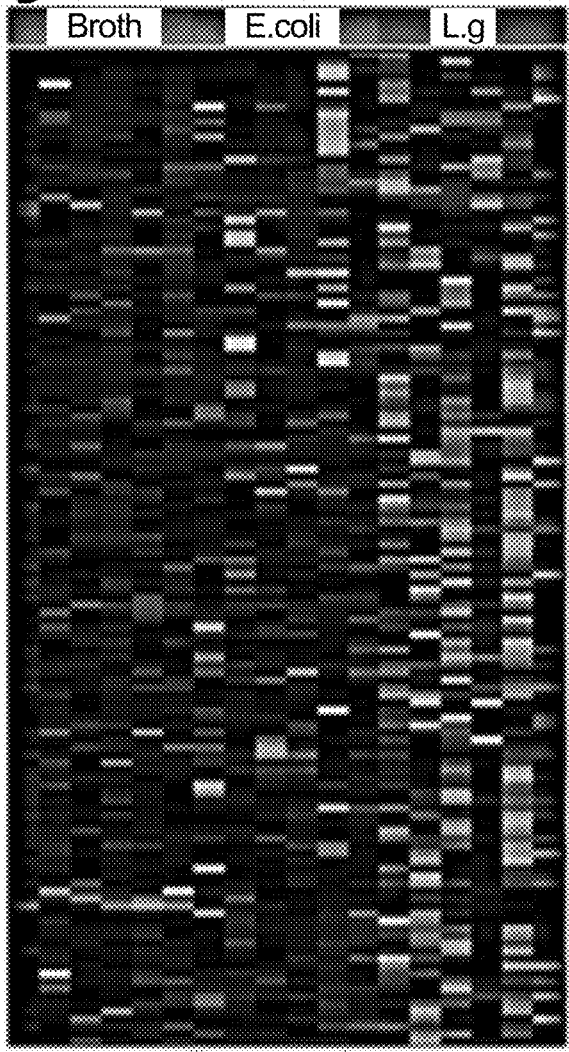
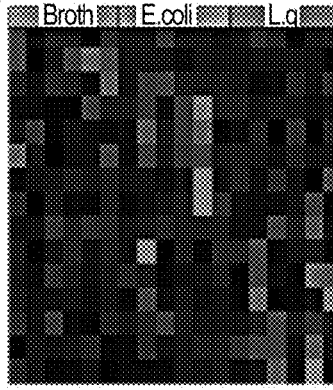

Figure 18 (cont.)
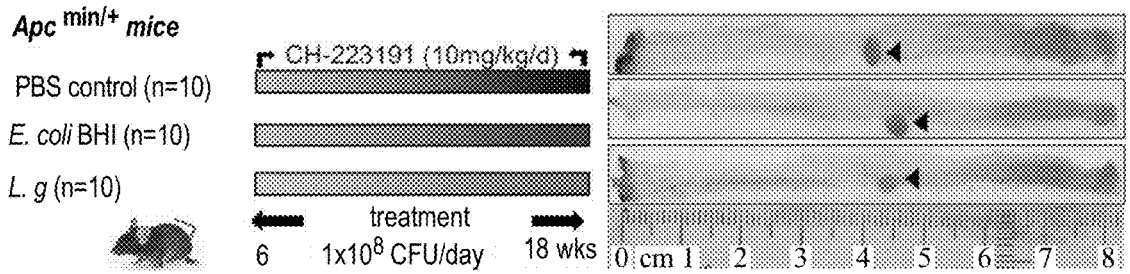
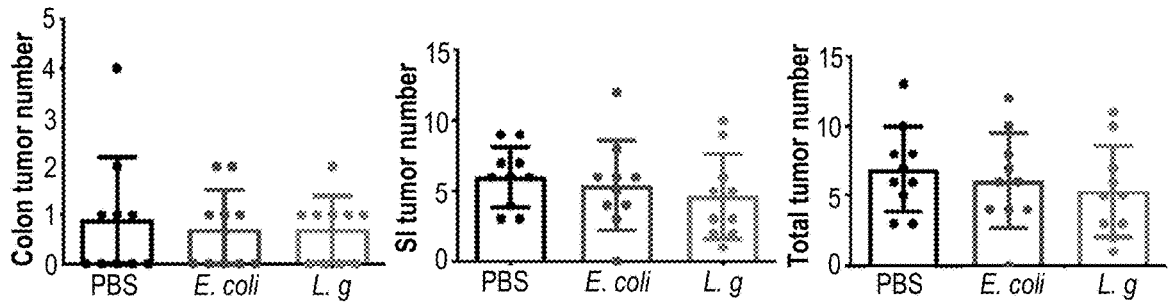
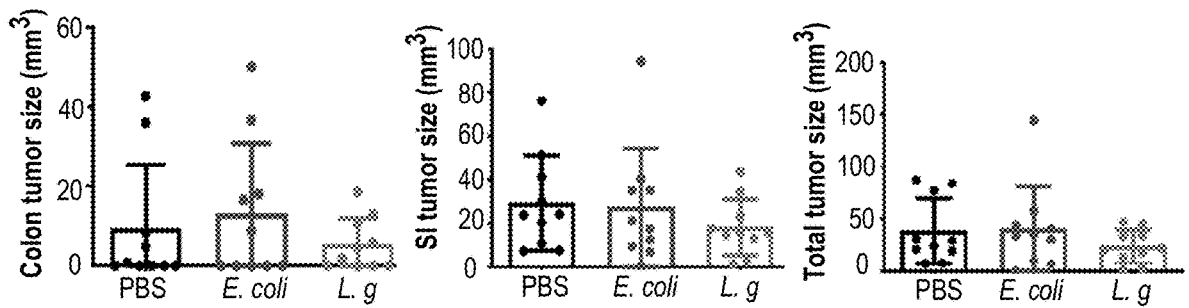
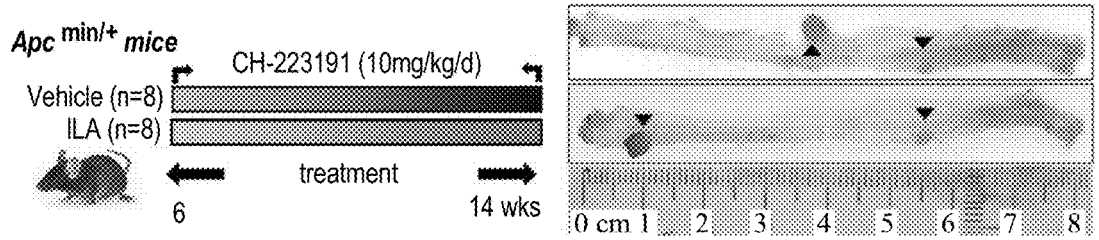

Figure 18 (cont.)
Q
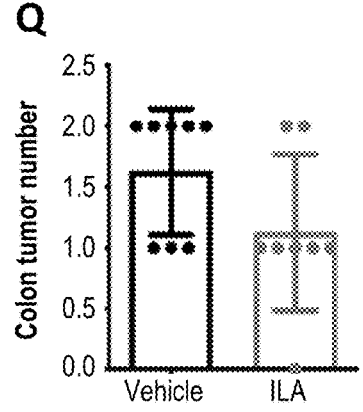
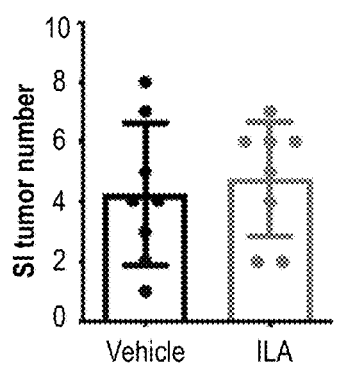
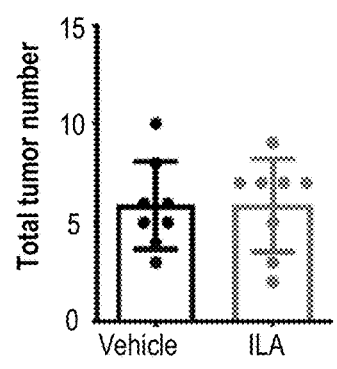
R
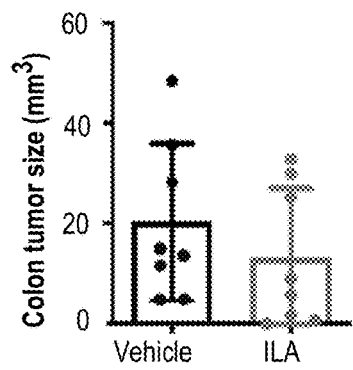
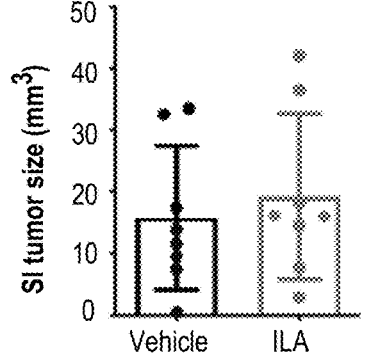
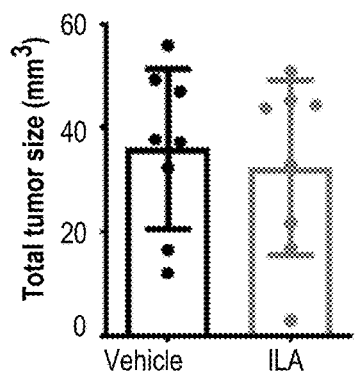

Figure 23 (cont.)
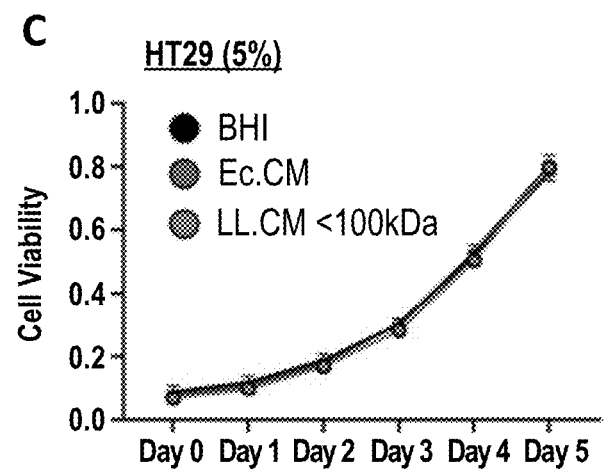
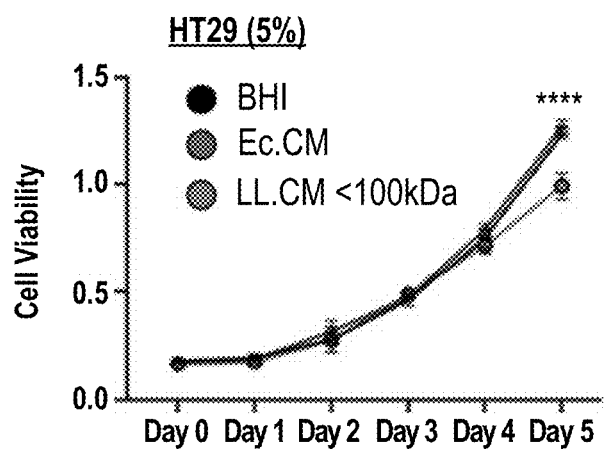

SEQUENCE LISTING

```
Sequence total quantity: 2
SEQ ID NO: 1              moltype = DNA  length = 17
FEATURE                   Location/Qualifiers
misc_feature              1..17
                          note = University primer 341F targeting 16S rRNA genes
                          V3-V4 hypervariable regions
source                    1..17
                          mol_type = other DNA
                          organism = synthetic construct
SEQUENCE: 1
cctayggrb gcascag                                                        17

SEQ ID NO: 2              moltype = DNA  length = 20
FEATURE                   Location/Qualifiers
misc_feature              1..20
                          note = University primer 806R targeting 16S rRNA genes
                          V3-V4 hypervariable regions
variation                 8..9
                          note = n = a, t, c or g
source                    1..20
                          mol_type = other DNA
                          organism = synthetic construct
SEQUENCE: 2
ggactacnng ggtatctaat                                                    20
```

PROBIOTIC COMPOSITIONS FOR TREATING AND PREVENTING COLORECTAL CANCER

RELATED APPLICATIONS

This application claims priority to U.S. Provisional Patent Application No. 63/229,933, filed Aug. 5, 2021, the contents of which are hereby incorporated by reference in the entirety for all purposes.

REFERENCE TO SEQUENCE LISTING

The present application is being filed along with a Sequence Listing in electronic format. The Sequence Listing file, entitled, "80015-1342522-033510US_ST26.xml", was created on Feb. 11, 2023 and is 4,194 bytes in size. The information in electronic format of the Sequence Listing is incorporated herein by reference in its entirety.

BACKGROUND OF THE INVENTION

Colorectal cancer (CRC) is the third most common cancer and the third leading cause of cancer mortality worldwide, with an estimated incidence of 1 million new cases and a mortality of >500 000 deaths per year. Several intrinsic (e.g., age, male gender, ethnicity, diabetes mellitus, obesity and inflammatory bowel disease) and extrinsic (e.g., cigarette smoking, inadequate intake of fiber, high consumption of alcohol, red meat and high-fat diet) factors are associated with increased risks for CRC. The epidemiology of CRC is under dynamic changes owing to the changing prevalence and distribution of risk factors. In this regard, CRC incidence in many developing countries, including Asian countries, has increased 2- to 4-fold over the last two decades and has now reached an alarming rate, with Westernization of diet playing a pivotal role.

It has been verified about 38 trillion bacteria exist the in human intestine. Because of their symbiotic and co-operative relationship with the human body, these bacteria have a close association with the pathogenesis and progression of CRC. The association of CRC with altered gut microbiota has been studied in different populations, identifying certain bacterial species for their potential roles, either beneficial or detrimental, in tumorigenesis.

Several treatment modalities including surgery, chemotherapy, radiation therapy and targeted therapy (e.g., cetuximab and bevacizumab) have been devised to manage CRC. However, the prognosis of patients with metastatic CRC remains dismal, highlighting the importance of prevention as well as early treatment of this disease. The long, stepwise progression of CRC from cellular transformation to full-blown metastatic lesions has enabled its prevention through natural compounds or drugs to block or reverse the process. In particular, economic analysis suggests that chemoprevention could be a cost-effective intervention when targeted at intermediate-risk populations following polypectomy. To this end, non-steroidal anti-inflammatory drugs (NSAIDs) and cyclooxygenase-2 (COX-2) inhibitors have been shown to reduce the occurrence of CRC or its precancerous lesions in high-risk individuals. However, the long-term use of these agents has been associated with an increased risk of cardiovascular events, posing the concern of high-risk benefit ratio for recommending these agents for CRC chemoprevention. The chemo-preventive effects of other agents including folic acid, calcium, vitamin D, and antioxidants have also been explored but their efficacies remain to be fully established.

Probiotics are commensal living microorganisms in the human gut. Managing CRC risk and disease outcome by way of modifying the profile of gut microorganisms is a highly desirable means of medical intervention for its high efficacy, low cost, and low risk of side effects. Thus, there exists a pressing need for developing new and effective methods and compositions useful for the purposes of preventing and treating CRC. This invention fulfills this and other related needs.

BRIEF SUMMARY OF THE INVENTION

The present inventors discovered in their studies that certain gut microbial species and their metabolites are effective for the prevention and treatment of CRC. The microorganisms and metabolites so identified now serve to provide new methods and compositions for reducing an individual's risk of developing CRC at a later time and/or for treating CRC in an individual who has already been diagnosed with the disease.

In a first aspect, the present invention provides a composition that is useful for preventing or treating CRC in a human subject, for example, a person who does not have CRC but is at increased risk for CRC due to family history or with a personal medical history of having had colon cysts or polyps in the past, or a person who has already been diagnosed with CRC. The composition comprises an effective amount of (1) live bacteria Lactobacillus gallinarum or Lactococcus lactis, indole-3-lactic acid (ILA), or an aminopeptidase secreted by L. lactis with a molecular weight of more than 100 kDa, or any combination of two or more of the above; and (2) one or more physiologically acceptable excipients or carriers. In some cases, the composition further comprises an effective amount of live bacteria Carnobacterium maltaromaticum in addition to L. gallinarum, L. lactis, ILA, or the aminopeptidase produced by L. lactis having a greater-than 100 kDa molecular weight. In some embodiments, the composition comprises (a) L. gallinarum and/or L. lactis and (b) C. maltaromaticum in a combined effective amount. In some embodiments, the composition is formulated for oral ingestion, for example, in the form of a food or beverage item, or as an additive to food or beverage. In some embodiments, the composition is in the form of a powder, liquid, paste, cream, tablet, capsule, or caplet. In some embodiments, the composition contains L. gallinarum or L. lactis in the range of about $1 \times 10^8$ to about $1 \times 10^{12}$ colony-forming units (CFU) per gram weight of the composition. In some embodiments, the composition contains live bacteria C. maltaromaticum in range of about $1 \times 10^8$ to about $1 \times 10^{12}$ CFU per gram weight of the composition. In some embodiments, the composition contains L. gallinarum (or L. lactis) to C. maltaromaticum at a CFU ratio between any two bacterial species among the three bacterial species ranging from about 1:5 to about 5:1, for example, from about 1:3 to about 3:1, or from about 1:2 to about 2:1, or about 1:1. In some embodiments, the composition is formulated in multiple packages each in a daily dosage.

In the second aspect, the present invention provides a method for treating or preventing CRC in a subject by administering to the subject an effective amount of the composition described above and herein, namely containing an effective amount of (1) Lactobacillus gallinarum, Lactococcus lactis, ILA, or an aminopeptidase secreted by L. lactis with a molecular weight of greater than 100 kDa, or any combination of two or more of the above; and (2) one or more physiologically acceptable excipients. In some embodiments, the subject has been diagnosed with CRC. In other embodiments, the subject has not been diagnosed with CRC. In some cases, the composition comprises an effective amount of (i) live bacteria *Lactobacillus gallinarum* or *L. lactis*; (ii) *L. gallinarum* or *L. lactis* culture supernatant; (iii) ILA or an aminopeptidase that is produced by *L. lactis* and has a molecular weight higher than 100 kDa; or (iv) any combination of two or more of (i), (ii), and (iii). In some embodiments, the composition further comprises an effective amount of live bacteria *Carnobacterium maltaromaticum*. In some embodiments, the method includes as the administering step administration to the subject a first composition comprising an effective amount of (i) live bacteria *L. gallinarum* or *L. lactis*; (ii) *L. gallinarum* or *L. lactis* culture supernatant; (iii) ILA or an aminopeptidase secreted by *L. lactis* with a molecular weight higher than 100 kDa; or (iv) any combination of two or more of (i), (ii), and (iii), and administering to the subject a second composition comprising an effective amount of live bacteria *C. maltaromaticum*. In some cases, the *L. gallinarum* culture supernatant is the fraction of <3 kDa in molecular weight. In some cases, the *L. lactis* culture supernatant is the fraction of >100 kDa in molecular weight. In some embodiments, the composition used in the method contains live bacteria *L. gallinarum* (or *L. lactis*) and *C. maltaromaticum* each in the range of about $1 \times 10^8$ to about $1 \times 10^{12}$ CFU per gram weight of the composition and at a CFU ratio between any two bacterial species among the three bacterial species ranging from about 1:5 to about 5:1, for example, from about 1:3 to about 3:1, or from about 1:2 to about 2:1, or about 1:1. In some embodiments, one single composition comprising (1) ILA or *L. gallinarum*, *L. lactis*, ILA, or an aminopeptidase secreted by *L. lactis* with a higher than 100 kDa molecular weight and (2) *C. maltaromaticum* is administered. In some embodiments, two or more separate compositions each comprising one or more of live bacteria *L. gallinarum* or *L. lactis*, ILA, an aminopeptidase produced by *L. lactis* with a molecular weight higher than 100 kDa, and *C. maltaromaticum* are administered. In some embodiments, the administration step comprises oral ingestion of the composition(s). In some embodiments, the subject in the claimed method is not diagnosed with any of the diseases or conditions previously known to require administration of *L. gallinarum*, *L. lactis*, ILA, or *C. maltaromaticum*. One exemplary of such disease/condition is colitis.

In a related aspect, the present invention provides a novel use of a composition for treating or preventing CRC in a subject as well as a method of making such a composition. The composition containing an effective amount of (1) *Lactobacillus gallinarum*, *Lactococcus lactis*, ILA, or an *L. lactis*-produced aminopeptidase with a higher than 100 kDa molecular weight, or any combination of two or more of the above; and (2) one or more physiologically acceptable excipients. Optionally, the composition further comprises an effective amount of live bacteria *Carnobacterium maltaromaticum*. The composition may serve as a medicament or food/beverage supplement for the purpose of treating or preventing CRC in a subject with the disease or in a subject without the disease but at risk of later developing the disease. The composition may be produced by combining an effective amount of any one or more of (i) live bacteria *Lactobacillus gallinarum* or *L. lactis*; (ii) *L. gallinarum* or *L. lactis* culture supernatant; (iii) ILA; or (iv) an *L. lactis*-produced aminopeptidase having a molecular weight higher than 100 kDa with at least one possibly more physiologically or pharmaceutically acceptable excipients or carriers to form a mixture, which may take any one of a variety of forms from liquid, semi-liquid, to solid or powder. In some cases, the *L. gallinarum* culture supernatant is the <3 kDa molecular weight fraction of the culture broth. In some cases, the culture supernatant is the >100 kDa molecular weight fraction of the *L. lactis* culture broth. Optionally, an appropriate amount of live bacteria *C. maltaromaticum* is further combined in the mixture, preferably to constitute an effective amount in combination with *L. gallinarum*, *L. lactis*, ILA, or an *L. lactis*-produced aminopeptidase with a >100 kDa molecular weight. In some embodiments, the composition contains live bacteria *L. gallinarum* (or *L. lactis*) and *C. maltaromaticum* each in the range of about $1 \times 10^8$ to about $1 \times 10^{12}$ CFU per gram weight of the composition and at a CFU ratio among any two of the three bacterial species ranging from about 1:5 to about 5:1, for example, from about 1:3 to about 3:1, or from about 1:2 to about 2:1, or about 1:1. In some cases, the composition is formulated for oral ingestion, for example, having been incorporated in a food or beverage item, or as an additive to food or beverage. In some embodiments, the composition is in the form of a powder, liquid, paste, cream, tablet, capsule, or caplet.

In a third aspect, the present invention provides a kit for treating or preventing CRC in a subject comprising (1) a first container containing a first composition comprising an effective amount of *L. gallinarum*, *L. lactis*, ILA, or an *L. lactis*—produced aminopeptidase with a >100 kDa molecular weight; and (2) a second container containing a second composition comprising an effective amount of *C. maltaromaticum*. In some embodiments, the kit includes a first composition containing live bacteria *L. gallinarum* or *L. lactis* present in the range of about $1 \times 10^8$ to about $1 \times 10^{12}$ CFU per gram weight of the first composition, and a second composition containing live bacteria *C. maltaromaticum* is present in the range of about $1 \times 10^8$ to about $1 \times 10^{12}$ CFU per gram weight of the second composition. In some cases, the live bacteria *L. gallinarum* (or *L. lactis*) and *C. maltaromaticum* are present in the first and second positions to be administered together at a CFU ratio between any two of the three bacterial species ranging from about 1:5 to about 5:1, for example, from about 1:3 to about 3:1, or from about 1:2 to about 2:1, or about 1:1. In some embodiments, the compositions are in the form of a powder, liquid, paste, cream, tablet, capsule, or caplet. The kits typically further include an instruction manual providing directions for the user to administer the composition(s) to an appropriate recipient (e.g., one who is at risk of CRC but does not have colitis) in accordance with a pre-determined dosage and frequency.

BRIEF DESCRIPTION OF THE DRAWINGS

FIG. 6 shows that *C. maltaromaticum* modulates gut microbiota in $Apc^{min/+}$ mice. (A) Principal coordinate analysis (PCoA) of species richness of gut microbiota in $Apc^{min/+}$ mice under different treatments. (B) Heatmap representation of modulated bacteria at the genus level in $Apc^{min/+}$ mice. (C) Heatmap representation of differentially abundant bacterial OTUs in $Apc^{min/+}$ mice. Cutoff=|Log 2[fold-change (FC)]|>1 & FDR<0.05. Results are presented as mean±S.D. Statistical significance was determined by one-way ANOVA. OUT, Operational taxonomic unit; C.m, *C. maltaromaticum*.

FIG. 17 shows that *L. gallinarum* induces Try metabolism. (A) Score plots of PCA revealed clear separations of metabolites in culture-supernatant of *L. gallinarum*, *E. coli* MG1655 and control broth groups. (B) Heatmap analysis revealed the abundance of different metabolites in LGCS, ECCS and control broth groups from culture-supernatants. (C) Score plots of PCA revealed clear separations among *L. gallinarum*, *E. coli* MG1655 and control broth treated Apc$^{Min/+}$ mice. (D) Heatmap analysis revealed the abundance of different metabolites in the gut of Apc$^{Min/+}$ mice under different treatments. (E) Heatmap analysis revealed the abundance of tryptophan related metabilites in the gut of Apc$^{Min/+}$ mice under different treatments. P-values are calculated by Student's t-test. *p<0.05, p<0.01, **p<0.0001. ECCS, *E. coli* culture supernatant; LGCS, *L. gallinarum* culture supernatant; PK, proteinase K.

DEFINITIONS

Figure 1:
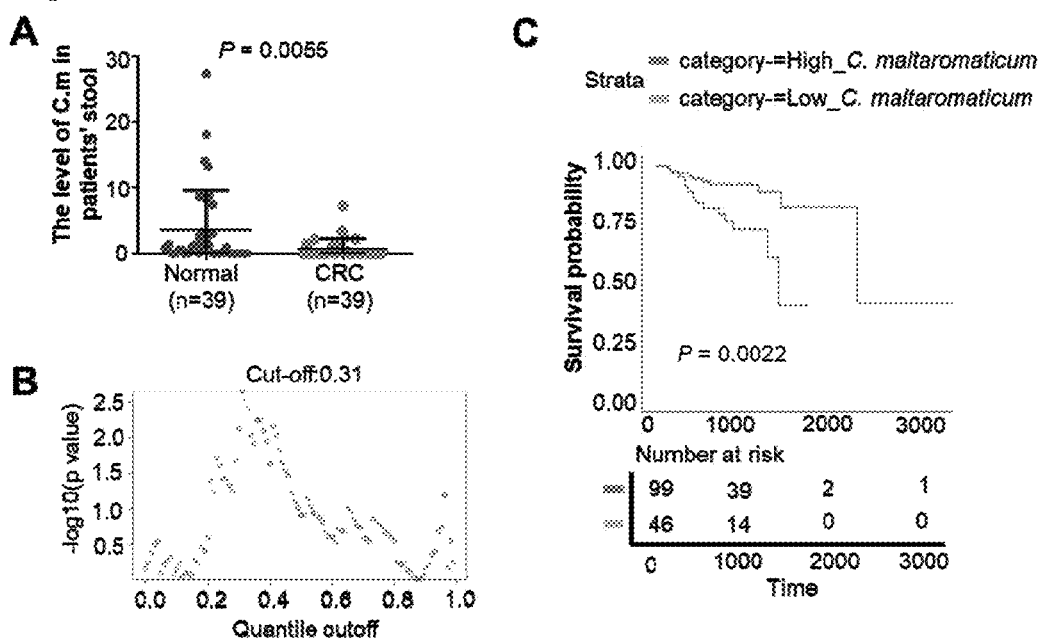
FIG. 1 shows that *C. maltaromaticum* is depleted in stool samples of patients with CRC and predicts overall survival. (A) The abundance of *C. maltaromaticum* in clinical stool samples from normal controls (n=39) and patients with CRC (n=39). (B) The cut-off value for the abundance of *C. maltaromaticum*. (C) The relationship between the abundance of *C. maltaromaticum* and the survival of CRC patients. Results are presented as mean±S.D. Each spot represents one subject. Statistical significance was assessed by Student's t-test.

In this disclosure the terms "colorectal cancer (CRC)" and "colon cancer" have the same meaning and refer to a cancer of the large intestine (colon), the lower part of human digestive system, although rectal cancer often more specifically refers to a cancer of the last several inches of the colon, the rectum. A "colorectal cancer cell" is a colon epithelial cell possessing characteristics of colon cancer and encompasses a precancerous cell, which is in the early stages of conversion to a cancer cell or which is predisposed for conversion to a cancer cell. Such cells may exhibit one or more phenotypic traits characteristic of the cancerous cells.

The term "indole-3-lactic acid" or ILA is used herein to refer to a small molecule that is a metabolite of tryptophan, secreted by certain bacterial species, having the chemical structure shown below:

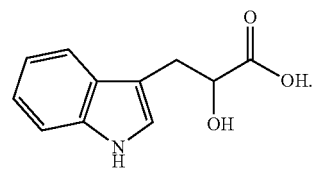 [SMILES: O=C(O)C(O)Cc1c[nH]c2ccccc12]

As used here, "culture supernatant" refers to the aqueous portion of a bacterial culture that has been placed under suitable conditions (e.g., at about 28 to 37° C. for 12-24 hours) permitting log phase proliferation of the bacterial cells and subsequently has the bacterial cells substantially removed, e.g., by centrifugation for at least about 5 minutes, such as about 5-10 minutes, at about 5,000 or higher rpm, such as about 5,000-10,000 rpm. Also encompassed in the concept of a bacteria culture supernatant are aqueous products that have been subject to dilution or concentration or fractionation based on the molecular weight of compounds present in the supernatant.

As used in this application, an "increase" or a "decrease" refers to a detectable positive or negative change in quantity from a comparison control, e.g., an established standard control. An increase is a positive change that is typically at least 10%, or at least 20%, or 50%, or 100%, and can be as high as at least 2-fold or at least 5-fold or even 10-fold of the control value. Similarly, a decrease is a negative change that is typically at least 10%, or at least 20%, 30%, or 50%, or even as high as at least 80% or 90% of the control value. Other terms indicating quantitative changes or differences from a comparative basis, such as "more," "less," "higher," and "lower," are used in this application in the same fashion as described above. In contrast, the term "substantially the same" or "substantially lack of change" indicates little to no change in quantity from the standard control value, typically within ±10% of the standard control, or within ±5%, 2%, 1%, or even less variation from the standard control.

The term "inhibiting" or "inhibition," as used herein, refers to any detectable negative effect on a target biological process, such as RNA/protein expression of a target gene, the biological activity of a target protein, cellular signal transduction, cell proliferation, presence/level of an organism especially a micro-organism, any measurable biomarker, bio-parameter, or symptom in a subject, and the like. Typically, an inhibition is reflected in a decrease of at least 10%, 20%, 30%, 40%, 50%, 60%, 70%, 80%, 90% or greater in the target process (e.g., a subject's bodyweight, or the blood glucose/cholesterol level, or any measurable symptom or biomarker in a subject, such as an infection rate among subjects by a pathogenic infectious agent or a disease incidence), or any one of the downstream parameters mentioned above, when compared to a control. "Inhibition"

further includes a 100% reduction, i.e., a complete elimination, prevention, or abolition of a target biological process or signal or disease/symptom. The other relative terms such as "suppressing," "suppression," "reducing," and "reduction" are used in a similar fashion in this disclosure to refer to decreases to different levels (e.g., at least 10%, 20%, 30%, 40%, 50%, 60%, 70%, 80%, 90% or greater decrease compared to a control level) up to complete elimination of a target biological process or signal or disease/symptom. On the other hand, terms such as "activate," "activating," "activation," "increase," "increasing," "promote," "promoting," "enhance," "enhancing," or "enhancement" are used in this disclosure to encompass positive changes at different levels (e.g., at least about 5%, 10%, 20%, 30%, 40%, 50%, 60%, 70%, 80%, 90%, 100%, 200%, or greater such as 3, 5, 8, 10, 20-fold increase compared to a control level in a target process, signal, or symptom/disease incidence.

As used herein, the term "treatment" or "treating" includes both therapeutic and preventative measures taken to address the presence of a disease or condition or the risk of developing such disease or condition at a later time. It encompasses therapeutic or preventive measures for alleviating ongoing symptoms, inhibiting or slowing disease progression, delaying of onset of symptoms, or eliminating or reducing side-effects caused by such disease or condition. A preventive measure in this context and its variations do not require 100% elimination of the occurrence of an event; rather, they refer to a suppression or reduction in the likelihood or severity of such occurrence or a delay in such occurrence.

The term "severity" of a disease refers to the level and extent to which a disease progresses to cause detrimental effects on the well-being and health of a patient suffering from the disease, such as short-term and long-term physical, mental, and psychological disability, up to and including death of the patient. Severity of a disease can be reflected in the nature and quantity of the necessary therapeutic and maintenance measures, the time duration required for patient recovery, the extent of possible recovery, the percentage of patient full recovery, the percentage of patients in need of long-term care, and mortality rate.

A "patient" or "subject" receiving the composition or treatment method of this invention is a human, including both adult and juvenile human, of any age, gender, and ethnic background, who may not have been diagnosed with any particular disease or disorder (e.g., colon cancer or CRC) but is in need of prophylactic or therapeutic treatment for the disease. Typically, the patient or subject receiving treatment according to the method of this invention to prevent or ameliorate CRC or any of its symptoms is not otherwise in need of treatment by the same therapeutic agents. For example, if a subject is receiving the probiotic composition according to the claimed method, the subject is not suffering from any disease that is known to be treated by the same therapeutic agents. Although a patient may be of any age, in some cases the patient is at least 40, 45, 50, 55, 60, 65, 70, 75, 80, or 85 years of age; in some cases, a patient may be between 40 and 45 years old, or between 50 and 65 years of age, or between 65 and 85 years of age. A "child" subject is one under the age of 18 years, e.g., about 5 to 17, 9 or 10 to 17, or 12 to 17 years old, including an "infant," who is younger than about 12 months old, e.g., younger than about 10, 8, 6, 4, or 2 months old, whereas an "adult" subject is one who is 18 years or older.

The term "effective amount," as used herein, refers to an amount that produces the intended (e.g., therapeutic or prophylactic) effects for which a substance is administered. The effects include the prevention, correction, or inhibition of progression of the symptoms of a particular disease/condition and related complications to any detectable extent, e.g., incidence of disease and related disorder (e.g., CRC). The exact amount will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

The term "about" when used in reference to a given value denotes a range encompassing ±10% of the value. For instance, "about 10" encompasses the range of 9 to 11.

A "pharmaceutically acceptable" or "pharmacologically acceptable" excipient is a substance that is not biologically harmful or otherwise undesirable, i.e., the excipient may be administered to an individual along with a bioactive agent without causing any undesirable biological effects. Neither would the excipient interact in a deleterious manner with any of the components of the composition in which it is contained.

The term "excipient" refers to any essentially accessory substance that may be present in the finished dosage form of the composition of this invention. For example, the term "excipient" includes vehicles, binders, disintegrants, fillers (diluents), lubricants, glidants (flow enhancers), compression aids, colors, sweeteners, preservatives, suspending/dispersing agents, film formers/coatings, flavors and printing inks.

The term "consisting essentially of," when used in the context of describing a composition containing an active ingredient or multiple active ingredients, refers to the fact that the composition does not contain other ingredients possessing any similar or relevant biological activity of the active ingredient(s) or capable of enhancing or suppressing the activity, whereas one or more inactive ingredients such as physiological or pharmaceutically acceptable excipients may be present in the composition. For example, a composition consisting essentially of active agents (for instance, a combination of *L. gallinarum* and *C. maltaromaticum*) effective for treating or preventing CRC in a subject is a composition that does not contain any other agents that may have any detectable positive or negative effect on the same target process (e.g., inhibition of the onset or progression of tumorigenesis of the colon) or that may increase or decrease to any measurable extent of the disease severity among the receiving subjects.

DETAILED DESCRIPTION OF THE INVENTION

I. Introduction

Using fecal shotgun metagenomic sequencing, the present inventors have previously identified *Lactobacillus gallinarum* as one of the most depleted probiotic species in the stool of colorectal cancer (CRC) patients. This study was intended to determine the potential anti-tumorigenic role of *L. gallinarum*, optionally in combination with another one or two bacterial species (such as *Lactococcus lactis* or *Carnobacterium maltaromaticum*), in colorectal tumorigenesis.

Specifically, $Apc^{min/+}$ mice and azoxymethane/dextran sulfate sodium-treated mice were gavaged with *L. gallinarum*, *E. coli* MG1655 (control bacteria), or plain culture broth daily until the development of neoplastic lesions. Intestinal tumor numbers and sizes were determined after sacrifice. CRC organoids and CRC cell lines (HCT116 and LoVo) were cultured with *L. gallinarum* or *E. coli* MG1655 culture-supernatant to evaluate cell proliferation, apoptosis and cell cycle distribution. Gut microbiota was assessed by 16S rRNA sequencing. Anti-tumor molecule produced from *L. gallinarum* was identified by liquid chromatography mass spectrometry (LC-MS/MS) and targeted mass spectrometry assay.

*L. gallinarum* significantly reduced intestinal tumor number and size compared with *E. coli* MG1655 and plain culture broth in both male and female murine intestinal tumorigenesis models. Fecal microbial profiling revealed the enrichment of probiotics and depletion of pathogenic bacteria in *L. gallinarum*-treated mice. Culturing CRC cells with *L. gallinarum* culture-supernatant (5%, 10% and 20%) concentration-dependently suppressed cell proliferation and colony formation. *L. gallinarum* culture-supernatant significantly promoted apoptosis in CRC cells and patient-derived organoids, but not in normal colon epithelial cells. Only *L. gallinarum* culture-supernatant with fraction size<3 kDa suppressed cell proliferation in CRC cells. Using LC-MS/MS, L-Tryptophan was identified to be increased in both of the *L. gallinarum* culture-supernatant and *L. gallinarum*-treated mice gut. Further high throughput tryptophan targeted metabonomics revealed that indole-3-lactic acid (ILA) was one of the most significantly increased low-molecular-weight metabolite (<3 kDa) secreted by *L. gallinarum*.

In summary, this study provides the following observations: (1) *L. gallinarum* inhibited colorectal tumorigenesis in Apc$^{min/+}$ mice and in azoxymethane/dextran sulfate sodium-treated mice; (2) *L. gallinarum* increased the abundance of gut probiotics and depleted potential gut pathogens; (3) *L. gallinarum* culture-supernatant suppressed cell proliferation and induced apoptosis in patient-derived organoids and in CRC cell lines; and (4) Non-protein secreted molecule(s) with a molecular weight<3 kDa from *L. gallinarum* mediated the anti-CRC effect. Indole-3-lactic acid, a small molecule with known anti-inflammatory property, was identified as the most enriched metabolite secreted by *L. gallinarum*. Similarly, *Lactococcus lactis* and at least one high molecular weight (>100 kDa) protein with aminopeptidase activity in the *L. lactis* culture have been shown to possess a suppressive activity on the CRC cells. It is therefore concluded that *L. gallinarum* as well as *L. lactis* protects against intestinal tumorigenesis by producing protecting metabolites that can promote apoptosis on CRC cells.

II. Pharmaceutical Compositions and Administration

The present invention provides pharmaceutical compositions comprising an effective amount of live bacteria *L. gallinarum* or *L. lactis*, ILA, or an aminopeptidase produced by *L. lactis* with a >100 kDa molecular weight, optionally in further combination with live bacteria *C. maltaromaticum*, for administration to a person to reduce the risk of later developing CRC or to treat CRC a person already suffers from. Pharmaceutical compositions of the invention are suitable for use in a variety of drug delivery systems. Suitable formulations for use in the present invention are found in *Remington's Pharmaceutical Sciences*, Mack Publishing Company, Philadelphia, PA, 17th ed. (1985). For a brief review of methods for drug delivery, see, Langer, *Science* 249: 1527-1533 (1990).

The pharmaceutical compositions of the present invention can be administered by various routes, e.g., systemic administration via oral ingestion or local delivery using a rectal suppository. The preferred route of administering the pharmaceutical compositions is oral administration at daily doses of about $10^8$ to about $10^{12}$ CFU for live bacteria *L. gallinarum* or *L. lactis*, or a combination of live bacteria *L. gallinarum* (or *L. lactis*) and *C. maltaromaticum*, at a ratio among any two of the bacteria species ranging from about 1:5, 1:4, 1:3, 1:2, 1:1, 2:1, 3:1, 4:1, to about 5:1. These two or three species of bacteria may be administered either in one single composition or in multiple compositions. Optionally, the small molecule of ILA, a downstream catabolite of L-tryptophan (Try) secreted by *L. gallinarum*, or an aminopeptidase produced by *L. lactis* with a molecular weight of greater than 100 kDa, is administered to the subject in lieu of live bacteria *L. gallinarum* or *L. lactis*. Typically, ILA or the aminopeptidase may be present in the composition for administration in the range of about 0.5 to about 50 or 100, or about 1 to about 20 or 25, or about 2 to about 10 or 15, or about 5 to about 10 mg per kg patient bodyweight. As a further alternative, *L. gallinarum* or *L. lactis* culture supernatant, which may have been further processed, e.g., fractionated to capture molecular weight range of less than about 3 kDa or greater than about 100 kDa, respectively.

For preparing pharmaceutical compositions containing live bacteria *L. gallinarum* or *L. lactis*, ILA, or the *L. lactis*—produced aminopeptidase with a molecular weight greater than about 100 kDa, optionally in combination with live bacteria *C. maltaromaticum*, one or more inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component, e.g., *L. gallinarum*, *L. lactis*, ILA, or the *L. lactis*-secreted aminopeptidase with a molecular weight of greater than about 100 kDa, optionally further in combination with *C. maltaromaticum*. In tablets, the active ingredient is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 100% by weight of the active ingredient(s) (e.g., *L. gallinarum*, *L. lactis*, ILA, or the *L. lactis*-secreted aminopeptidase with a molecular weight of >100 kDa, optionally further in combination with *C. maltaromaticum*). Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active ingredient(s) e.g., *L. gallinarum*, *L. lactis*, ILA, or the *L. lactis*-secreted aminopeptidase with a molecular weight of >100 kDa, optionally further in combination with *C. maltaromaticum*, with encapsulating material as a carrier providing a capsule in which the active ingredient(s) (with or without other carriers) is surrounded by the carrier, such that the carrier is thus in association with the active ingredient(s). In a similar manner, sachets can also be included. Tablets, powders, sachets, and capsules can be used as solid dosage forms suitable for oral administration.

Liquid pharmaceutical compositions include, for example, solutions suitable for oral administration or local delivery, suspensions, and emulsions suitable for oral administration. Sterile water solutions of the active component (e.g., *L. gallinarum, L. lactis*, ILA, or the *L. lactis*-secreted aminopeptidase with a molecular weight of >100 kDa, optionally further in combination with *C. maltaromaticum*) or sterile solutions of the active component in solvents comprising water, buffered water, saline, PBS, ethanol, or propylene glycol are examples of liquid or semi-liquid compositions suitable for oral administration or local delivery such as by rectal suppository. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component (e.g., *L. gallinarum, L. lactis*, ILA, or the *L. lactis*-secreted aminopeptidase with a molecular weight of >100 kDa, optionally further in combination with *C. maltaromaticum*) in the desired solvent system, and then passing the resulting solution through a membrane filter to sterilize it or, alternatively, by dissolving the sterile active component in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9, and most preferably from 7 to 8.

Single or multiple administrations of the compositions can be carried out with dose levels and pattern being selected by the treating physician. In any event, the pharmaceutical formulations should provide a quantity of an active agent sufficient to effectively enhance the efficacy of a vaccine and/or reduce or eliminate undesirable adverse effects of a vaccine.

III. Kits

The invention also provides kits for reducing the risk of later developing CRC or for inhibiting progression of the disease/reducing severity of the disease symptoms in an individual according to the method disclosed herein. The kits typically include a plurality of containers, each containing a composition comprising one or more of the active agents, such as live bacteria *L. gallinarum, L. lactis*, and *C. maltaromaticum*, or one or more proteins secreted by the bacteria, e.g., ILA or an aminopeptidase produced by *L. lactis* having a >100 kDa molecular weight. For example, a first container contains an effective amount of live bacteria *L. gallinarum* or *L. lactis*, and a second container contains an effective amount of live bacteria *C. maltaromaticum*. As another example, a first container contains an effective amount of ILA or the aminopeptidase, or supernatant of an *L. gallinarum* or *L. lactis* culture, and a second container contains an effective amount of live bacteria *C. maltaromaticum*. As an additional example, the kits include one single container contains live bacteria *L. gallinarum* (or *L. lactis*) and live bacteria *C. maltaromaticum*, combinedly in an effective amount for the intended purpose. Further, additional agents or drugs that are known to be therapeutically effective for prevention and/or treatment of the disease, including for ameliorating the symptoms and reducing the severity of the disease, as well as for facilitating recovery from the disease may be included in the kit. The plurality of containers of the kit each may contain a different active agent/drug or a distinct combination of two or more of the active agents or drugs. The kit may further include informational material providing instructions on how to dispense the pharmaceutical composition(s), including description of the type of patients who may be treated, e.g., human patients who have been deemed as with high risk of developing the disease, for example, due to genetic predisposition, family history of cancer (especially colon cancer), and/or personal traits and medical background such as age (50 years or older), gender (male), diabetes mellitus, obesity, and inflammatory bowel disease, as well as smoking and certain dietary choices, e.g., inadequate intake of fiber, high consumption of alcohol, red meat, and high salt or high fat or preserved foods, as well as the type of patients not to be included in the claimed method, e.g., those who have been diagnosed with a pre-existing condition, such as colitis, that already requires the administration of the active components such as *L. gallinarum, L. lactis*, ILA, the *L. lactis*-secreted aminopeptidase with a molecular weight of >100 kDa, or *C. maltaromaticum*), the dosage, frequency, and manner of administration, and the like.

EXAMPLES

The following examples are provided by way of illustration only and not by way of limitation. Those of skill in the art will readily recognize a variety of non-critical parameters that could be changed or modified to yield essentially the same or similar results.

Example I: *Carnobacterium maltaromaticum* Modulates the Gut Microbiota and Enhances Vitamin D-Related Metabolites to Protect Against Colorectal Tumorigenesis Background of the Invention Colorectal cancer (CRC) is one of the most commonly diagnosed and deadly malignancies worldwide. Along with genetic, epigenetic, and environmental factors, the role of gut microbiota in the initiation and progression of CRC has been recognized in the past decades[1]. The dysbiosis of microbes during the long, stepwise progression of intestinal tumorigenesis enabled possible CRC prevention through maintaining intestinal microbial balance by consumption of CRC-depleted probiotics and its metabolites[2].

So far, probiotics-based therapeutics have aroused interest from the medical community given their high safety profile. Administration of probiotics, such as *Lactobacillus casei* (strain BL23), *Clostridium butyricum*, and *Bifidobacterium bigidum*, have been found to re-establish the gut microbial balance by diminishing the colonization of pathogens[3]. Clinical studies also showed oral administration of *Bifidobacterium* and *Lactobacillus* probiotics could mitigate dysbiosis in CRC patients, thereby supporting the possibility of using probiotics as prophylactics for maintaining healthy microbiota states with minimal side effects[4]. In addition to the microbial interactions, health-promoting metabolites secreted from probiotics could exert direct anti-cancer effects[5]. The metagenomic profiling from previous studies has demonstrated that *Streptococcus thermophilus*, a CRC-depleted probiotic, could prevent intestinal tumorigenesis through secreting β-galactosidase[6]. These findings support the importance of determining the tumor-suppressing effect of other CRC-depleted bacteria to provide new strategies for CRC prevention.

Using shotgun metagenomic sequencing of 526 multi-cohort fecal samples from 255 CRC patients and 271 healthy controls, the present inventors have identified a probiotic species, namely *Carnobacterium maltaromaticum* (*C. maltaromaticum*), being significantly depleted in the stool of CRC patients. Here, the functional role of *C. maltaromati-*

*cum* in mitigating colorectal tumorigenesis in mouse models and cultured CRC cells is elucidated. This tumor-suppressing effect has been revealed to be attributed to the activated biosynthetic pathway of vitamin D.

Materials and Methods

*C. maltaromaticum* Quantification in Human Fecal Samples

Human stool samples were collected form 78 adults and the fecal DNAs were extracted as described previously. Amplification and detection of *C. maltaromaticum* were conducted using Universal SYBR Green Master reaction, and the reaction was analyzed by QUANTSTUDIO™ 7 Flex System (Thermo Fisher Scientific Waltham, MA). This study protocol was approved by the Joint CUHK-NTEC Clinical Research Ethics Committee. Written informed consents were obtained from individuals.

Bacteria Strains and Growth Conditions

*C. maltaromaticum* (ATCC B270) and *Escherichia coli* strain MG1655 (ATCC 700926) were purchased from American Type Culture Collection (ATCC; Manassas, VA). They were cultured in Brain Heart Infusion (BHI) broth (CM1135B; Thermo Fisher Scientific, West Palm Beach, FL) at 37° C. under aerobic condition for 24 hours before use.

Cell Culture

Colon cancer cell lines HCT116 and DLD1 were obtained from American Type Culture Collection (ATCC). Normal colonic epithelial cell line NCM460 was obtained from INCELL Corporation (San Antonio, TX). All the cell lines were cultured in high-glucose Dulbecco's Modified Eagle's Medium (DMEM) (Thermo Fisher Scientific) supplemented with 10% (vol/vol) fetal bovine serum (FBS) (Thermo Fisher Scientific), 1% penicillin/streptomycin in a humidified atmosphere containing 5% $CO_2$. For co-culture of epithelial cells with bacteria, the penicillin/streptomycin in the culture medium was removed and cells were exposed to bacteria with a multiplicity of infection (MOI) of 200 for 2 hours. Cell viability and cell cycle were determined in the same way as we reported previously.

Adenomatous Polyposis Coli/Multiple Intestinal Neoplasia CRC Model

C57BL/6J-ApcMin/J mice, which develop intestinal polyps spontaneously was used as a model of spontaneous intestinal neoplasia. They were purchased from the Jackson Laboratory (Bar Harbor, ME, USA) and maintained in the animal facility at the Chinese University of Hong Kong. Mice at 4-5 weeks old were divided into 3 groups $-1\times10^8$ colony forming units (CFU) of *C. maltaromaticum* or *E. coli* MG1655, or the same volume of BHI was gavaged to them once daily for 12 weeks. Colorectal tumor formation was monitored by mouse colonoscopy (COLOVIEW™, KARL STROZ®, Germany). Stool samples were collected weekly.

Carcinogen-Induced Colon Cancer Model 5-week-old male conventional C57BL/6 wild-type mice were subject to 6 consecutive injections of azoxymethane (AOM; 10 mg/kg, intraperitoneal injection) at 1-week intervals to induce sporadic CRC. The same treatment regimen with the $Apc^{min/+}$ mice was used in this AOM model. Mice were raised to 26 weeks for the evaluation of the probiotic treatment efficacy. All experimental procedures adhered to the guidelines approved by the Animal Ethics Committee of the Chinese University of Hong Kong.

16S rRNA Gene Sequencing

Mice fecal DNA extraction and purification were performed by using QUICK-DNA™ Fecal/Soil Microbe Miniprep Kit (Zymo Research, Irvine, CA). DNA library was constructed on Illumina MISEQ™ platform as described in our previous study[7]. University primers 341F (SEQ ID NO:1: 5'-CCTAYGGGRBGCASCAG-3') and 806R (SEQ ID NO:2: 5'-GGACTACNNGGGTATCTAAT-3') targeting 16S rRNA genes V3-V4 hypervariable regions were used for sequencing. Bacteria OUTs with $P<0.05$ and $|\log 2[\text{fold change (FC)}]|>1$ (FC>2 or FC<0.5) were deemed statistically significant.

Metabolomics Profiling and Metabolites Analysis

Metabonomics was performed by BIOTREE, Shanghai, China. The metabolites were transferred to a fresh glass vial for liquid chromatography-tandem mass spectrometry (LC-MS/MS) analysis. Ultra-high performance liquid chromatography (UHPLC) separation was carried out using a 1290 INFINITY® series UHPLC System (Agilent Technologies, Palo Alto, CA), equipped with a UPLC BEH Amide column. The TRIPLETOF® 6600 mass spectrometry (AB Sciex, Foster City, California) was used to acquire tandem mass spectrometry (MS/MS) spectra on an information-dependent basis during LC-MS/MS experiment. The metabolite identification was based on in-house MS2 database, Human Metabolome Database (HMDB, see website: hmdb.ca), and METLIN® metabolite database (see website: metlin.scripps.edu).

Vitamin D Concentration in Colonic Mucosa

Colonic samples were washed in PBS and dissected in extraction buffer (2:1 methanol:methylene chloride) prior to homogenization. Samples were then vortexed and centrifuged at 10,000×g for 10 minutes. The supernatant was carefully collected and evaporated under a gentle stream of nitrogen at 37° C. The dried samples were reconstituted with ELISA buffer and the $1\alpha,25$-dihydroxyvitamin $D_3$ ($1,25(OH)_2D_3$) level was measured by using Vitamin D ELISA Kit (Cayman, MI, USA) following the manufacture's instruction. The remaining protein was re-extracted with radioimmunoprecipitation assay buffer (RIPA) for vitamin D concentration normalization.

Reverse Transcription-Quantitative PCR (RT-qPCR)

Total RNAs were extracted from cell pellets or colonic tissues using TRIZOL™ Reagent (Life Technologies). Complementary DNA (cDNA) was prepared using PRIME-SCRIPT™ RT Reagent Kit with gDNA Eraser (Takara, Shiga, Japan). The relative level of specific genes was determined by QUANTSTUDIO™ 7 Flex Real-Time PCR System (Thermo Fisher Scientific).

Western Blot

Total protein from cell pallets or colonic tissues was isolated and separated by SDS-PAGE (6%-12%). The protein in SDS-PAGE was then transferred onto polyvinylidene difluoride (PVDF) membranes (EMD Millipore, Billerica, MA, USA) for about 1-2 hours, which was then blocked with 10% non-fat milk in 0.05% Tris-based saline-Tween 20 for 2 hours at room temperature. The membrane was incubated with primary antibodies overnight at 4° C. and then with secondary antibody at room temperature for 1 hour. The protein band intensities were detected by ECL Plus Western Blotting Detection Reagents (GE Healthcare).

Transmission Electron Microscopy (TEM)

Colonic tissues were dissected into small pieces and fixed in 2.0% glutaraldehyde in 0.1M sodium cacodylate (Electron Microscopy Sciences, Hatfield, PA). Ultrathin sections were prepared on a Reichert Ultracut E ultramicrotome. The ultrastructure images of the tissues were acquired using a Philips CM100 TEM.

Colonic Permeability Assay

Colonic permeability was determined by measuring the levels of lipopolysaccharides (LPS) in serum by a mouse LPS enzyme-linked immune sorbent assay (ELISA) Kit (Cusabio, Wuhan, China) according to the manufacturer's instruction.

Alcian Blue-Periodic Acid Schiff (AB-PAS) Staining

Carnoy's solution-fixed colonic tissues were prepared for AB-PAS staining as we described previously[8]. Briefly, the mucus-containing colon sections were stained purple-red. The thickness of the mucus-secreting layer was measured perpendicularly to the mucosal surface from the edge of the epithelium to the outermost part of the mucus-secreting layer under microscopy at 100× magnification. Five random microscopic fields were counted for each sample.

Ki-67 Immunohistochemistry (IHC) Staining

Paraffin-embedded colon sections were used for Ki-67 (Abcam, 16667) IHC staining. The proportion of Ki-67 positive cells was used for determining the cell proliferation index. One thousand cells in five random microscopic fields were counted for each sample.

VDR Immunofluorescence (IF) Staining

Paraffin-embedded colon sections were deparaffinized, antigen-retrieved, blocked, and incubated with primary VDR antibody (Cell Signaling Technology, 12550). The mean fluorescence intensity (MFI) of nuclear VDR was measured under a laser scanning confocal microscope (LEICA TCS SP8, Wetzlar, Germany).

Gene Expression Profiling from RNA-Seq in the Cancer Genome Atlas (TCGA) Dataset The gene expression data of colon adenocarcinoma samples were retrieved from The Cancer Genome Altas (TCGA) database using the TCGAbiolinks R package[9]. The unaligned RNA-seq data in fastq format of colon adenocarcinoma were downloaded from The Cancer Genome Altas (TCGA) database[10]. The pathseq[11] pipeline was used to map those unaligned RNA-seq reads to gut-related bacteria after subtraction of human reads and low quality. The pre-built host genome was obtained from the GATK Resource Bundle FTP server in /bundle/pathseq/. The microbe references used here included 1520 cultivated bacterial genomes[12] and also colon cancer related bacteria which were identified through extensive and statistically-rigorous validation[7,13]. The normalized score generated by pathseq was used as a relative transcriptome abundance for each species. This study meets the publication guidelines provided by TCGA (see detailed description at website: cancergenome.nih.gov/publications/publicationguidelines).

Statistical Analysis

Values are expressed as mean±standard deviation (SD) for both in vivo and in vitro experiments. Comparisons between two groups were performed using a two-sided Student's t-test. Analysis of variance (ANOVA) was used to compare differences among multiple groups, and post-hoc analysis was performed by Tukey's multiple comparisons test. P-values<0.05 indicate statistical significance.

Results

C. maltaromaticum is Depleted in Stool Samples of Patients with CRC

To further verify the reduced abundance of C. maltaromaticum in CRC, qPCR was performed with stool samples from 39 patients with CRC and 39 healthy individuals. As shown in FIG. 1A, C. maltaromaticum was significantly depleted in stool samples from patients with CRC as compared with those from normal subjects (P=0.0055). Survival probability data from TCGA further revealed that the high abundance of C. maltaromaticum was associated with a better survival of CRC patients (FIG. 1B), indicating the possible anti-CRC effect of C. maltaromaticum.

C. maltaromaticum Inhibits the Viability of Colon Cancer Cells

Figure 2:
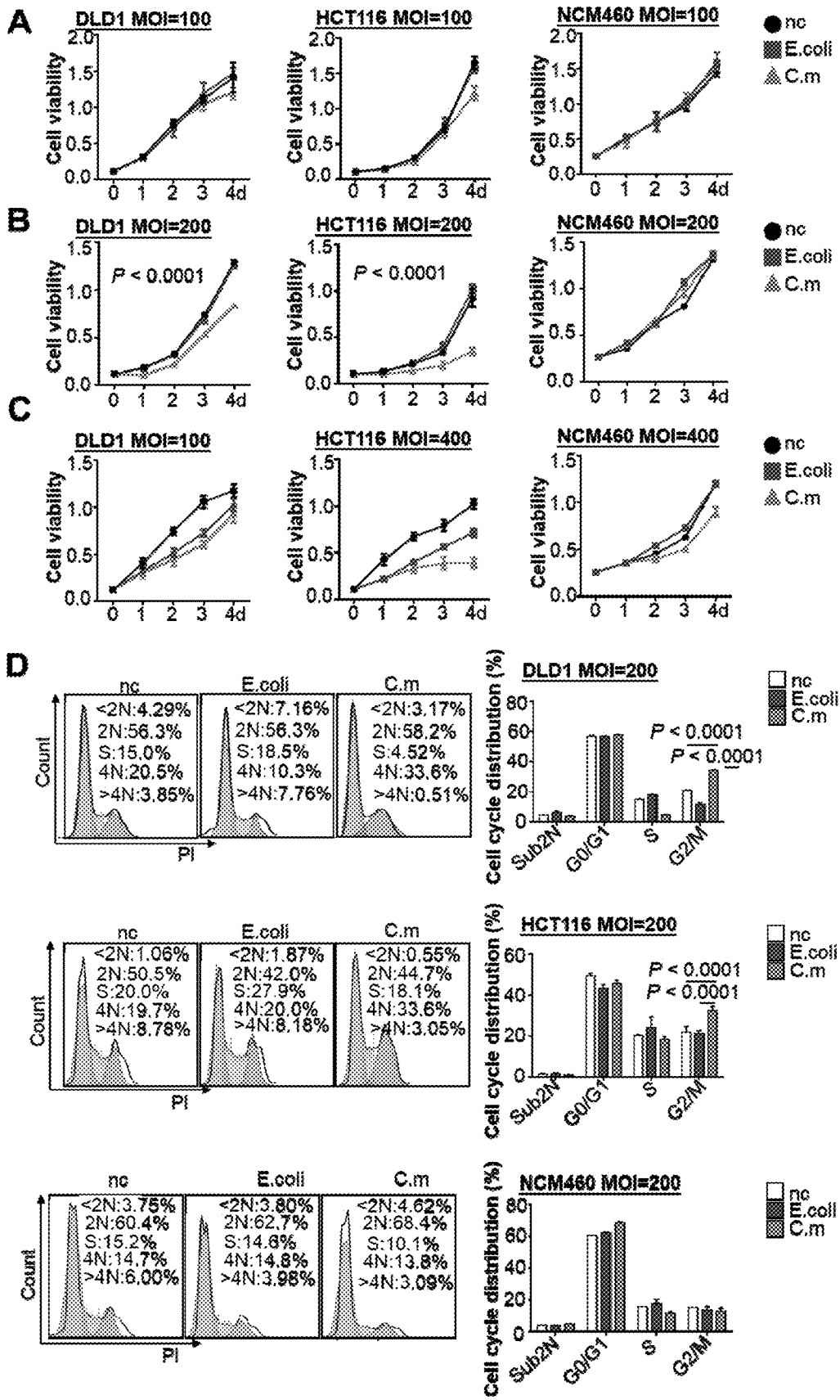
FIG. 2 shows that *C. maltaromaticum* inhibits the viability and induces $G_2$/M-phase cell cycle arrest of colon cancer cells. (A) The viability of CRC cells (HCT116, DLD1) and normal colon cells (NCM460) after co-incubation with or without *C. maltaromaticum* (MOI=100). *E. coli* was used as bacteria control. (B) The viability of CRC cells (HCT116, DLD1) and normal colon cells (NCM460) after co-incubation with or without *C. maltaromaticum* (MOI=200) (C) The viability of CRC cells (HCT116, DLD1) and normal colon cells (NCM460) after co-incubation with or without *C. maltaromaticum* (MOI=400). (D) The cell cycle distribution of colon cells after co-incubation with or without *C. maltaromaticum*. *E. coli* was used as bacteria control. Results are presented as mean±S.D. Statistical significance was determined by one-way ANOVA or two-way ANOVA where appropriate.

To investigate the direct tumor-suppressive effect of C. maltaromaticum in vitro, CRC cell lines DLD1 and HCTLL6, and colon normal epithelial cell line NCM460, were co-incubated with C. maltaromaticum at MOI of 100, 200 and 400 for 2 hours in aerobic condition, respectively. E. coli strain MG1655 was used as bacteria control. It was discovered that C. maltaromaticum significantly decreased the number of viable CRC cells, but not the normal colonic epithelial cells at MOI of 200 (FIG. 2A-2C). In keeping with this, C. maltaromaticum treatment retarded cell cycle progression of CRC cells in the G2/M phase at MOI of 200 (FIG. 2D). These results indicate that the CRC-depleted C. maltaromaticum could suppress the CRC cell proliferation directly.

Figure 3:
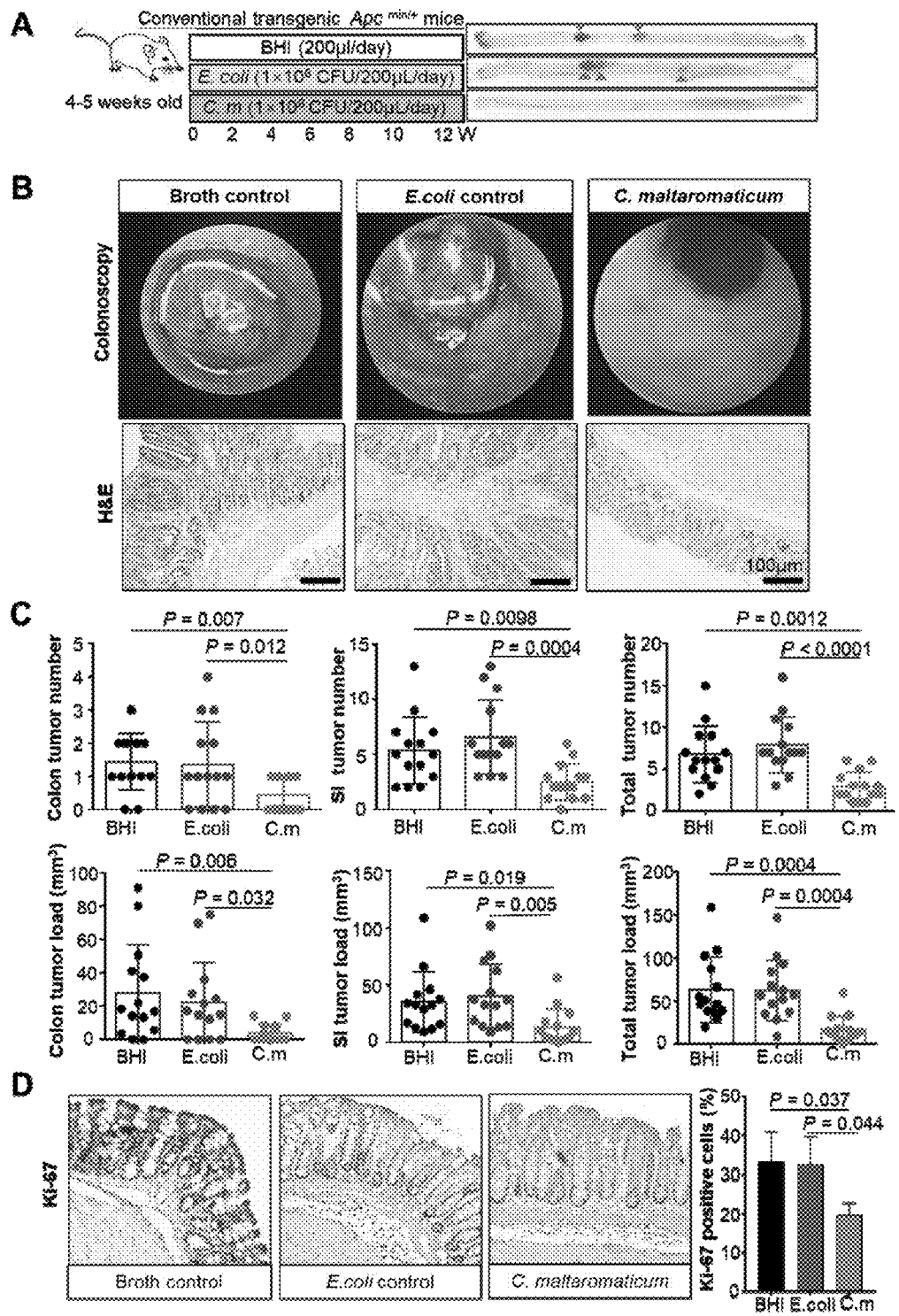
FIG. 3 shows that *C. maltaromaticum* protects against intestinal tumorigenesis in $Apc^{min/+}$ mice. (A) Schematic diagram showing the experimental design, timeline, and representative colonic morphologies of $Apc^{min/+}$ mice under different treatments. (B) Representative images of colon tumor under colonoscopy (upper panels) and representative H&E-stained histological images (lower panels) from $Apc^{min/+}$ mice under different treatments. Scale bar=100 μm. (C) Colonic and small intestine tumor number (upper three panels) and tumor load (lower three panels) of $Apc^{min/+}$ mice under different treatments. (D) Immunohistochemistry staining of Ki-67$^+$ cells in mice colons with quantitative analysis of Ki-67$^+$ index. Results are presented as mean±S.D. Statistical significance was determined by one-way ANOVA. C.m, *C. maltaromaticum*; SI, small intestine; W, week.

C. maltaromaticum Protects Against Intestinal Tumorigenesis in Apc$^{min/+}$ Mice To validate the suppressive effect of C. maltaromaticum on colorectal tumorigenesis in vivo, 200 µl of bacterial suspension containing 1×10$^8$ CFU of C. maltaromaticum was orally gavaged to 5-week-old Apc$^{min/+}$ mice daily for 12 consecutive weeks. The same volume of BHI or same amount of E. coli (strain MG1655) were used as control and administrated to the mice the same way as C. maltaromaticum (FIG. 3A). Mouse colonoscopy was performed before harvest. Visually reduced tumor size was observed in C. maltaromaticum-gavaged mice as compared with E. coli strain MG1655 or BHI treatment (FIG. 3B, upper). After sacrifice, significantly reduced tumor number and tumor load were observed in both colon and small intestine of C. maltaromaticum treated Apc$^{min/+}$ mice (FIG. 3C). The tumor histology was further examined (FIG. 3B, lower), and the decreased proportion of Ki-67$^+$ colonic epithelial cells was also observed in C. maltaromaticum-treated Apc$^{min/+}$ mice (FIG. 3D) as compared with both BHI- and E. coli strain MG1655-treated group, indicating that C. maltaromaticum could protect against intestinal tumorigenesis in Apc$^{min/+}$ mice.

Figure 4:
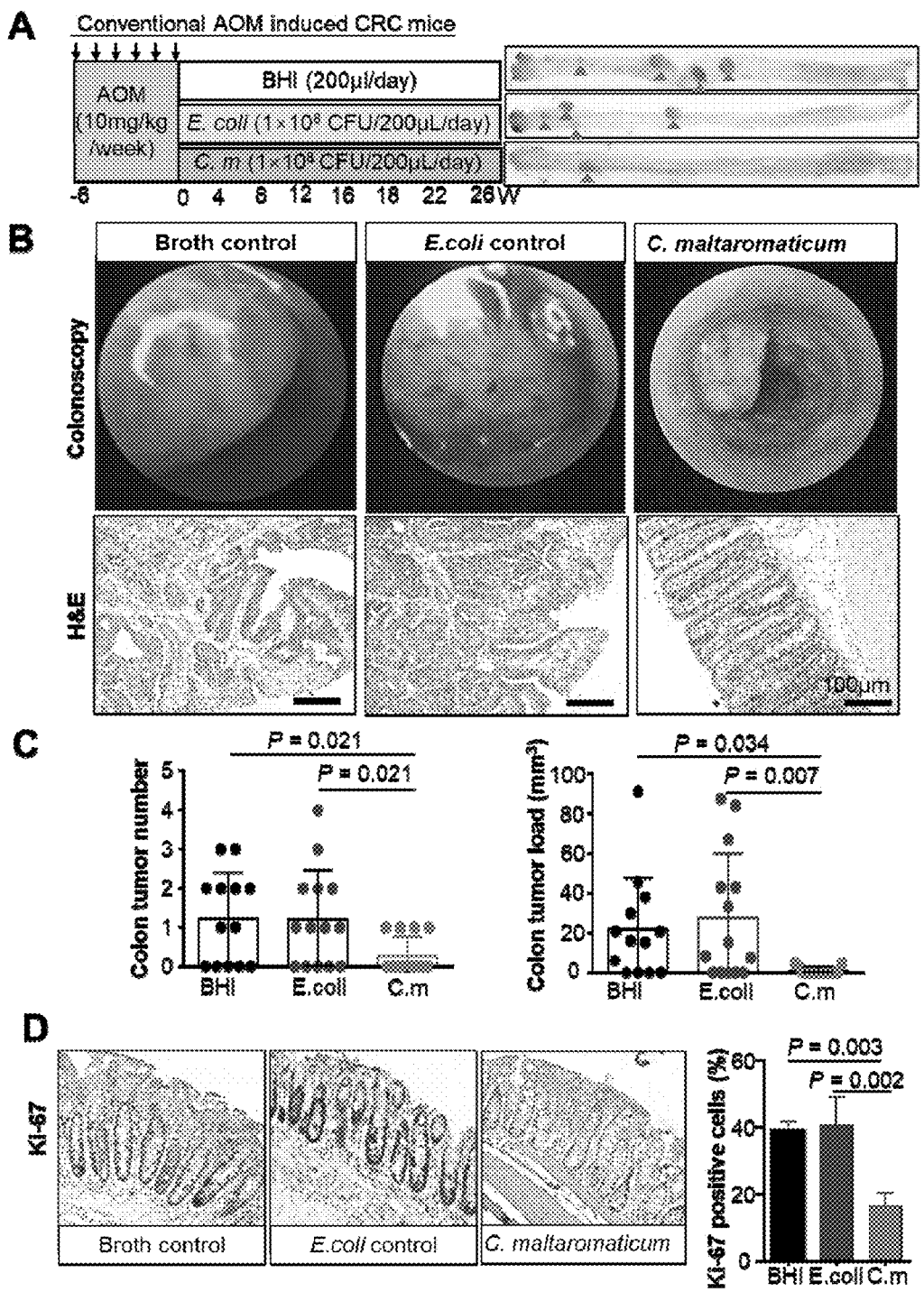
FIG. 4 shows that *C. maltaromaticum* protects against intestinal tumorigenesis in azoxymethane (AOM)-induced CRC mice. (A) Schematic diagram showing the experimental design, timeline, and representative colonic morphologies of AOM-induced CRC mice model under different treatments. (B) Representative images of colon tumor under colonoscopy (upper panels) and representative H&E-stained histological images (lower panels) from AOM-induced CRC mice model under different treatments. Scale bar=100 μm. (C) Colonic tumor number (left panel) and tumor load (right panel) of AOM-induced CRC mice under different treatments. (D) Immunohistochemistry staining of Ki-67$^+$ cells in mice colons with quantitative analysis of Ki-67$^+$ index. Results are presented as mean±S.D. Statistical significance was determined by one-way ANOVA. C.m, *C. maltaromaticum*; AOM, azoxymethane; W, week.

C. maltaromaticum Protects Against Intestinal Tumorigenesis in AOM-Induced CRC Mice To further verify the CRC-suppressive effect of C. maltaromaticum, an AOM-induced CRC model was established, in which 5-week-old C57BL/6 mice were injected with the carcinogen AOM (10 mg/kg) once a week for 6 weeks, followed by oral administration of C. maltaromaticum, E. coli strain MG1655 or BHI for 26 weeks (FIG. 4A). Visual reduction of tumor size was observed in C. maltaromaticum-treated mice during colonoscopy (FIG. 4B, upper). The tumor number and tumor load were also decreased in C. maltaromaticum-treated mice (FIG. 4C). Histological occurrence of CRC was further confirmed (FIG. 4B, lower) and the Ki-67 positive cells were also found to be decreased in C. maltaromaticum-treated mice (FIG. 4D). These findings indicated that C. maltaromaticum could also suppress intestinal tumorigenesis in AOM-induced CRC mice.

Figure 5:
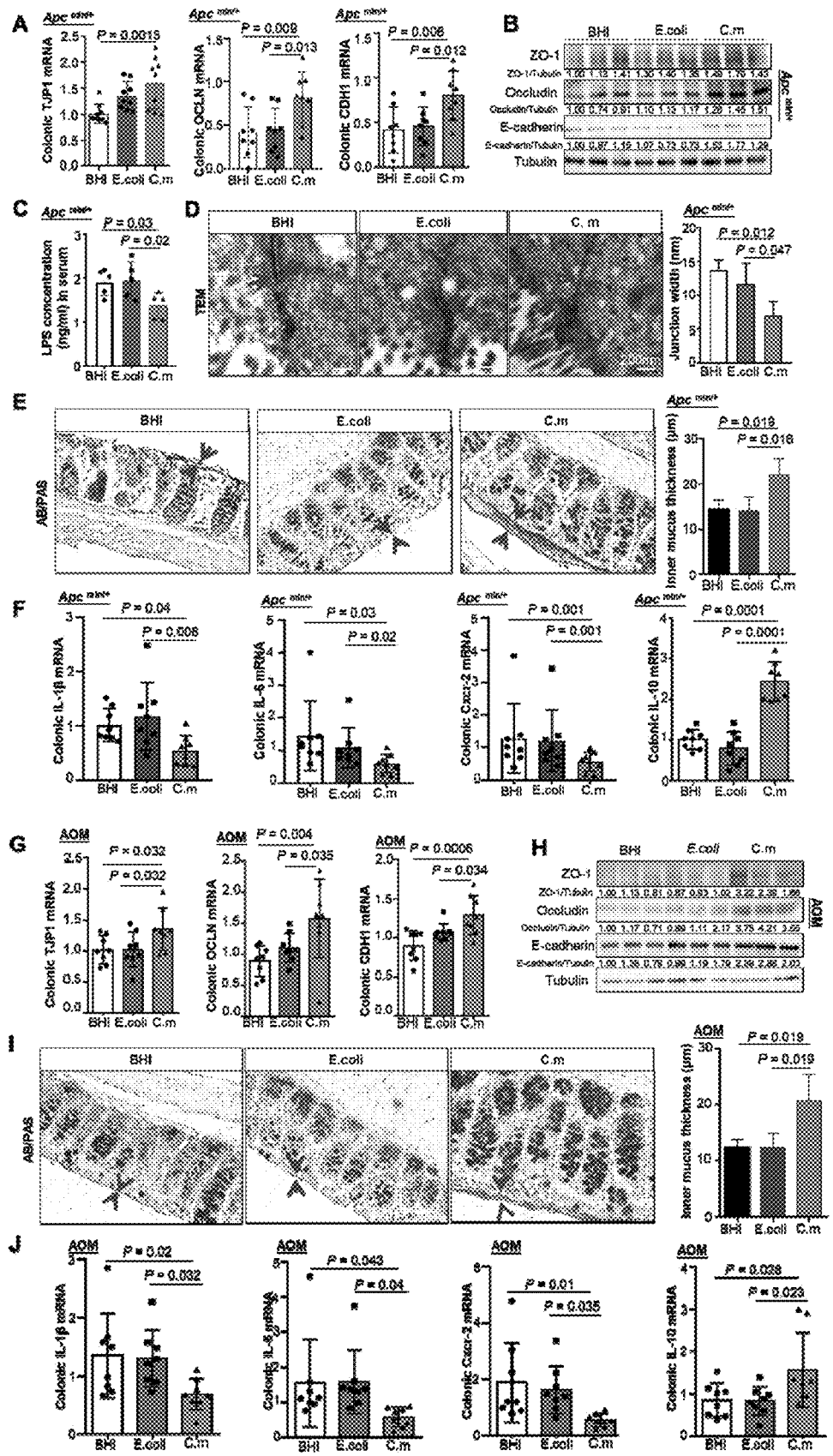
FIG. 5 shows that *C. maltaromaticum* preserves gut barrier function, inhibits pro-inflammatory response in $Apc^{min/+}$ mice and AOM-induced CRC mice. (A) mRNA expression levels of gut barrier-associated genes Tjp1 (ZO-1), Ocln, and Cdh1 in colon tissues of $Apc^{min/+}$ mice under different treatments. (B) Expression levels of gut barrier-associated proteins ZO-1, Occludin, and E-cadherin in colon tissues of $Apc^{min/+}$ mice. (C) LPS concentrations in serum of $Apc^{min/+}$ mice. (D) Representative ultrastructure images of colonic intercellular junctions of $Apc^{min/+}$ mice. (E) Representative AB-PAS-stained inner mucus layer images from $Apc^{min/+}$ mice. (F) mRNA expression levels of pro-inflammatory genes IL-1β, IL-6, Cxcr-2, and anti-inflammatory cytokine IL-10 in colon tissues of $Apc^{min/+}$ mice. (G) mRNA expression levels of gut barrier associated genes Tjp1 (ZO-1), Ocln, and Cdh1 in colon tissues of AOM-induced CRC mice under different treatments. (H) Expression levels of gut barrier-associated proteins ZO-1, Occludin, and E-cadherin in colon tissues of AOM-induced CRC mice. (I) Representative AB-PAS-stained inner mucus layer images from AOM-induced CRC. (J) mRNA expression levels of pro-inflammatory genes IL-1β, IL-6, Cxcr-2, and anti-inflammatory cytokine IL-10 in colon tissues of AOM-induced CRC mice. Results are presented as mean±S.D. Statistical significance was determined by one-way ANOVA. C.m, *C. maltaromaticum*; AOM, azoxymethane.

C. maltaromaticum Preserves Gut Barrier Function and Inhibits Pro-Inflammatory Response in Murine Models of CRC Gut barrier dysfunction and its related inflammatory response are known to be associated with the initiation and progression of CRC[3]. To assess the involvement of C. maltaromaticum in modulating gut barrier function, the mRNA and protein expression levels of key tight junction genes and proteins were examined by RT-qPCR and Western blots, respectively. Administration of C. maltaromaticum markedly increased the colonic tight junction regulators, including Tjp1 (ZO-1), Ocln (Occludin), and Cdh1 (E-cadherin) at mRNA (FIG. 5A) and protein (FIG. 5B) level in Apc$^{min/+}$ mice. The leakage of gut bacterial lipopolysaccharides (LPS) into the systemic circulation was then measured for inferring the gut barrier function. It was discovered that Apc$^{min/+}$ mice gavaged with *C. maltaromaticum* had a significantly lower serum level of LPS (FIG. 5C). Visualization of cell-cell junctions with TEM further indicated that *C. maltaromaticum* could shorten the junction width (FIG. 5D). In keeping with this, the thickness of the inner mucus layer stained by AB-PAS confirmed the increased thickness of the mucus-containing layer in *C. maltaromaticum*-treated Apc$^{min/+}$ mice (FIG. 5E). To examine the role of *C. maltaromaticum* in modulating the inflammatory response, the soluble factors' expression level in colonic tissues was measured. As compared with BHI and *E. coli* strain MG1655 treatment mice, administration of *C. maltaromaticum* significantly attenuated the expression of key pro-inflammatory genes, including interleukin (IL)-1β, IL-6, and CXC chemokine receptor 2 (Cxcr-2). The anti-inflammatory cytokine IL-10, on the contrary, was markedly increased (FIG. 5F). Consistently, the increased expression of genes encoding tight junction proteins (FIG. 5G-5H), thickened mucus layer (FIG. 5I), and reduced pro-inflammatory response (FIG. 5J) by *C. maltaromaticum* was observed in AOM-induced CRC model, confirming *C. maltaromaticum* could preserve the gut barrier function in CRC mice, indicating *C. maltaromaticum* could reduce the pro-inflammatory response in CRC mice.

*C. maltaromaticum* Modulates Gut Microbiota in Apc$^{min/+}$ Mice

To determine the effects of *C. maltaromaticum* inoculation on gut microbiota composition, 16S rRNA gene sequencing with Apc$^{min/+}$ mouse fecal samples was performed. Daily administration *C. maltaromaticum* caused a distinct trend on β-diversity as revealed by Principal Coordinate Analysis (PCoA) (FIG. 6A). Bacteria genera of Desulfovibrionaceae and Rikenellaceae were significantly enriched in *C. maltaromaticum*-gavaged mice as compared with both BHI and *E. coli* strain MG1655 (FIG. 6B). The abundance of some well-characterized commensal probiotics including *Bifidobacterium*, butyrate producing Rosebutia, and Clostridiales were significantly increased in the *C. maltaromaticum*-treated mice. In contrast, certain pathogenic species, including Candidatus Arthromitus, *Prevotella*, *Coprococcus*, and *Dorea*, exhibited significantly decreased abundance in *C. maltaromaticum*-gavaged mice (FIG. 6C), suggesting that the modulatory effect of *C. maltaromaticum* on the gut microbiota is associated with its CRC-preventive effect.

Figure 7A:
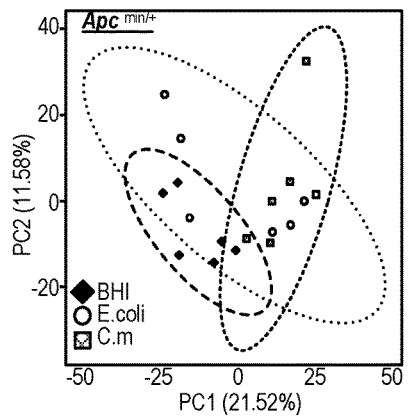
FIG. 7 shows that *C. maltaromaticum* increases the abundance of vitamin D metabolites in the gut of $Apc^{min/+}$ mice and AOM-induced CRC mice. (A) Principal coordinate analysis (PCoA) for gut metabolomic alteration in $Apc^{min/+}$ mice under different treatments. (B) Heatmap representation of differentially metabolites in $Apc^{min/+}$ mice. (C) Pathway analysis of differentially enriched metabolic pathways in $Apc^{min/+}$ mice. (D) Colonic mucosa 1α,25-dihydroxyvitamin D3 (1,25(OH)$_2$D$_3$) concentration in $Apc^{min/+}$ mice. (E) Levels of enzymes (CYP2R1, CYP27A1, and CYP27b1) responsible for 1,25(OH)$_2$D$_3$ biosynthesis in colon tissues of $Apc^{min/+}$ mice. (F) Heatmap representation of enhanced vitamin D metabolites in AOM-induced CRC mice under different treatments. (G) Colonic mucosa 1,25(OH)$_2$D$_3$ concentration in AOM-induced CRC mice. (H) Levels of enzymes (CYP2R1, CYP27A1, and CYP27b1) responsible 1,25(OH)$_2$D$_3$ biosynthesis in colon tissues of AOM-induced CRC mice. Results are presented as mean±S.D. Statistical significance was determined by one-way ANOVA. C.m, *C. maltaromaticum*; AOM, azoxymethane.
Figure 7B:
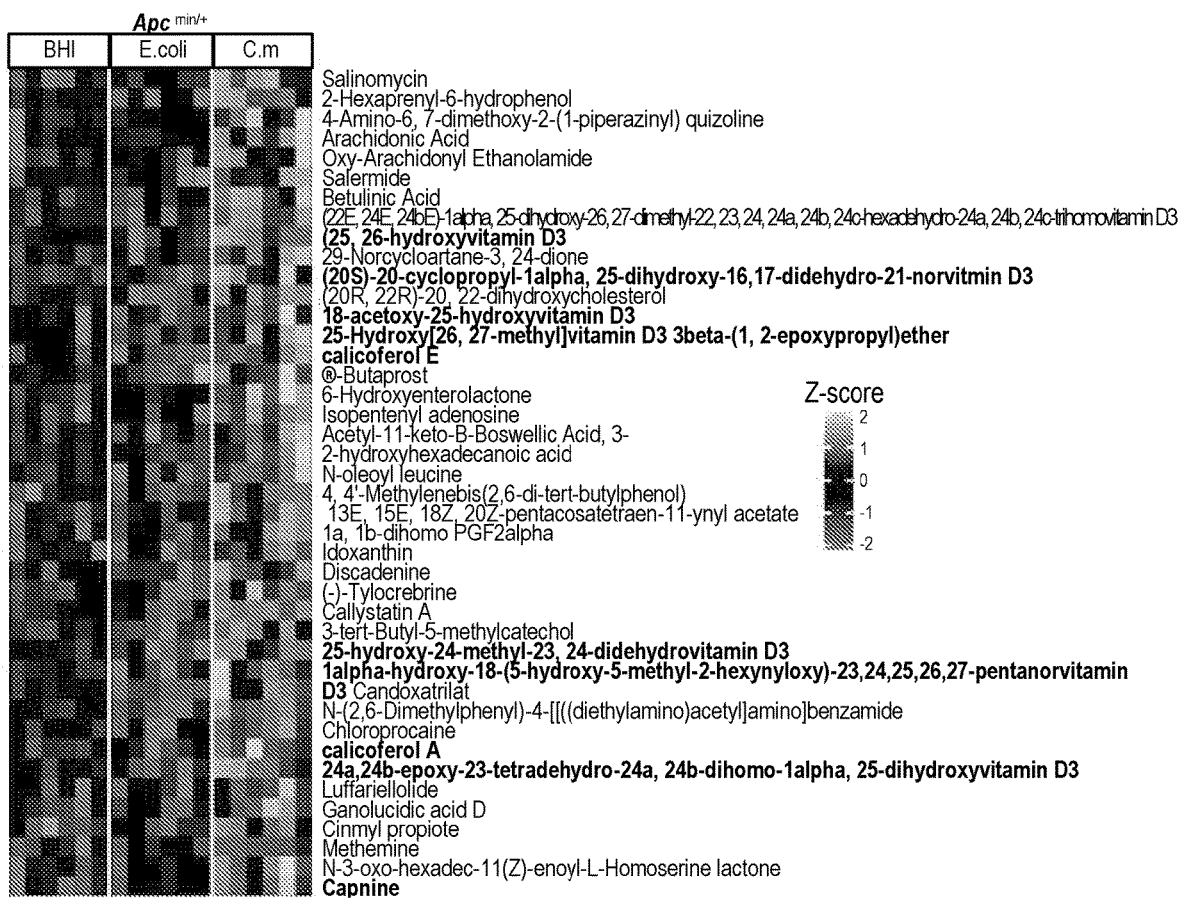
Figure 7D:
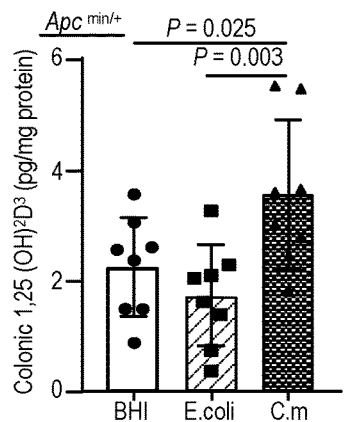
Figure 7E:
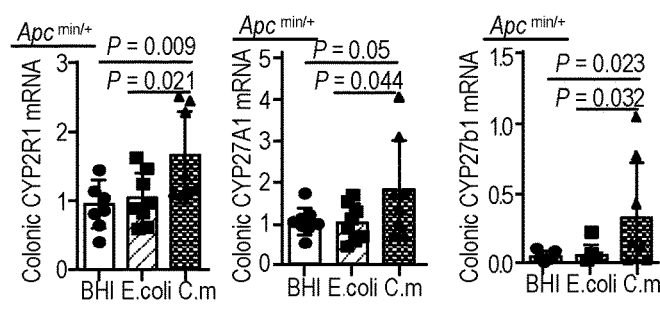
Figure 7F:
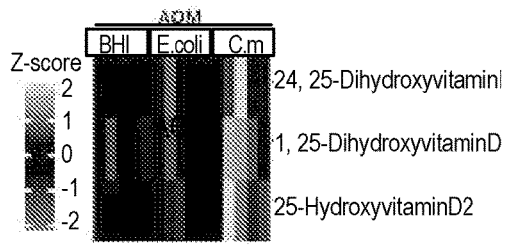
Figure 7G:
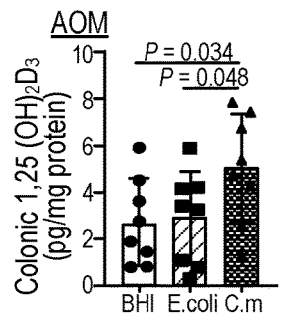
Figure 7H:
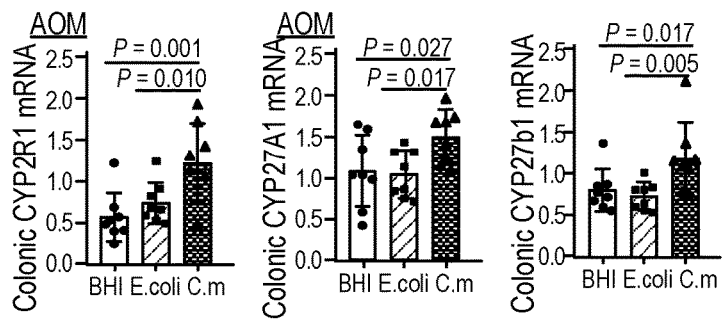

*C. maltaromaticum* Increases the Abundance of Vitamin D Metabolites in Mouse Models of CRC To determine whether *C. maltaromaticum* could exert any effect on the metabolome, the fecal metabolites from *C. maltaromaticum*-treated Apc$^{min/+}$ mice were profiled by LC-MS/MS. A significant overall compositional alteration of the gut metabolites was observed among the *C. maltaromaticum* and control groups in the Apc$^{min/+}$ mouse model (FIG. 7A). Forty-two metabolites were found to be enriched in the *C. maltaromaticum*-treated Apc$^{min/+}$ mice as compared with both BHI- and *E. coli* strain MG1655-treated groups (FIG. 7B). Most of these metabolites, such as 29-nor-cycloartane-3,24-dione, 4,4'-methylenebis(2,6-di-tert-butylphenol), 3-tert-butyl-5-methylcatechol, (−)-tylocrebrine, betulinic acid and cinmyl propiote have been reported to have anti-inflammatory/anti-cancer effect. In particular, enrichment of a repertoir of vitamin D metabolites was observed in the fecal samples of *C. maltaromaticum*-treated mice. Further metabolic pathway enrichment analysis revealed the significant alteration of fecal vitamin $D_3$ metabolism in *C. maltaromaticum*-treated Apc$^{min/+}$ mice as compared with both control groups (FIG. 7C). 1,25(OH)$_2$D$_3$ is the active form of vitamin $D_3$ and plays an important role in cancer prevention and treatment[14]. The accumulation of considerable amounts of 1,25(OH)$_2$D$_3$ in colonocytes could reach levels that would locally induce growth inhibitory on CRC cells[15]. As intracellular concentrations of 1,25(OH)$_2$D$_3$ could drive the biological effect of vitamin D in cell growth regulation, the colonic concentration of 1,25(OH)$_2$D$_3$ in Apc$^{min/+}$ mice after *C. maltaromaticum* treatment was further examined. As shown in FIG. 7D, *C. maltaromaticum* significantly increased the colonic 1,25(OH)$_2$D$_3$ concentration. The enzymes (CYP2R1, CYP27A1, and CYP27B1) responsible for the biosynthesis of 1,25(OH)$_2$D$_3$ were also upregulated in the colon tissues of Apc$^{min/+}$ mice receiving *C. maltaromaticum* (FIG. 7E), suggesting the potential contribution of vitamin D metabolism in mediating the CRC-suppressive effect of *C. maltaromaticum*. To further validate this observation, the fecal metabolic changes were profiled using the stool samples from AOM-induced CRC model. Consistently, vitamin D metabolites, especially the active form 1,25(OH)$_2$D$_3$, was found to be increased significantly in the fecal samples of *C. maltaromaticum*-treated, AOM-induced CRC mice (FIG. 7F). The colonic 1,25(OH)$_2$D$_3$ level (FIG. 7G) and the enzymes responsible for 1,25(OH)$_2$D$_3$ biosynthesis (FIG. 7H) were also significantly increased after *C. maltaromaticum* treatment. These results indicate that *C. maltaromaticum* administration increased the fecal abundance of vitamin D-related metabolites, which were activated by the colonocytes' enzymes to induce the local accumulation of 1,25(OH)$_2$D$_3$ in mouse models of CRC.

Figure 8A:
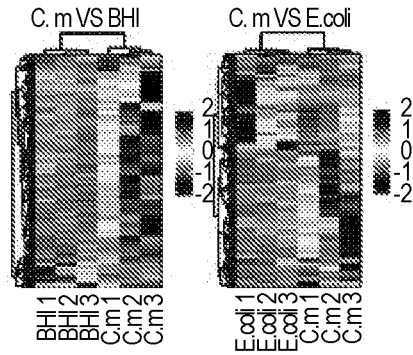
FIG. 8 shows that *C. maltaromaticum* induces vitamin D signaling in $Apc^{min/+}$ mice. (A) Heatmap representation of differentially expressed genes in colonic tissues of $Apc^{min/+}$ mice under different treatments. (B) mRNA expression levels of bile acid receptors in colon tissues of $Apc^{min/+}$ mice. (C) Gene Set Enrichment Analysis (GSEA) of differentially expressed gene in $Apc^{min/+}$ mice. (D) mRNA (left panel) and protein expression level (right panel) of VDR in colon tissues of $Apc^{min/+}$ mice. (E) mRNA expression level of CRAMP, a VDR target gene, in colon tissues of $Apc^{min/+}$ mice. (F) Immunofluorescence staining of nuclear VDR$^+$ cells in $Apc^{min/+}$ mice colons with quantitative analysis of MFI. (G) mRNA expression level of VDR in TCGA COAD tumor samples. (H) Heatmap representation of expression of VDR target genes in $Apc^{min/+}$ mice. Results are presented as mean±S.D. Statistical significance was determined by one-way ANOVA. MFI, mean fluorescence intensity; C.m, *C. maltaromaticum*.
Figure 8C:
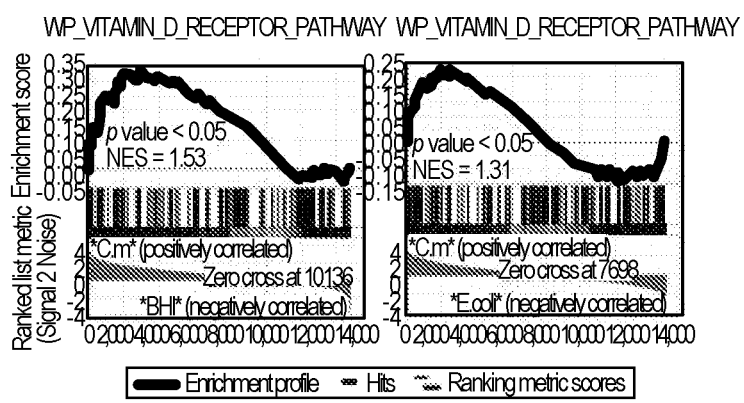
Figure 8B:
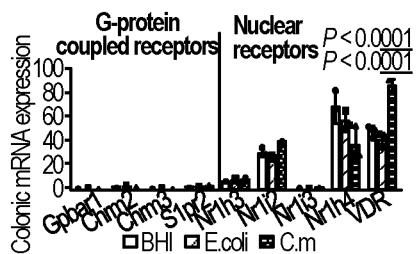
Figure 8D:
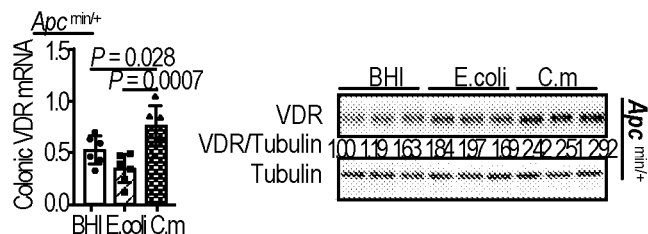
Figure 8E:
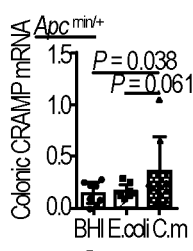
Figure 8F:
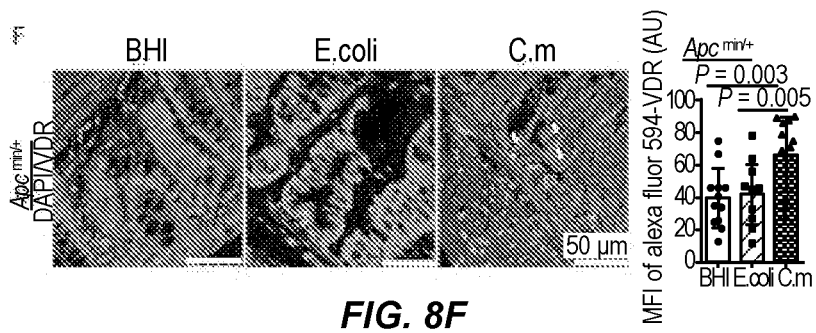
Figure 8G:
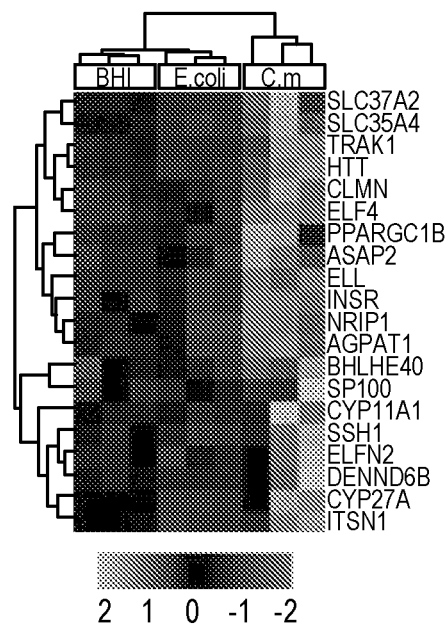
Figure 8H:
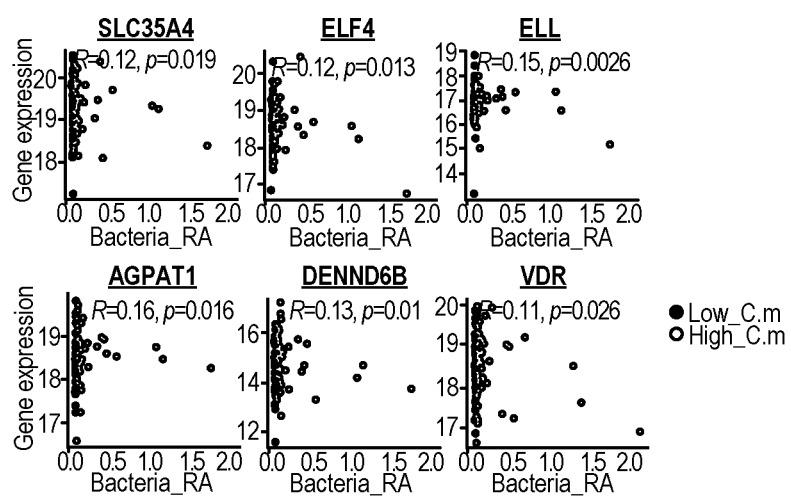
Figure 9:
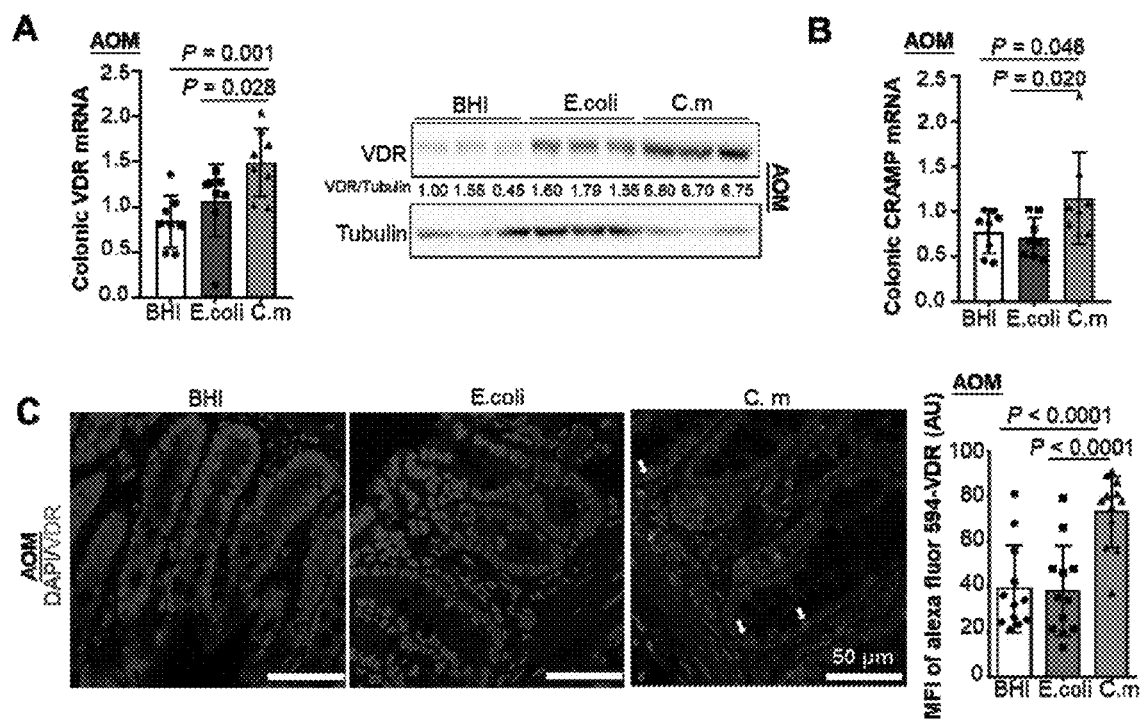
FIG. 9 shows that *C. maltaromaticum* induces vitamin D signaling in AOM-induced CRC mice. (A) mRNA (left panel) and protein expression level (right panel) of VDR in colon tissues of AOM-induced CRC mice. (B) mRNA expression level of CRAMP in colon tissues of AOM-induced CRC mice. (C) Immunofluorescence staining of nuclear VDR$^+$ cells in AOM-induced CRC mice colons with quantitative analysis of MFI. Results are presented as mean±S.D. Statistical significance was determined by one-way ANOVA. MFI, mean fluorescence intensity; C.m, *C. maltaromaticum*; AOM, azoxymethane.

*C. maltaromaticum* Induces Colonic Vitamin D Receptor Activity in Mouse Models of CRC 1,25 (OH)$_2$D$_3$ is synthesized and degraded in colonocytes and, when bound to its receptor, has antiproliferative activity[15]. To investigate the transcriptional activation of vitamin D receptor (VDR) by *C. maltaromaticum*, transcriptome-sequencing was performed in colon tissues from Apc$^{min/+}$ mice under different treatments (FIG. 8A). It was discovered that VDR was the only changed bile acid receptor, which was significantly upregulated in the *C. maltaromaticum*-treated Apc$^{min/+}$ mice colon as compared with both BHI- and *E. coli* strain MG1655-treated groups (FIG. 8B). Concordantly, gene set enrichment analysis (GSEA) of transcriptome profiles revealed that VDR signaling was significantly enriched in the colonic tissues of *C. maltaromaticum*-treated Apc$^{min/+}$ mice compared with both control groups (FIG. 8C). The upregulation of VDR was further validated at mRNA and protein levels in *C. maltaromaticum*-treated Apc$^{min/+}$ mice (FIG. 8D). The activated VDR was then confirmed by increased level of CRAMP (FIG. 8E), a well-known VDR target gene[8], and the nuclear translocation of VDR in colonic tissues of *C. maltaromaticum*-treated Apc$^{min/+}$ mice (FIG. 8F). This finding was further validated in TCGA cohort, which showed that CRC patients with higher abundance of *C. maltaromaticum* exhibited higher level of VDR (FIG. 8H). Accordingly, 20 VDR target genes were upregulated in the *C. maltaromaticum*-treated Apc$^{min/+}$ mice as revealed by transcriptome-sequencing (FIG. 8G). Five of them (SLC35A4, ELF4, ELL, AGPAT1 and DENND6B) were significantly correlated with *C. maltaromaticum* abundance in TCGA dataset (FIG. 8H), indicating that *C. maltaromaticum* increases the colonic 1,25(OH)$_2$D$_3$ level to induce the activation of VDR in Apc$^{min/+}$ mice. The activation of VDR was further validated in the AOM-induced CRC model. Consistent results were observed as in the Apc$^{min/+}$ mice that *C. maltaromaticum* administration increased VDR (FIG. 9A) and its target gene (CRAMP) (FIG. 9B) expression in colonic tissues and induced VDR translocation into the nucleus (FIG. 9C). Taken together, these data indicate that the tumor-suppressive effect of *C. maltaromaticum* is associated with increased vitamin D metabolites and the activation of VDR signaling.

Discussion

In the present study, the present inventors confirmed that *C. maltaromaticum* was depleted in CRC patients and was a potential marker for predicting the survival of CRC patients. Co-incubation of *C. maltaromaticum* with colon cells significantly suppressed the proliferation and induced cell cycle arrest in CRC cells but not in the normal colonic epithelial cells. Oral administration of *C. maltaromaticum* retarded the intestinal tumorigenesis in two murine CRC animal models, supporting the anti-CRC efficacy of *C. maltaromaticum*.

Figure 10:
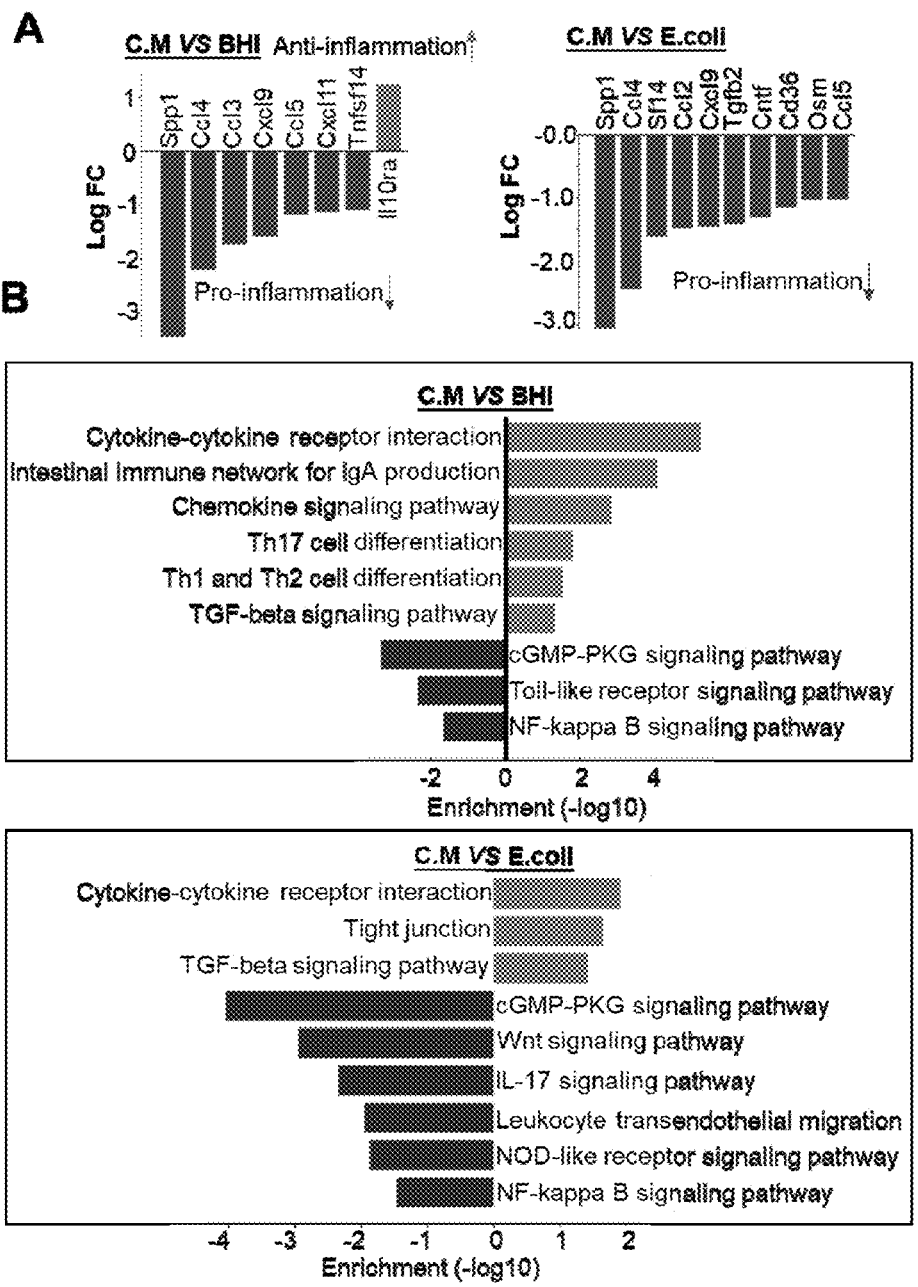
FIG. 10 shows that *C. maltaromaticum* inhibits pro-inflammatory response in $Apc^{min/+}$ mice. (A) Expression of multiple inflammation-related genes in colon tissues of $Apc^{min/+}$ mice under different treatments. (B) Enrichment of multiple inflammation-related pathways in colon tissues of $Apc^{min/+}$ mice. Results are presented as mean±S.D. Statistical differentially significance gene expression was determined as Cutoff=|Log 2(FC)|>1 & FDR<0.05. C.m, *C. maltaromaticum*.

Dysfunction of mucosal barrier function has been a common feature of CRC. A leaky gut results in uncontrolled translocation of commensal pathogens and antigens into the body[16]. In this study, *C. maltaromaticum* was found to restore gut barrier function through increasing the expression of a number of gut barrier-associated markers, including ZO-1, Occludin, and E-cadherin in mouse CRC models; enhancing the thickness of the colonic inner mucus layer (a physical barrier), along with decreasing paracellular gap and serum LPS level in *C. maltaromaticum*-treated mice. A healthy barrier function is the premise of gut homeostasis[17]. Any disruption or even slight break of the barrier can trigger inflammation[3]. Consistently, the pro-inflammatory genes of IL-1β, IL-6, and Cxcr-2 were significantly decreased, while the anti-inflammatory cytokine IL-10 increased by *C. maltaromaticum* treatment in both mouse models. The reduced expression of pro-inflammatory cytokines (Spp1, Ccl4, Cxcl9, and Ccl5) and the downregulated NF-kappa B signaling, which have been implicated in inflammation and carcinogenesis[18], were also observed in the *C. maltaromaticum* treatment group in the RNA sequencing data (FIG. 10), indicating the involvement of *C. maltaromaticum* in suppressing the pro-inflammatory signaling pathway. It is therefore biologically plausible that the tumor-suppressive effect of *C. maltaromaticum* is associated with preserved gut barrier function and reduced inflammation.

Gut microbiota dysbiosis contributes to the development of CRC[1,19]. The microbes profiling revealed that administration of *C. maltaromaticum* significantly enriched the abundance of well-characterized probiotics, such as Desulfovibrionaceae, which is known to reduce hydrogen sulphide production[20]. The Rikenellaceae, which is inversely associated with pro-inflammatory cytokines and positively correlated with gut barrier protein expression[21], also increased at the genus level. Also, the *Bifidobacterium*, butyrate-producing Rosebutia, Ruminococcaceae and Clostridiales were increased in abundance in *C. maltaromaticum*-gavaged Apc$^{min/+}$ mice. On the other hand, some pathogenic species, including Candidatus Arthromitus[22], *Prevotella*[23], *Coprococcus*[24], and *Dorea*[25], which could trigger excessive inflammation and promote cancer progression, were significantly depleted after *C. maltaromaticum* treatment. Thus, *C. maltaromaticum* protects against CRC at least in part through restoring gut microbiota homeostasis by enhancing the colonization of probiotics and depleting the potential CRC-associated pathogens.

The effect of *C. maltaromaticum* in modulating gut metabolomics was further examined through metabolomic profiling of mouse fecal samples. It was discovered that inoculation of *C. maltaromaticum* to both murine models increased the level of a repertoire of vitamin D metabolites. Vitamin D supplementation has been viewed as a potential strategy for CRC prevention[26]. Vitamin D deficiency is associated with increased risks for CRC[27]. Moreover, the enzymes responsible for extrarenal production of 1,25(OH)$_2$D$_3$, including CYP2R1, CYP27A1 and CYP27B1 were induced by *C. maltaromaticum*. Colonic 1,25 (OH)$_2$D$_3$, which is responsible for most of the biological actions of vitamin D, was increased significantly after *C. maltaromaticum* consumption, presenting the possibility that *C. maltaromaticum* inhibits intestinal tumorigenesis via increasing the mucosal concentration of 1,25(OH)$_2$D$_3$. Indeed, polymorphism of CYP27B1, the enzyme for the biosynthesis of 1,25 (OH)$_2$D$_3$, dictates the risk of CRC[28].

VDR is a transcription factor, which is involved in a wide variety of biological processes, including regulation of cell proliferation and differentiation in normal tissue and apoptosis in tumor cells[29]. In CRC, the VDR has been reported to inhibits tumor initiation and promotion via the regulation of p21, p27, and E-cadherin[30]. 1,25(OH)$_2$D$_3$, the active form of vitamin D$_3$, mediates cellular functions via VDR[31]. Concordantly, it was discovered that the VDR signaling was upregulated significantly in Apc$^{min/+}$ mice after treatment with *C. maltaromaticum*. This observation therefore supports the notion that *C. maltaromaticum* elevates the level of 1,25 (OH)$_2$D$_3$ in colon tissues, thereby activating VDR receptor to induce the downstream anti-CRC signaling.

In summary, this study uncovers the anti-CRC effect of *C. maltaromaticum*. The intestinal tumor-suppressive role of *C. maltaromaticum* is associated with the modulated gut microbiota and metabolites together with the preserved gut barrier function and reduced mucosal inflammation. Especially, such action is associated with the induction of vitamin D-related metabolites and the activation of VDR. Taken together, *C. maltaromaticum* can be used as a novel probiotic-based prophylactics for CRC prevention.

Example II: *Lactobacillus gallinarum* Modulates the Gut Microbiota and Produces Anti-Cancer Metabolites to Protec Against Colorectal Tumorigenesis Background of the Invention Colorectal cancer (CRC) is the third most commonly diagnosed malignancy and the second leading cause of cancer death in the world[32]. There are many risk factors associated with CRC carcinogenesis including genetic alterations, lifestyle and environmental factors[33]. Over the last decade, gut microbiota has been shown to play a key role in CRC development. Certain probiotic bacteria such as *Streptococcus thermophilus* and *Lactobacillus rhamnosus* have anti-carcinogenic properties[34,35].

Most *Lactobacillus* species are classified as lactic acid bacteria (LAB). LAB are generally found in fermented food, such as decomposing plants and milk products, and they are widely accepted to be used as probiotics for humans[36]. The beneficial effects of LAB for diseases have been reported extensively[37,38], and preclinical studies have shown its abilities to reduce chronic inflammation associated with cancer development[39,40]. Using shotgun metagenomic sequencing, the present inventors identified a probiotic species *Lactobacillus gallinarum* being significantly depleted in the stool of CRC patients[13], suggesting that it might play a role in suppressing CRC. In this study, *L. gallinarum* was shown to abrogate colorectal tumorigenesis in mouse models, human CRC-derived organoids and CRC cell lines through promoting apoptosis. This tumor-suppressing effect was attributed to indole-3-lactic acid, a metabolite produced by *L. gallinarum*.

Materials and Methods

Animal Experiments

Male Apc$^{Min/+}$ C57B/6 transgenic mice was used as a mouse model of spontaneous CRC'. Apc$^{Min/+}$ mice at 5 to 6 weeks old were divided into 3 groups with or without CH-223191 treatment: (1) control; (2) *E. coli* MG1655; and (3) *L. gallinarum*. *L. gallinarum* and *E. coli* MG1655 were cultured in MRS® broth (Difco Laboratories, Detroit, MN) and BHI broth, respectively. After one day, $1.0 \times 10^8$ colony-forming units (CFUs) bacteria were collected and resuspended in 100 ul PBS. Mice were gavaged once daily for 8 weeks and body weight and stool were examined weekly.

For the azoxymethane (AOM)/dextran sulfate sodium (DSS) model, male C57BL/6 mice at 6 weeks old were intraperitoneally injected with a single dose of 10 mg/kg AOM (Merck, Darmstadt, Germany), followed by 2% DSS (MP Biomedicals, Solon, OH) administration for 1 week. AOM/DSS-induced CRC mice were gavaged with the above *L. gallinarium* and *E. coli* MG1655 suspension following the same schedule.

Mouse colonoscopy (Karl Storz Endoskope, Tuttlingen, Germany) was performed prior to sacrifice. The colonoscope was inserted into the anus and advanced proximally under direct visualization, facilitated by air insufflation, and representative pictures of the colon tumor from each group were recorded. After 8 weeks of gavage, mice were anaesthetized and sacrificed. Small intestines and colons of mice were longitudinally opened and rinsed with PBS. Total number of tumors in small intestine and colon were recorded. Size of each tumor was measured using previous published formula[42]. All animal studies were performed in accordance with guidelines approved by the Animal Experimentation Ethics Committee of The Chinese University of Hong Kong.

DNA Extraction, 16S Ribosomal DNA Gene Amplification, from ApcMin/+ Mouse Stool Samples after Gavage of *L. gallinarium*

Apc$^{Min/+}$ mouse stool samples were disrupted by bead-beating after digesting with mutanolysin (10 U/ul, Sigma-Aldrich) and lysozyme enzyme cocktail, as described in our previous study[7]. DNA extraction and purification were performed using DNEASY® POWERSOIL™ kit (Qiagen, Hilden, Germany). Amplicon library for bidirectional (466 bp) sequencing on ILLUMINA® MISEQ™ platform was constructed using universal primers 341f (SEQ ID NO:3), 5'-CCTAYGGGRBGCASCAG-3' and 806r (SEQ ID NO:4), 5'-GGACTACNNGGGTATCTAAT-3' targeting across 16S rRNA genes V3-V4 hypervariable regions. Library clean-up and normalization was performed using the NEB® NEXT ULTRA™ DNA Library Pre kit (New England Biolabs, Ipswich, MA).

16S rRNA Gene Sequence Analysis

Raw de-multiplexed FASTQ files were preprocessed in Mothur[43]. Contigs were created using Needleman-Wunsch alignment algorithm with default parameters[44], and aligned against the SILVA database (version 123) using the NAST algorithm[45,46]. Any contigs with homopolymers of greater than 8 nucleotides were removed and all that mapped within the identical coordinates were retained. Any sequence pairs with mismatch difference of ≤2 were preclustered to reduce amplicon sequencing noises. Chimeric sequences were culled using de novo UChime[47]. Post-quality controlled sequences were classified using Greengenes 16S rRNA database (13.8). Any sequences of eukaryotic, archaea, mitochondrial, chloroplastic, or unknown origins were discarded before being binned into operational taxonomic units (OTUs) at 97% identity threshold. The lowest taxonomic annotation for an OTU was defined as having a consensus assignment score of ≥80. Sequence count table was rarefied to the smallest number of reads per sample (i.e., 44,845 reads) to reduce the effects of variable sequencing depths on downstream analyses. Differential abundance analysis was performed with one way analysis of variance. Average fold change for each OTU and heatmap was computed in the R Project for Statistical Computing[48].

Bacterial Strains and Culture Conditions

*L. gallinarum* (ATCC 33199) was purchased from American Type Culture Collection (ATCC; Manassas, VA). *Escherichia coli* (*E. coli*) strain MG1655 (ATCC 700926), a non-pathogenic human commensal intestinal bacterium, was included as a negative control[49]. *L. gallinarum* and *E. coli* MG1655 were cultured in MRS broth (Difco Laboratories, Detroit, MN) and BHI broth, respectively, at 37° C. under aerobic condition. The bacteria were centrifuged at 5,000 rpm for 10 minutes to obtain the bacteria pallet and resuspended in BHI before gavaging to mice.

Culture Supernatant of *L. gallinarum*

After culturing *L. gallinarum* or *E. coli* MG1655 for 1-2 days, the bacterial concentration in each culture medium was measured using NanoDrop spectrophotometer (NanoDrop Technologies, Wilmington, DE). BHI cultures were diluted to ensure equal concentrations of *L. gallinarum* and *E. coli*. Culture supernatants were then collected by centrifugation at 5,000 rpm for 10 minutes, followed by sterile filtration with a 0.22-μm membrane. Filtrates were collected and termed as *L. gallinarum* culture supernatant (LGCS) or *E. coli* MG1655 culture supernatant (ECCS).

Bacterial culture supernatant was separated into low-molecular-weight (LMW) and high-molecular-weight (HMW) using Amicon Ultra-15 Centrifugal Filter Units with a pore size of 3 kilodalton (kDa, Millipore, Bedford, MA). After centrifugation in a swinging bucket rotor at 4,000 g for 30 minutes, cells were cultured in medium containing LGCS, ECCS or control broth (LMW, 10%; HMW, 1%). The bacterial supernatants were heated at 100° C. for 30 minutes or treated with proteinase k (50 ug/ml; QIAGEN GmbH, Hilden, Germany). 10% heat-inactivated or proteinase k-treated bacterial culture supernatant was used for MTT assay.

Cell Culture

Colon cancer cell lines, HCT116 and LoVo, were purchased from ATCC. A normal colonic epithelial cell line, NCM460, was obtained from INCELL Corporation (San Antonio, TX) as control. All cells were grown in high-glucose Dulbecco's Modified Eagle's Medium (DMEM) (Thermo Fisher Scientific) supplemented with 10% fetal bovine serum (FBS) (Thermo Fisher Scientific), 2 mM L-glutamine, 50 U/ml penicillin and 50 μg/ml streptomycin in a humidified atmosphere containing 5% $CO_2$.

CRC Patient-Derived Organoid Culture

CRC organoids derived from 2 patients (74 and 816) were obtained from Princess Margaret Living Biobank (Toronto, Ontario, Canada), and embedded in Matrigel (Corning Inc, Corning, NY). Culture medium was changed every 2 days. After 5 days of culture, Matrigel was removed to expose organoids by mechanical stress and/or TrypLE digestion (Sigma-Aldrich). Organoids were then collected for further experiments.

Cell Viability Assay

Cell viability was measured by 3-(4,5-dimethylthiazoly-2-yl)-2,5-diphenylte-trazolium bromide (MTT, Sigma-Aldrich) assay. Cells were seeded on 96-well plates at $5.0\times10^2$, $1.0\times10^3$ and $3.0\times10^3$ cells per well and incubated for 24 hours before treatment. Cells were cultured in DMEM with addition of bacterial supernatants at different concentrations (5%, 10%, or 20%) or bacteria alone (multiplicities of infections: MOIs 50, 100). For bacterial co-culture treatment, the medium was replaced with DMEM supplemented with 10% FBS, 1% penicillin-streptomycin and 20 $\mu$gml$^{-1}$ gentamycin after 2 hours of co-culture under aerobic conditions before MTT assay. Cell proliferation was measured by MTT assay for 5 consecutive days. The amount of MTT formazan product was determined by measuring absorbance at a wavelength of 570 nm (OD570) with a microplate reader (Multiskan GO Microplate Spectrophotometer, Thermo Scientific, Vantaa, Finland). For pharmacological inhibition of aryl hydrocarbon receptor (AhR), CH-223191 (100 nM) was added 12 hours before the treatment with bacteria culture supernatant.

Colony Formation Assay

Cells were seeded overnight on 12-well microplates at $5.0\times10^2$, $1.0\times10^3$ and $3.0\times10^3$ cells per well. 20% of LGCS, ECCS or BHI broth was then added to the medium and cultured for 14 to 21 days. Cells were washed with phosphate-buffered saline (PBS) and fixed in methanol, prior to staining with 0.5% crystal violet. Colonies were counted manually and relative colony formation was calculated using formula: relative colony formation (%)=(number of colony formed/average colony number in control group)×100%.

Apoptosis Assay and Cell Cycle Analysis

Cells were plated on 6-well plates 24 hours prior to treatment, and cultured in medium containing 10% LGCS, ECCS or control broth. CRC patient-derived organoids were cultured on 6-well plates, and 10% LGCS, ECCS or control broth was added to Matrigel and growth medium. After treatment, cells and organoids were digested in 0.25% trypsin-EDTA (Gibco-Invitrogen Corp., Grand Island, NY) and TrypLE, respectively. For apoptosis assay, the proportion of apoptotic cells was evaluated by dual staining with Annexin V-PE and 7-Aminoactinomycin D (7-AAD) (BD Pharmingen, San Jose, CA). Combination of Annexin V-PE and 7-AAD staining distinguished early apoptotic cells (Annexin V+, 7-AAD−) and late apoptotic cells (Annexin V+, 7-AAD+). For cell cycle analysis, cells treated with 10% LGCS, ECCS or control broth for 1 day were fixed and stained with 50 $\mu$g/ml propidium iodide (PI) (BD Pharmingen). Cell cycle of all stained cells were analyzed using FASAria cell sorter (BD Biosciences, San Jose, CA).

Liquid Chromatography-Tandem Mass Spectrometry (LC-MS/MS) Analysis

Metabonomics was performed by BIOTREE, Shanghai, China, as described in Example I.

High-Throughput Targeted Metabolomics for Tryptophan

Stock solutions were individually prepared by dissolving or diluting each standard substance to give a final concentration of 1 mmol/L. An aliquot of each of the stock solutions was transferred to an Eppendorf tube form a mixed working standard solution. A series of calibration standard solutions were then prepared by stepwise dilution of this mixed standard solution (containing isotopically-labelled internal standard mixture in identical concentrations with the samples). The metabolites form stool and LGCS-LMW were extracted and subjected to UHPLC-MS/MS analysis (BIOTREE, Shanghai, China).

Statistical Analysis

Values are expressed as mean±standard deviation (SD) for both in vivo and in vitro experiments. Comparisons between two groups were performed using a two-sided Student's t-test. ANOVA was used to compare differences among multiple groups, and post-hoc analysis was performed by Tukey's multiple comparisons test. P-values<0.05 indicate statistical significances.

Results

*L. gallinarum* Protects Against Intestinal Tumorigenesis in Apc$^{Min/+}$ Mice

Figure 11:
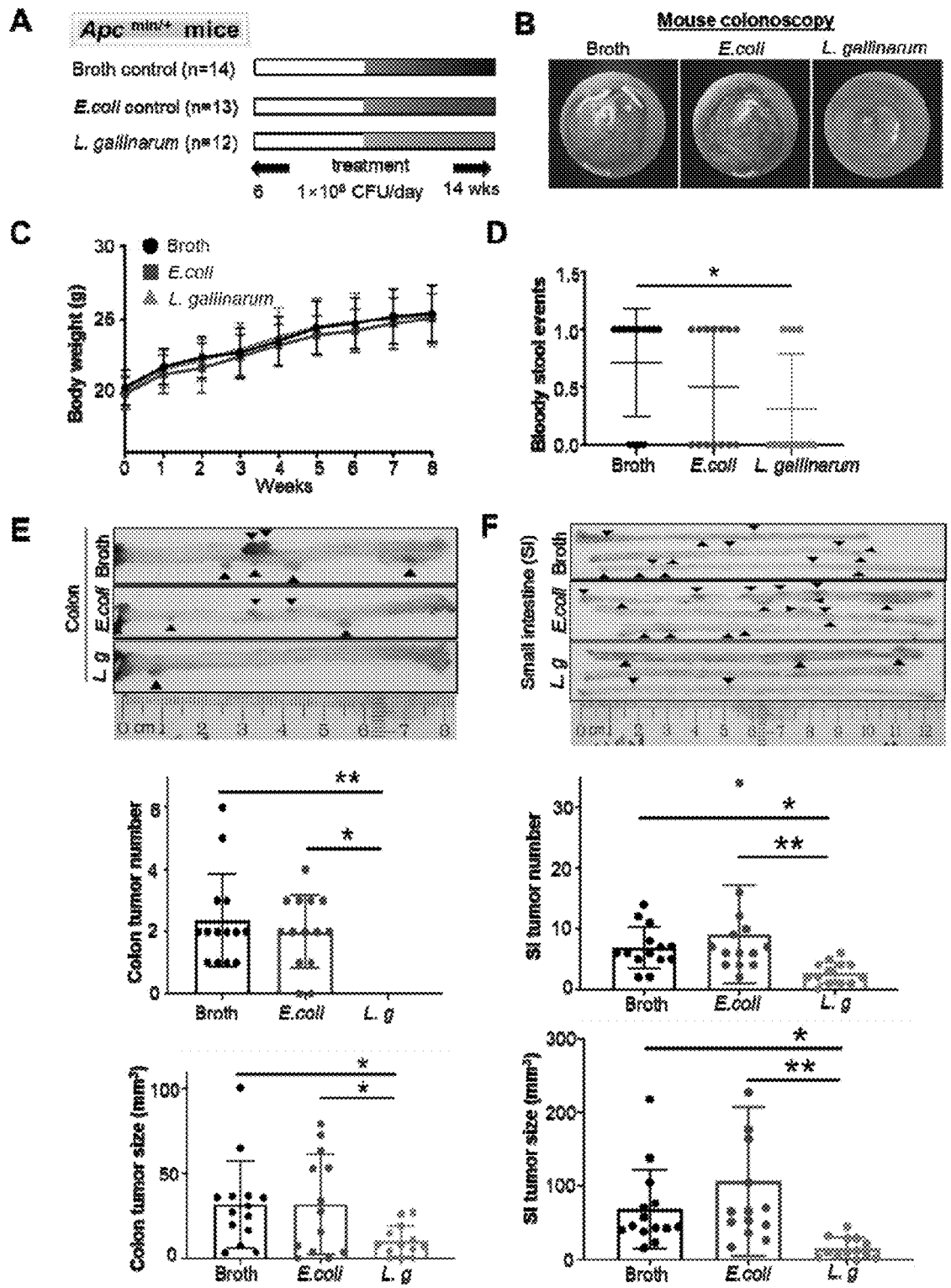
FIG. 11 shows that *L. gallinarum* protects against intestinal tumorigenesis in Apc$^{Min/+}$ mice. (A) Schematic diagram showing the experimental design, timeline of Apc$^{Min/+}$ mouse model. (B) Representative images of colon tumor from Apc$^{Min/+}$ mouse model. Colonoscopy confirmed that colon tumor size in *L. gallinarum* group was visually smaller than tumors in *E. coli* MG1655 or PBS control groups. In both *E. coli* MG1655 and PBS control groups, colonoscope could not pass through the tumors. (C) There was no significant difference in body weight among three groups of mice during the period of gavage. (D) Number and incidence of bloody stool in *L. gallinarum* group were lower than broth control group after gavage for 8 weeks. (E) Colon tumor number and tumor size in Apc$^{Min/+}$ mice under different treatments. (F) Small intestinal tumor number and tumor size in Apc$^{Min/+}$ mice under different treatments. Each black triangle indicates one tumor location. P-values are calculated by one-way ANOVA. *p<0.05, p<0.01, *p<0.001. L.c, *L. casei*; L.g, *L. gallinarum*; SI, small intestine.

To investigate the effect of *L. gallinarum* on colorectal tumorigenesis, Apc$^{Min/+}$ mice were first used. The mice were gavaged with *L. gallinarum* ($1.0\times10^8$ CFUs per mouse), a non-tumorigenic *E. coli* strain MG1655 ($1.0\times10^8$ CFUs per mouse) as bacteria control, or plain culture broth once daily for 8 weeks (FIG. 11A). During the period of gavage, there was no difference in body weight among groups (FIG. 11C). The incidence of bloody stool in *L. gallinarum* group was lower than the Broth control group (p<0.05) after gavage for 8 weeks (FIG. 11C). Colonoscopy identified that colon tumor sizes in *L. gallinarum* group were visually smaller than the *E. coli* MG1655 or broth control groups (FIG. 11B). After sacrifice, significant reductions in tumor number (*E. coli*, p=0.034; broth control, p=0.005) and tumor size (*E. coli*, p<0.05; broth control, p<0.05) were observed in the colon of *L. gallinarum*-treated Apc$^{Min/+}$ mice (FIG. 11 E). *L. gallinarum* also significantly decreased tumor number (*E. coli*, p=0.003; broth control, p<0.05) and tumor size (*E. coli*, p=0.0012; broth control, p<0.05) in the small intestine of Apc$^{Min/+}$ mice (FIG. 11F). These results indicate that *L. gallinarum* abrogates intestinal tumorigenesis in Apc$^{Min/+}$ mice.

Figure 12:
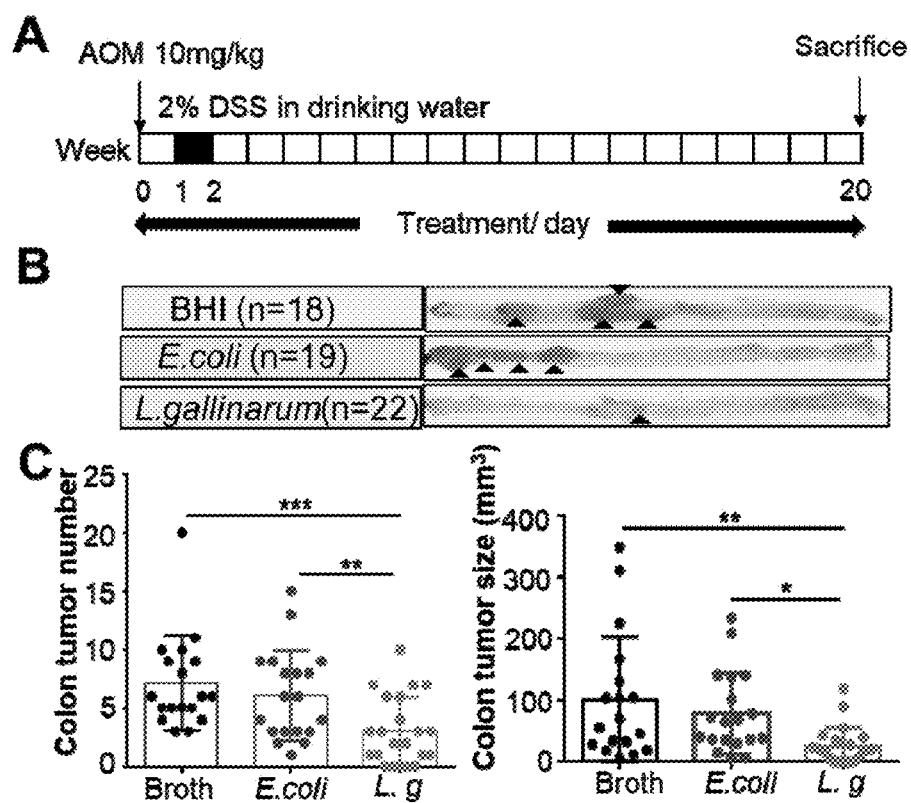
FIG. 12 shows that *L. gallinarum* protects against intestinal tumorigenesis in AOM/dextran sulfate sodium (DSS)-induced CRC mice. (A) Schematic diagram showing the experimental design, timeline of male AOM/DSS mouse model. (B) Representative images of colon tumor from male AOM/DSS mouse model. (C) Colon tumor number and tumor size in male AOM/DSS mice under different treatments. Each black triangle indicates one tumor location. P-values are calculated by one-way ANOVA. *p<0.05, p<0.01, *p<0.001. L.c, *L. casei*; L.g, *L. gallinarum*; SI, small intestine.

*L. gallinarum* Protects Against Intestinal Tumorigenesis in AOM/DSS-Induced CRC Mice To validate the tumor-suppressive effect of *L. gallinarum* on colorectal tumorigenesis, a colitis-associated CRC model was established, in which 6-week-old C57BL/6 mice were intraperitoneally injected with 10 mg/kg AOM, followed by 2% DSS administration for 1 week (FIG. 12A). *L. gallinarum* significantly reduced colorectal tumor number (*E. coli*, p<0.05; broth control, p=0.007) and tumor size (*E. coli*, p=0.019; Broth control, p=0.0013) (FIGS. 12B and 12C), indicating that *L. gallinarum* also suppresses intestinal tumorigenesis in AOM/DSS-induced CRC mice.

*L. gallinarum* Modulates the Gut Microbiota of Apc$^{Min/+}$ Mice

Figure 13A:
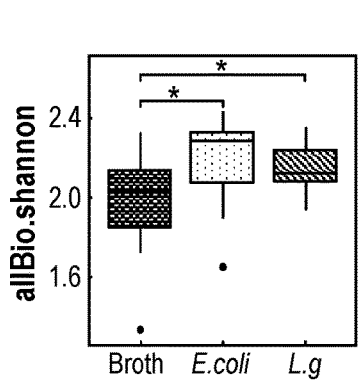
FIG. 13 shows that *L. gallinarum* modulates the gut microbiota of Apc$^{Min/+}$ mice. (A) a-diversity analysis of luminal microbiota operational taxonomic units (I) at various taxonomic ranks. (B) Principal coordinate analysis (PCoA) of β-diversity based on Bray-Curtis dissimilarity matrix IOTU-level compositional profiles. Ellipses represent 95% confidence intervals. Solid diamond-shaped points in black denote species scores, which were calculated using the vegan R-CRAN package. (C) Heatmap of differentially abundant bacterial OTUs using one-way analysis of variance, at p<0.05. L.g, *L. gallinarum*.
Figure 13B:
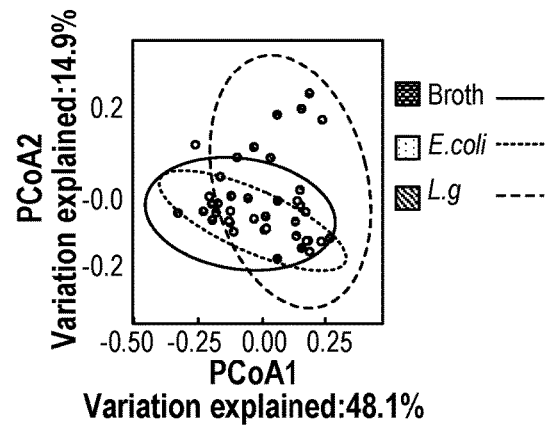
Figure 13C:
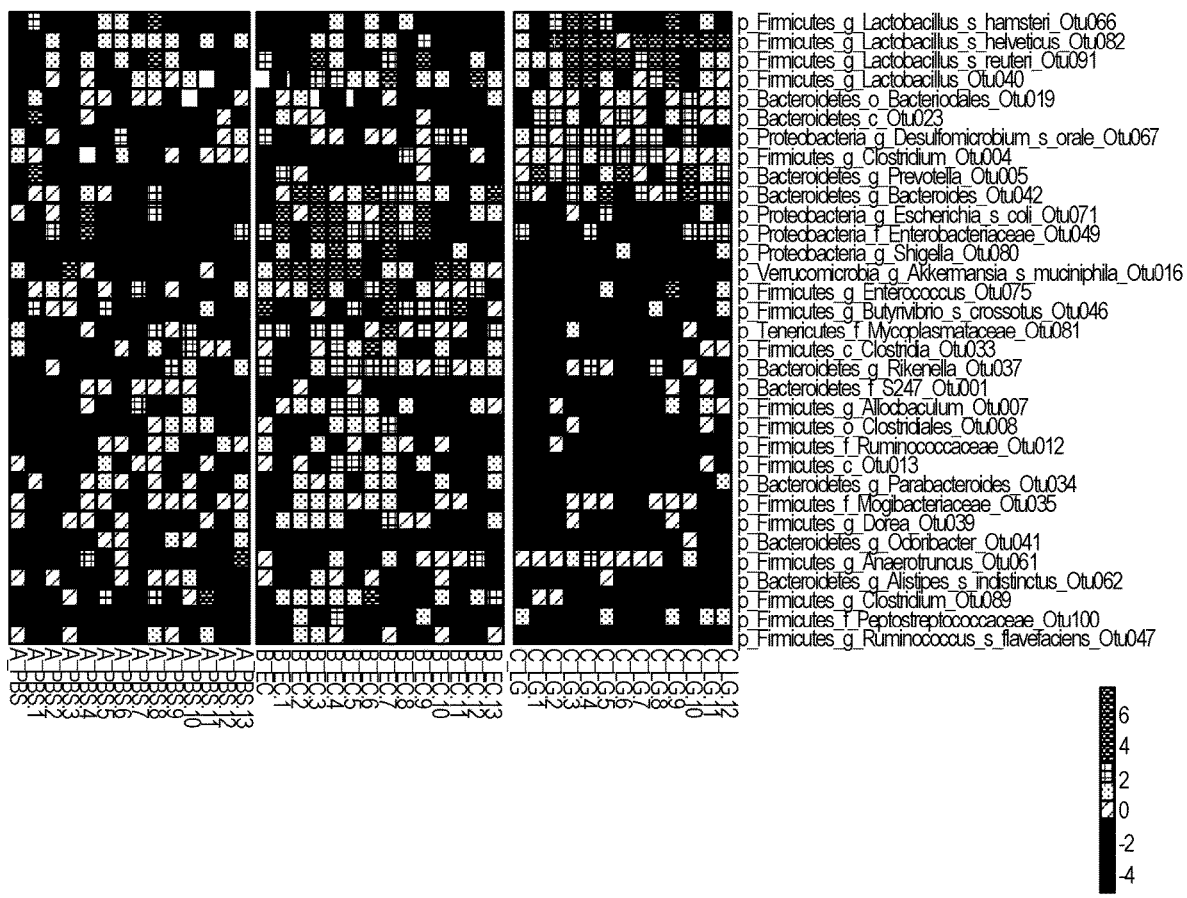

To investigate the effects of *L. gallinarum* on gut microbiota, 16S rRNA gene sequencing was performed on Apc$^{Min/+}$ mouse stool samples after gavage of *L. gallinarum* for 8 weeks. The microbial abundance in *L. gallinarum* group significantly increased compared with broth control (p<0.05), while there was no difference between *L. gallinarum* and *E. coli* groups (FIG. 13A). Similarly, although the β-diversity of stool from *L. gallinarum*-gavaged mice had a distinct trend compared with other two groups, there was no statistical significance (FIG. 13B). However, *L. gallinarum* could enhance abundances of some well-characterized commensal probiotics including *Lactobacillus helveticus, Lactobacillus reuteri* and OTUs from the Bacteroidetes phylum (FIG. 13C). Moreover, some genera, such as *Alistipes, Allobaculum, Dorea, Odoribacter, Parabacteroides* and *Ruminococcus* with species of pathogenic potentials, exhibited significantly decreased abundances in mice treated with *L. gallinarum* compared with control groups (FIG. 13C). Taken together, although *L. gallinarum* did not change the overall gut microbiota composition, it enriched the abundance of probiotics and potentially deplete gut pathogens.

L. gallinarum Supernatant Inhibits the Viability of Colon Cancer Cells

Figure 14:
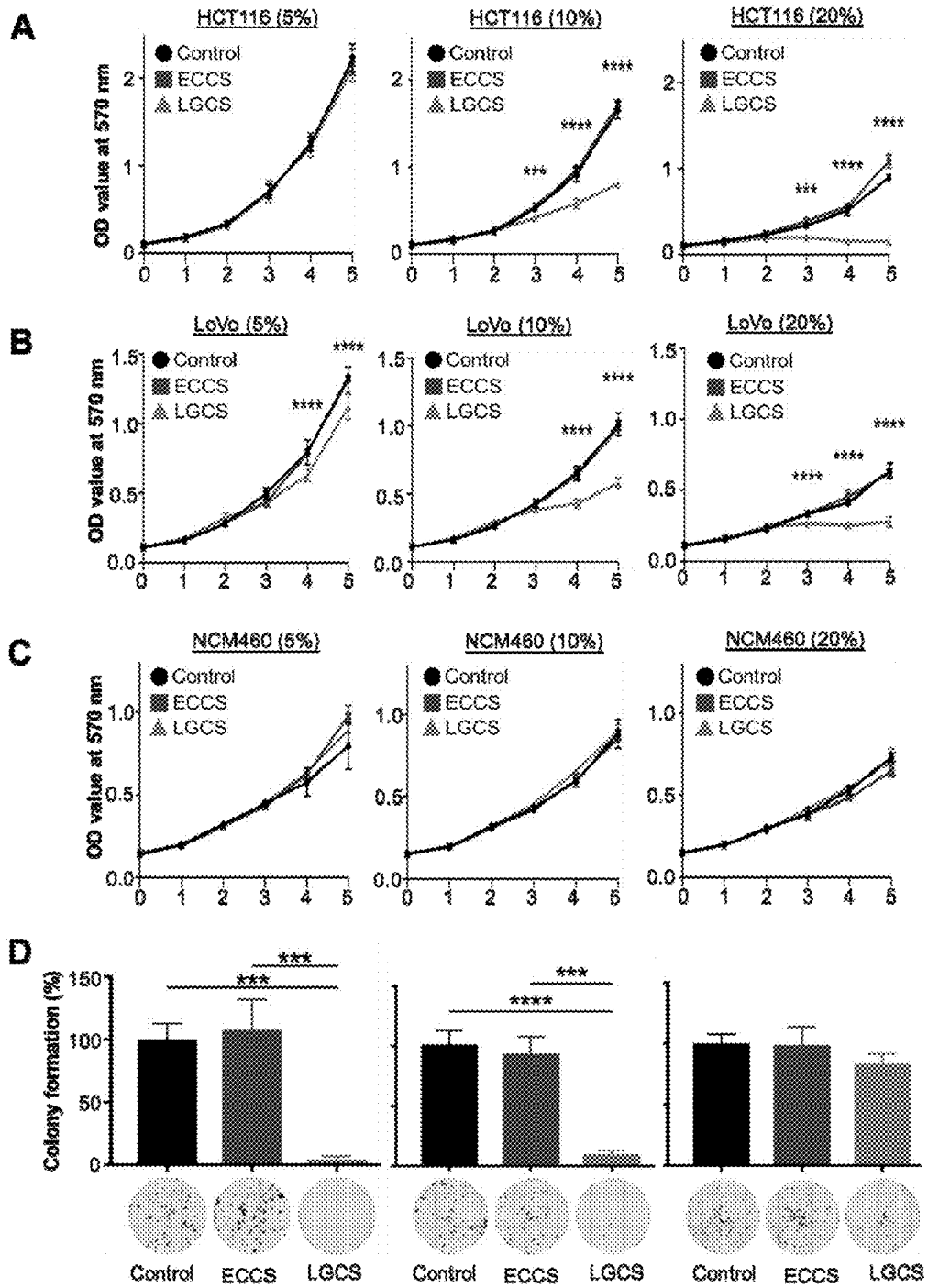
FIG. 14 shows that *L. gallinarum* supernatant inhibits the viability of colon cancer cells. The proliferation of cells was measured by MTT assay. Different concentrations of culture supernatant were used for culturing CRC cell lines, HCT116 (5%, 10%, 20%) and LoVo (5%, 10%, 20%), and normal colonic epithelial cell line, NCM460 (5%, 10%, 20%). (A) The culture supernatant of *L. gallinarum*, especially in 10% and 20%, significantly suppressed the cell growth of HCT116 from day 4 to day 5. (B) The cell growth of LoVo was also significantly suppressed by the culture supernatant of *L. gallinarum* with different concentrations; both 5% and 10% from day 4 to day 5, and 20% from day 3 to day 5. (C) No change in cell growth could be observed in the normal colonic epithelial cell line NCM460. (D) 20% LGCS suppressed colony formation of CRC cells. P-values are calculated by two-way ANOVA. *p<0.001, **p<0.0001. ECCS, *E. coli* culture supernatant; LGCS, *L. gallinarum* culture supernatant.

To validate the tumor-suppressive effect of L. gallinarum in vivo, in vitro functional analyses were performed using two CRC cell lines (HCT116 and LoVo) and a normal colonic epithelial cell line (NCM460) as control. Treatment with the culture supernatant of L. gallinarum significantly reduced the viability of CRC cell lines in a concentration-dependent manner, but not in normal colonic epithelial cell line as determined by cell viability assay (FIG. 14A-C). Similar results were observed in colony formation assay in which HCT116 (ECCS, p=0.0002; control broth, p=0.0003) and LoVo (ECCS, p=0.0001; control broth, p=7.6×10$^{-5}$) showed significant decrease in colony compared with ECCS or broth control groups (FIG. 14D). These data indicate that the secreted molecules from L. gallinarum, can suppress the viability and colony-forming ability of CRC cells.

L. gallinarum Supernatant Promotes Apoptosis in CRC Cells

Figure 15:
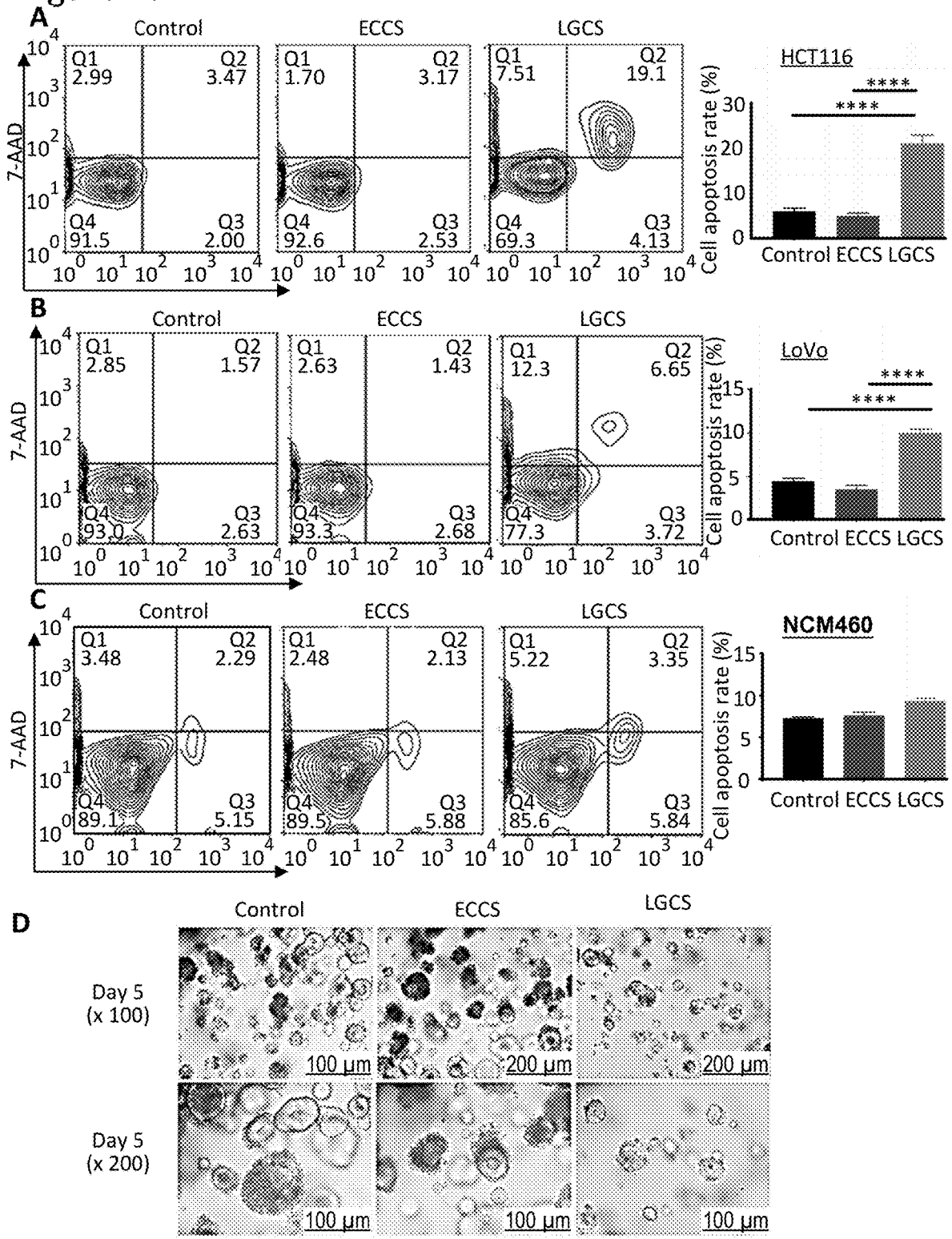
FIG. 15 shows that *L. gallinarum* supernatant promotes apoptosis instead of cell cycle arrest in CRC cells. (A) LGCS significantly promoted apoptosis including both early and late phases in two CRC cell lines HCT116, and (B) LoVo, but not (C) in the normal colonic epithelial cell line NCM460. (D) The size and number of CRC patient-derived organoids was visually reduced in medium containing 10% LGCS. (E) LGCS significantly promoted apoptosis including both early and late phases in CRC patient-derived organoids. (F) LGCS had no effect on cell cycle distribution in HCT116, (G) LoVo and (H) NCM460. P-values are calculated by one-way ANOVA. p<0.01, **p<0.0001. ECCS, *E. coli* culture supernatant; LGCS, *L. gallinarum* culture supernatant.
Figure 15:
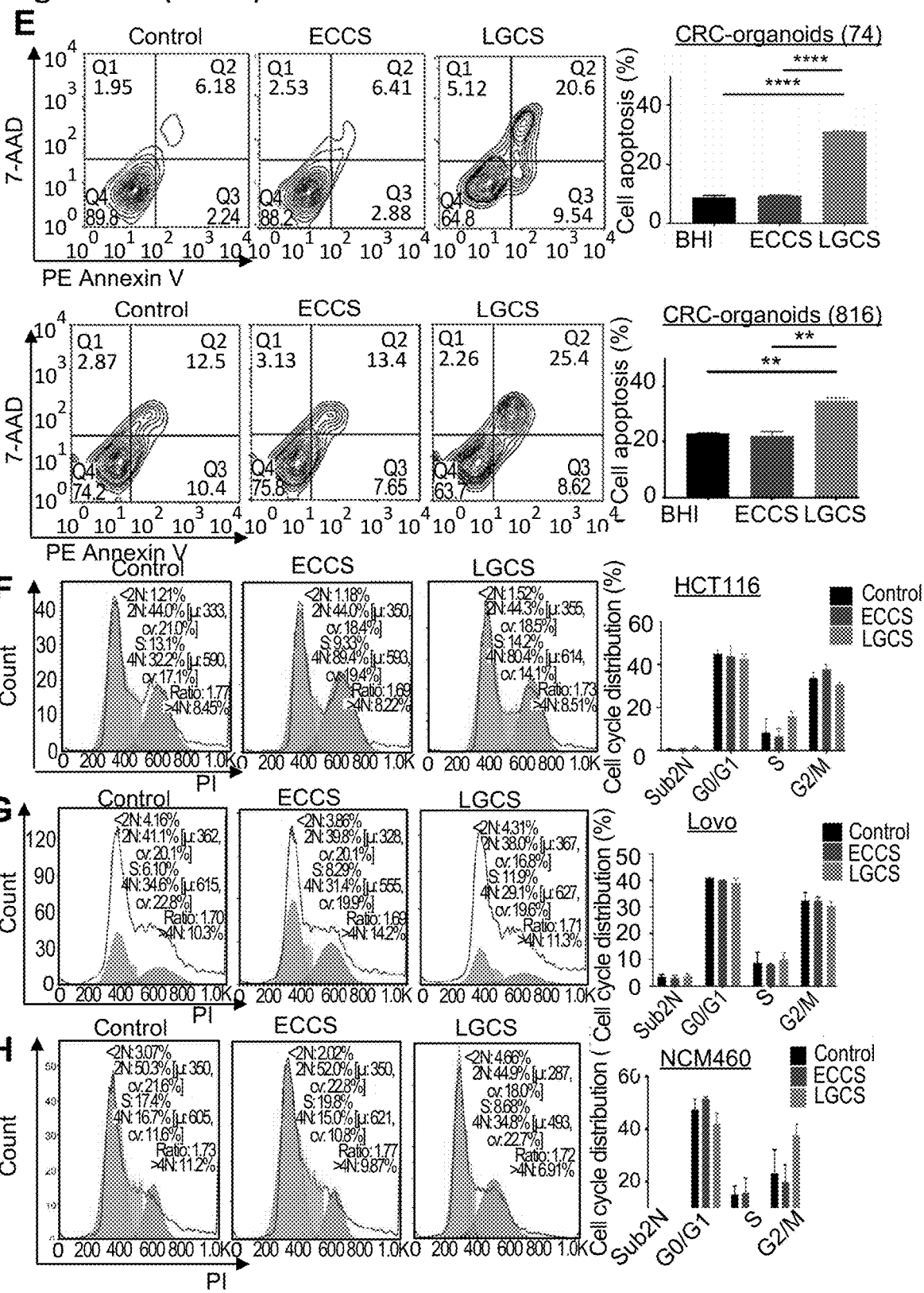

To determine the mechanism by which LGCS suppresses CRC cell viability, the effects of LGCS on apoptosis and cell cycle distribution were assessed quantitatively by flow cytometry with Annexin V-PE and 7-AAD staining. It was discovered that LGCS significantly promoted apoptosis in CRC cell lines, HCT116 (ECCS, p=3.3×10$^{-6}$; control broth, p=5.1×10$^{-6}$) (FIG. 15A) and LoVo (ECCS, p=1.4×10$^{-6}$; control broth, p=3.6×10$^{-6}$) (FIG. 15B), while it had no effect on normal epithelial colonic cells, NCM460 (FIG. 15C). Moreover, this apoptosis-inducing property of LGCS was confirmed on CRC organoids derived from 2 patients, 74 (ECCS, p=1.2×10$^{-5}$; control broth, p=0.0001) and 816 (ECCS, p=0.0013; control broth, p=0.0016) (FIGS. 15D and 15E). By contrast, LGCS had no effect on cell cycle distribution in CRC cells (FIG. 15F-H).

Figure 16:
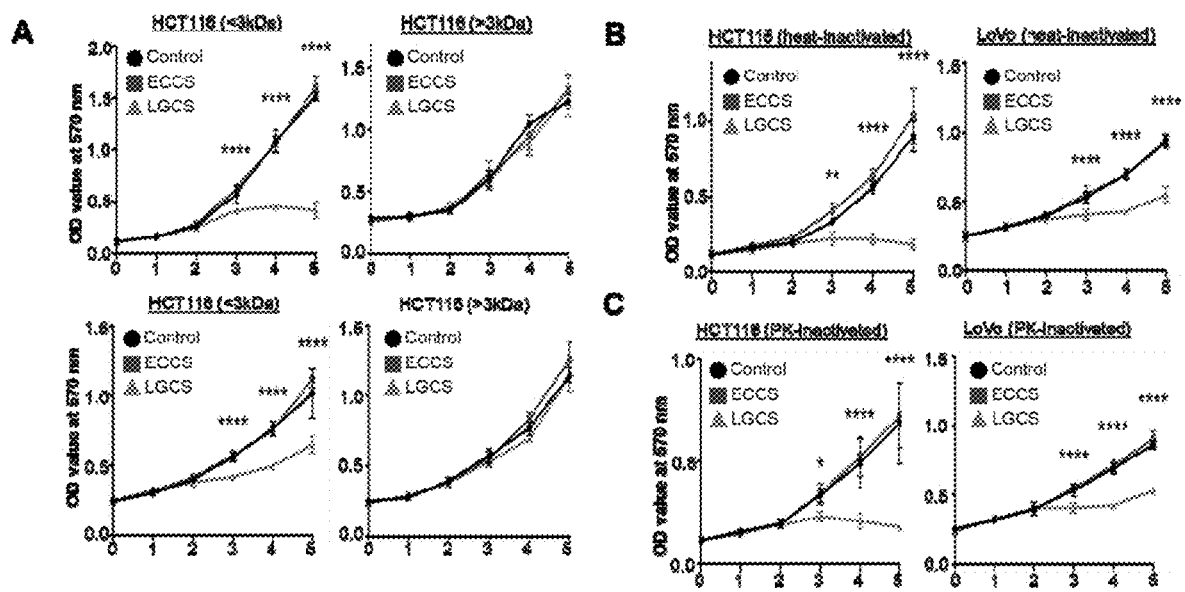
FIG. 16 shows that Anti-tumor molecules produced from *L. gallinarum* are non-protein with a molecular weight<3 kDa. (A) Low-molecular-weight (LMW)-LGCS but not HMW-LGCS significantly suppressed cell growth of HCT116 and LoVo. (B) Decrease in proliferation of CRC cells was observed in heat-inactivated-LGCS. (C) Decrease in proliferation of CRC cells was observed in proteinase k-inactivated-LGCS. P-values are calculated by two-way ANOVA. *p<0.05, p<0.01, **p<0.0001. ECCS, *E. coli* culture supernatant; LGCS, *L. gallinarum* culture supernatant; PK, proteinase K.

Anti-Tumor Molecules Produced from L. gallinarum are Non-Protein with a Molecular Weight<3 kDa To investigate the features of molecules produced from L. gallinarum responsible for anti-CRC activity, bacterial culture supernatant was separated into LMW (<3 kDa) and HMW (>3 kDa) fractions using 3-kDa filter units. Decrease in viability of CRC cells was observed only in those treated with LGCS LMW fraction, while LGCS HMW fraction had no suppressive effect on CRC cells (FIG. 16A). Meanwhile, both heat-inactivated-LGCS (FIG. 16B) and proteinase K-treated-LGCS retained the ability to reduce cell the viability of CRC cells (FIG. 16C). Collectively, these results indicated that the anti-CRC properties of L. gallinarum could be induced by non-protein molecules with a molecular weight<3 kDa.

L. gallinarum Produce and Catabolize L-Tryptophan to Release Indole-3-Lactic Acid to Protect Against CRC LC-MS/MS was next performed to identify the anti-CRC metabolite(s) in the LGCS-LMW fraction Score plots of principal component analysis (PCA) showed clear separations among the LMW fractions of LGCS, ECCS and control broth groups with LMW (FIG. 17A). Differential abundance analysis showed the critical products generated from L. gallinarum may contribute to the anti-CRC effects (FIG. 17B). To prove L. gallinarum produced LMW tumor-suppressive molecules are to some extent responsible for the anti-CRC effect of L. gallinarum in vivo, the intestine metabolomics were then examined by using the fecal samples from Apc$^{Min/+}$ mice under different treatments. Daily administration of L. gallinarum caused a significant overall compositional alteration of the gut metabolites as revealed by PCoA (FIG. 17C). Among the identified critical products, four metabolites including palmitic acid, 4-Pyridoxic acid, L-tryptophan (Try) and gamma-L-Glutamyl-L-glutamic acid were found to be overlapped in both the bacteria culture supernatant and the Apc$^{Min/+}$ mice (FIG. 17D). Notably, Try was the only one metabolite, which was enriched significantly in the LGCS-LMW fraction and the L. gallinarum-treated Apc$^{Min/+}$ mice, suggesting the possibility that Try can be secreted from L. gallinarum directly. Try is an essential amino acid for host, intake of Try from dietary may reach the colon, where the bacteria will degrade them into its catabolites[50]. Concordantly, L. gallinarum administration was found to cause enrichment of Try catabolites, especially the indole derivatives in Apc$^{Min/+}$ mice (FIG. 17E). It was hypothesized that L. gallinarum is the Try and/or Try catabolites producer.

Figure 18:
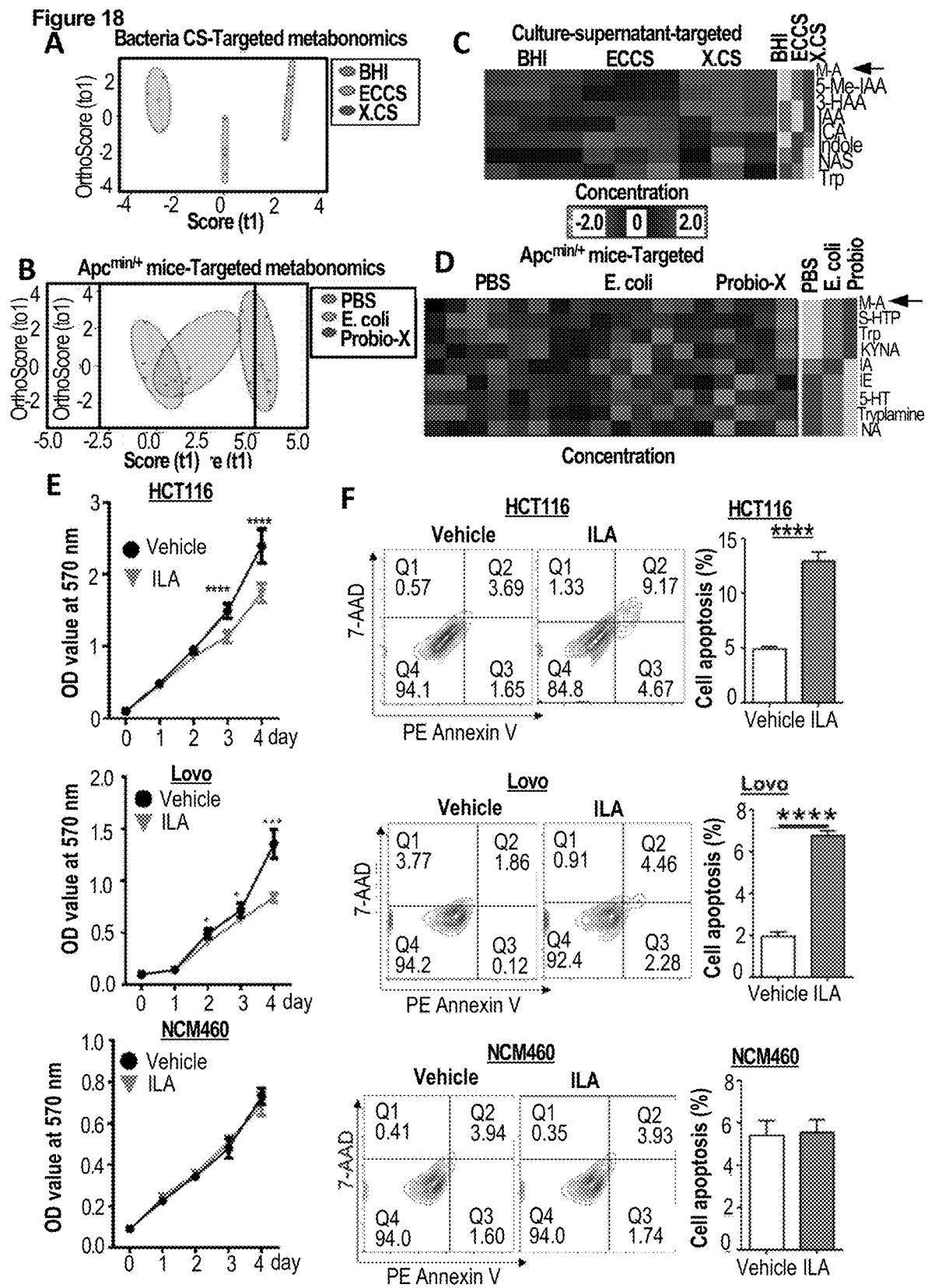
FIG. 18 shows that Probio-X catabolizes Try to produce M-X to protect against CRC. Targeted metabonomics on L-tryphtophan were performed on different culture supernatants and fecal samples from Apc$^{Min/+}$ mice under different treatments. (A) Score plots of PCA revealed clear separations among culture supernatant of Probio-X, *E. coli* MG1655 and control broth groups. (B) Score plots of PCA revealed clear separations among fecal samples from Probio-X-treated, *E. coli* MG1655-treated and control Apc$^{Min/+}$ mice. (C) Heatmap analysis revealed the abundance of different metabolites in X.CS, ECCS and control broth groups. (D) Heatmap analysis revealed the abundance of different metabolites in the gut of Apc$^{Min/+}$ mice under different treatments. (E) The cell growth of CRC cells was significantly suppressed by M-X. (F) The cell apoptosis of CRC cells was significantly increased by M-A. (G) Schematic diagram showing the experimental design, timeline and representative macroscopic images of colons from of M-A-treated Apc$^{Min/+}$ mouse model. (H) Colon, small intestinal and total tumor number (colon+small intestinal) in Apc$^{Min/+}$ mice with or without M-A treatment. (I) Colon, small intestinal with or without M-A treatment. (J) TUNEL positive staining cells in colon tissues of Apc$^{Min/+}$ mice with or without M-A treatment. Each black triangle indicates one tumor location. (K) The transcription of AhR was significantly suppressed by CH-223191 (100 nM). (L) Pre-treat CRC cells with CH-223191 (100 nM) for 12 hours abolished the anti-proliferation effect of X.CS. (M) Schematic diagram showing the experimental design, timeline and representative macroscopic images of colons from female Apc$^{Min/+}$ mouse model. (N) Colon, small intestinal and total tumor number (colon+small intestinal) in female Apc$^{Min/+}$ mice under different treatments. (O) Colon, small intestinal and total tumor size (colon+small intestinal) in female Apc$^{Min/+}$ mice under different treatments. (P) Schematic diagram showing the experimental design, timeline and representative macroscopic images of colons from male Apc$^{Min/+}$ mouse model. (Q) Colon, small intestinal and total tumor number (colon+small intestinal) in male Apc$^{Min/+}$ mice under different treatments. (R) Colon, small intestinal and total tumor size (colon+small intestinal) in male Apc$^{Min/+}$ mice under different treatments. Each black triangle indicates one tumor location. P-values are calculated by two-way ANOVA or Student's t-test as appropriate. *p<0.05, p<0.01, **p<0.0001. ECCS, E. coli culture supernatant; X.CS, Probio-X culture supernatant; M-X, Metabolite-X.
Figure 18:
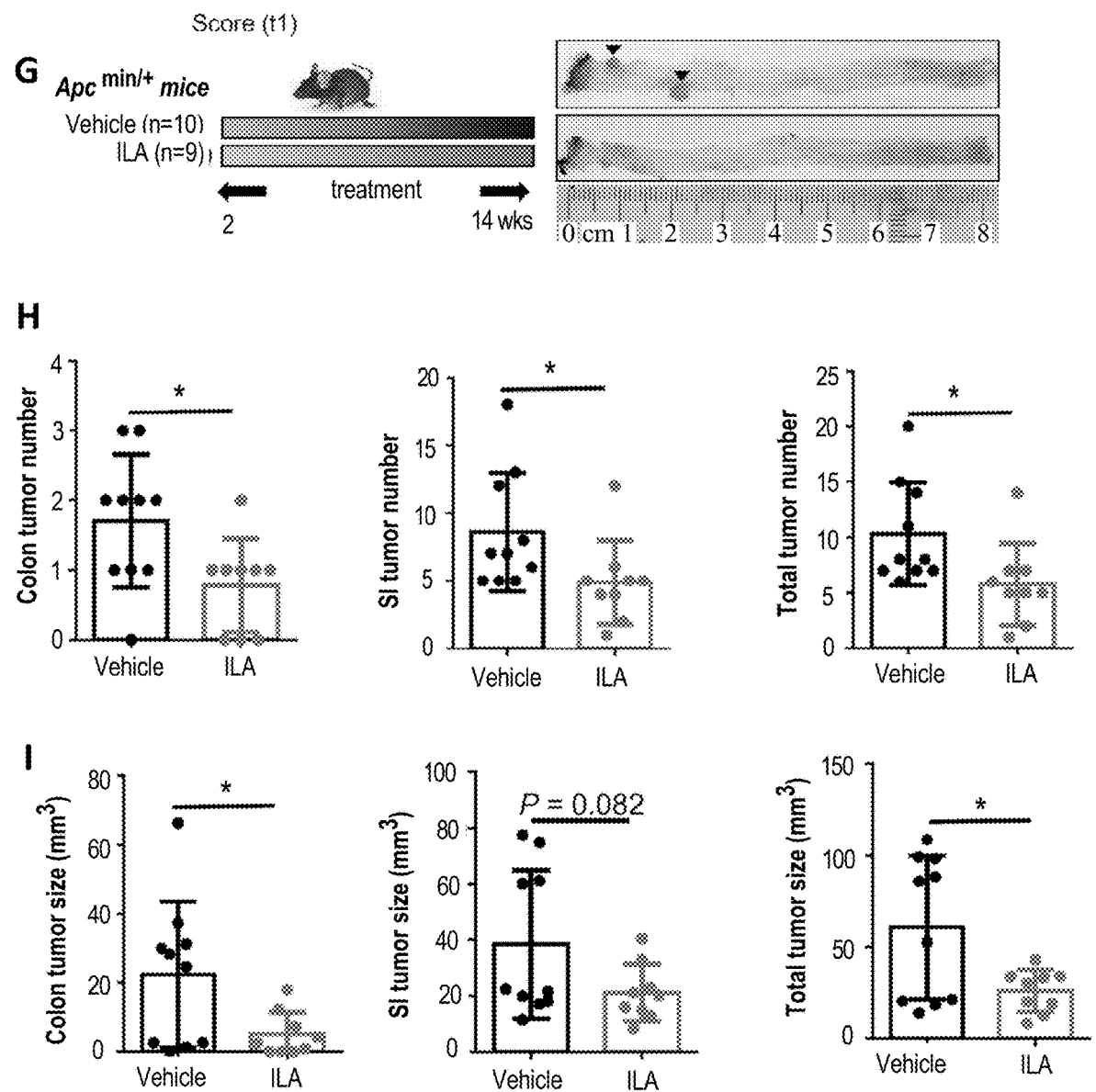
Figure 18:
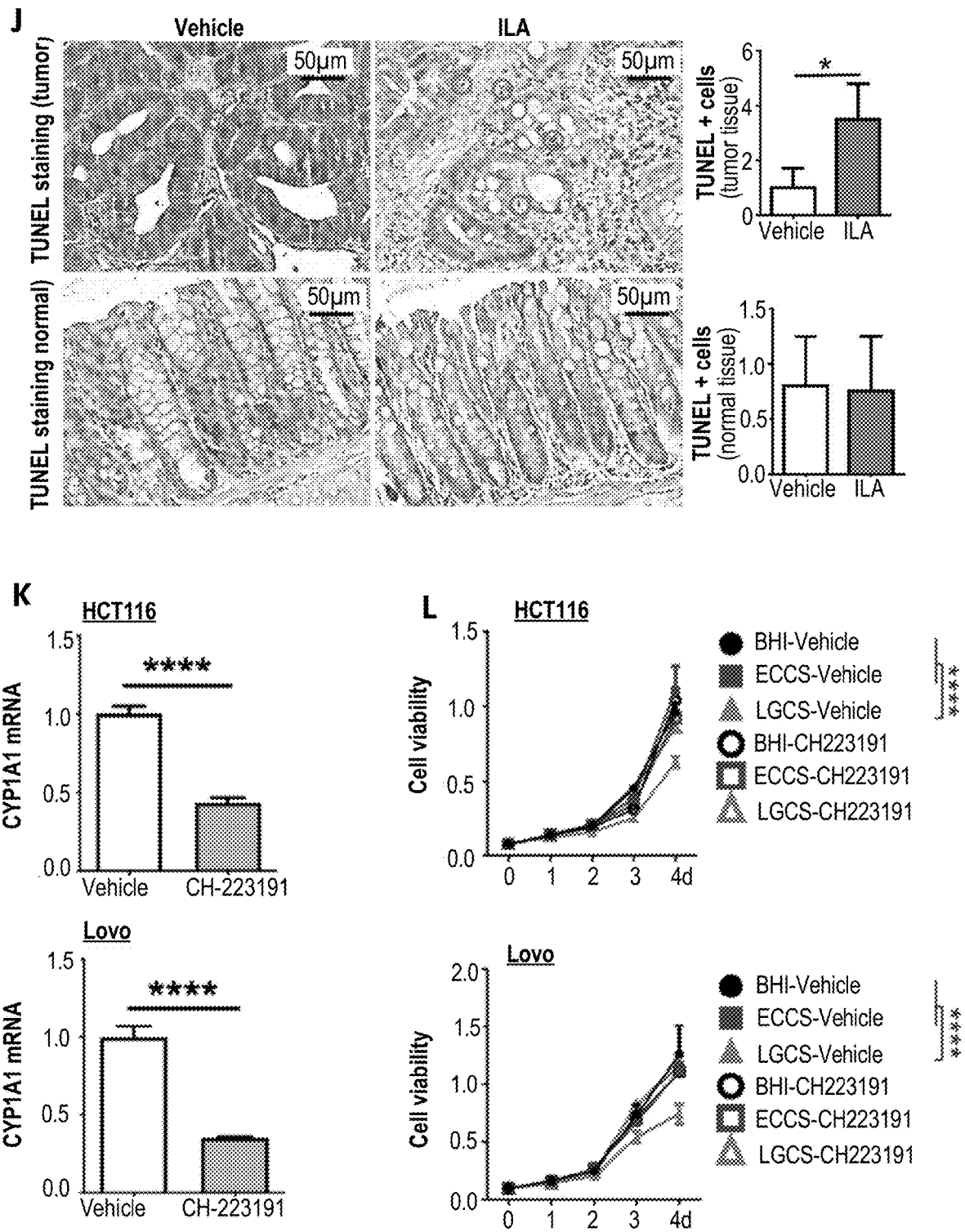

Next, further confirmation was sought for the catabolizing and/or production of Try form L. gallinarum through high throughput targeted Try metabolic profiling. The PCA regarding Try and its downstream metabolites showed obvious separations among control, ECCS and LGCS groups (FIG. 18A). Differential abundance analysis showed that Try level was decreased in LGCS-LMW (FIG. 18C), suggesting the Try catabolizing capacity of L. gallinarum. The catabolizes of Try were then examined, and it was found that indole-3 lactic acid (ILA), which was one of the downstream catabolites from Try, enriched in both the LGCS-LMW and the stool samples from L. gallinarum-treated Apc$^{Min/+}$ mice (FIG. 18B-18D). The cell viability of CRC cells decreased substantially when exposed to the same amount of ILA as produced form L. gallinarum (FIG. 18E), indicating that L. gallinarum can produce Try, and at the same time can use Try to produce Try catabolites.

Functional investigation of ILA in CRC tumorigenesis was then performed in vivo. As shown in FIG. 18G, gavage of ILA (20 mg/kg) into Apc$^{Min/+}$ mice significantly reduced tumor number (FIG. 18H) and tumor size (FIG. 18I). The amount of cells with positive TUNEL staining was also increased in ILA-treated tumor tissues, but not in adjacent normal tissues (FIG. 18J). Moreover, additional experiments were performed to investigate if antagonizing ILA could abrogate L. gallinarum medicated anti-cancer effect. As shown in S FIG. 18K, blocking ILA receptor, aryl hydrocarbon receptor (AhR), using AhR antagonist (CH-223191)[22,23] abolished the effect of L. gallinarum in suppressing CRC in vitro (FIG. 18L) and in Apc$^{Min/+}$ mice (FIG. 18M-18R). Collectively, these data indicate that L. gallinarum can produce L-tryptophan, and at the same time, convert it to its downstream ILA and other metabolites. Thus, ILA can contribute, at least in part, to the tumor-suppressive effect of L. gallinarum.

Discussion

This study has demonstrated for the first time that oral administration of L. gallinarum reduced intestinal tumor number and size in Apc$^{Min/+}$ mice and confirmed in DSS/AOM induced CRC mouse model, indicating that L. gallinarum suppresses CRC tumorigenesis. From in vitro experiments, small non-protein metabolites produced by L. gallinarum were observed to suppress the growth of CRC cells and CRC patient-derived organoids by promoting apoptosis.

Certain probiotics can suppress the progression of CRC in preclinical experiments[51-56]. For example, both living and heat-killed Lactobacillus rhamnosus GG (LGG) have anti-CRC effect by promoting apoptosis in human CRC cells[57]. In animal model, LGG could suppress CRC development by increasing the expression of pro-apoptotic proteins such as Bax, casp3 and p53[58]. Several studies have suggested that regular consumption of probiotics may improve the imbalanced intestinal microbiota, thus reducing the chance of chronic inflammation and production of carcinogenic compounds during intestinal dysbiosis[59-61].

In the present study, it was discovered that *L. gallinarum* significantly enriched the abundance of well-characterized commensal probiotics such as *L. helveticus* and *L. reuteri*, while some pathogenic potential species such as *Alistipes, Allobaculum, Dorea, Odoribacter, Parabacteroides* and *Ruminococcus*[62-64] were significantly depleted in mice treated with *L. gallinarum*. *L. reuteri* is known to suppress inflammation-associated colon carcinogenesis by producing histamine[65]. Thus, *L. gallinarum* suppresses CRC at least in part through enriching the abundance of probiotics and depleting potential CRC pathogens. Gut microbiota plays a critical role in CRC tumorigenesis. One previous study showed that transplantation of feces from patients with CRC can promote tumorigenesis in germ-free mice and mice receiving carcinogen AOM[66]. Another study demonstrated that transplantation of fecal samples from AOM/DSS mice to germ-free mice led to increased tumor development compared with those harboring fecal samples from naive healthy mice[67]. These studies suggest that gut dysbiosis contribute to tumor susceptibility and alteration of the intestinal microbiota is an important determinant of colon tumorigenesis. Meanwhile, some studies found that probiotics can alter the composition of microbiota to alleviate cancer progression. For example, *Lactobacillus salivarius* Ren could suppress CRC tumorigenesis via modulating intestinal microbiota[68,69]. These findings collectively inferred that probiotics like *L. gallinarum* suppress CRC development through modulating gut microbial composition.

This study also demonstrated that the metabolites produced by *L. gallinarum* suppressed CRC cell growth through inducing apoptosis. Using metabolomic analysis, it was revealed that *L. gallinarum* can not only produce Try, but also catabolize Try to produce Try catabolites. Recent data suggest that Try catabolites generated by the gut microbiota are important contributors in maintaining intestinal homeostasis[50]. It is further identified that ILA, one of the Try catabolites, significantly increased in the LGCS and *L. gallinarum*-treated Apc$^{Min/+}$ mice. ILA was identified to be a metabolite of breastmilk tryptophan, secreted by probiotic *Bifidobacterium longum* to prevent intestine inflammation[70]. In addition, production of ILA through gut microbial was reported to alleviate colitis in mice through inhibiting epithelial autophagy. CRC is influenced by the balance between microbial production of health-promoting metabolites (e.g., short-chain fatty acids) and potentially carcinogenic metabolites (e.g., secondary bile acids[71]. Previous studies have demonstrated the anti-carcinogenic attributes of probiotic metabolites, especially for those produced by LAB[72,73]. For example, metabolites produced by *Lactobacillus plantarum* exhibited selective cytotoxicity via provoking antiproliferative activity and inducing apoptosis against malignant cancer cells[74]. Ferrichrome derived from *L. casei* has a strong tumor-suppressive effect on CRC cells by inhibiting the JNK signaling pathway[75]. Thus, the anti-CRC feature of *L. gallinarum* could be also at least in part contribute to its released protective metabolites. However, whether ILA secreted from *L. gallinarum* is the main metabolite for CRC suppression requires further investigation.

In conclusion, this study is the first to demonstrate the anti-CRC effect of *L. gallinarum*. *L. gallinarum* protects against intestinal tumorigenesis. Such action is associated with the modulation of the gut microbial composition and the secretion of protective metabolites including ILA to promote apoptosis in cancer cells. These findings may facilitate the development of therapeutic strategy using probiotics for chemoprevention of CRC.

Example III: Synergistic Effect of *Lactobacillus gallinarum* and *Carnobacterium maltaromaticum* in Protecting Against Colorectal Tumorigenesis Background of the Invention A single CRC-depleted probiotic has been proved to act as a novel prophylactic for CRC prevention in mice with minimal side effects. The underlying mechanism between different probiotic species are quite different. In light of the complexity and heterogeneity of tumors, combining different probiotics to explore its synergistic effect will probably be a powerful weapon in the battle against CRC.

Materials and Methods

Animal Experiments

Male C57BL/6 mice at 6 weeks old were intraperitoneally injected with a single dose of 10 mg/kg AOM (Merck, Darmstadt, Germany), followed by 2% DSS (MP Biomedicals, Solon, OH) administration for 1 week. After DSS treatment, all the mice were randomly assigned into 5 groups: (1) BHI; (2) *E. coli* MG1655 (1.0×10$^8$ colony-forming units (CFUs)); (3) *L. gallinarum* (1.0×10$^8$ CFUs); (4) *C. maltaromaticum* (1.0×10$^8$ CFUs); and (5) *L. gallinarum* (0.5×10$^8$ CFUs)+*C. maltaromaticum* (0.5×10$^8$ CFUs). Mice were gavaged once daily for 20 weeks. Mouse colonoscopy (Karl Storz Endoskope, Tuttlingen, Germany) was performed prior to sacrifice. After sacrifice, the colons of mice were longitudinally opened and rinsed with PBS. Total number of tumors in colon were recorded. All the procedures were performed in accordance with guidelines approved by the Animal Experimentation Ethics Committee of The Chinese University of Hong Kong.

Bacterial Strains and Culture Conditions

All the bacteria stain and culture condition were the same as used in Examples I and II.

Multicolour Flow Cytometry Analysis

Multicolour flow cytometry was performed as we described previously[8]. In brief, colon tissues were dissected into small pieces and digested with Hank's balanced salt solution with 0.1 mg/ml collagenase D and 50 U/ml DNase I for 30 min at 37° C. on a shaking platform. The cell suspension was filtered through a 70-μm cell strainer and centrifuged at 500 g for 20 min. The cell pallet was resuspended in Hank's media plus 1% fetal calf serum (FCS) for cell surface marker analysis.

Statistical Analysis

Results are expressed as mean±standard deviation (SD). ANOVA was used to compare differences among multiple groups, and post-hoc analysis was performed by Tukey's multiple comparisons test. P-values<0.05 indicate statistical significances.

Figure 19:
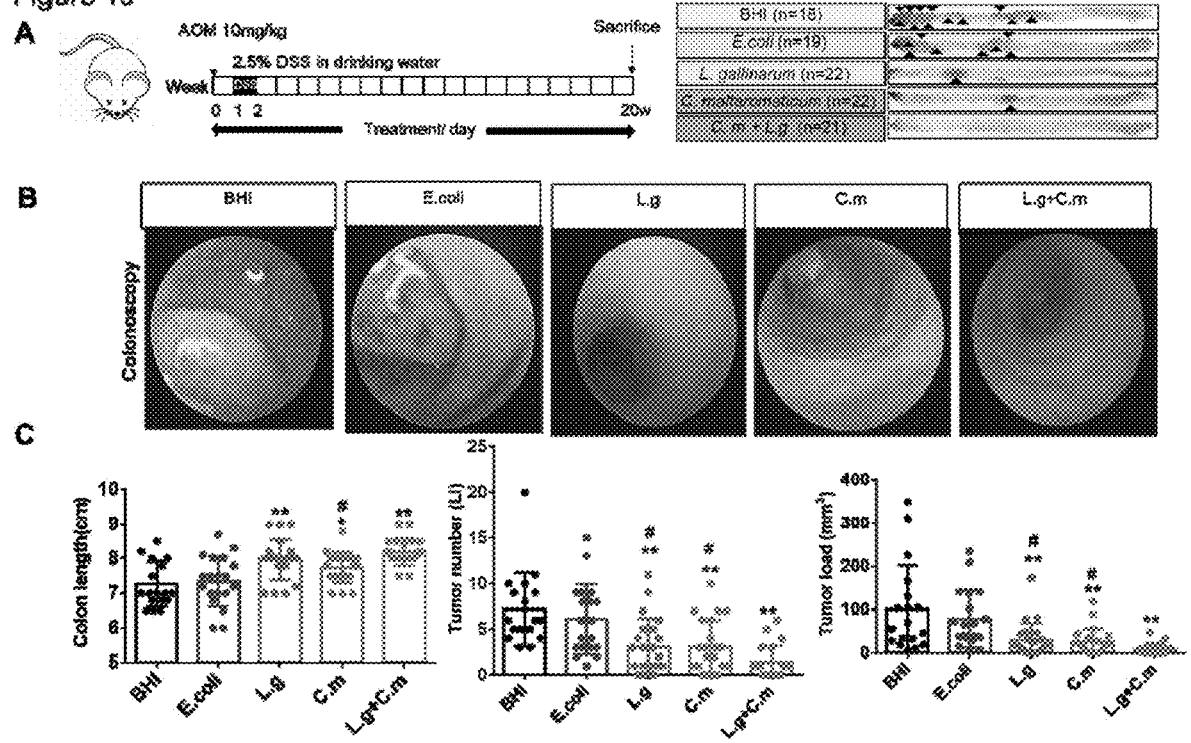
FIG. 19 shows that Combined L. gallinarum and C. maltaromaticum synergistically protects against intestinal tumorigenesis in AOM/DSS-induced CRC mice. (A) Schematic diagram showing the experimental design, timeline of AOM/DSS mouse model. (B) Representative images of colon tumor from AOM/DSS mouse model. (C) Colon tumor number and tumor size in male AOM/DSS mice under different treatments. Each black triangle indicates one tumor location. P-values are calculated by one-way ANOVA. *p<0.05, p<0.01, *p<0.001. C.m, C. maltaromaticum; L.g, L. gallinarum.

Combined *L. gallinarum* and *C. maltaromaticum* Synergistically Protects Against Intestinal Tumorigenesis in AOM/DSS-Induced CRC Mice To investigate the synergistic effect of *L. gallinarum* and *C. maltaromaticum* on colorectal tumorigenesis, DSS-promoted, AOM-induced CRC mice were randomized treated with *L. gallinarum*, *C. maltaromaticum* alone, and combination of *L. gallinarum*+*C. maltaromaticum*. BHI and a non-tumorigenic *E. coli* strain MG1655 were used as plain culture broth and bacteria control, respectively (FIG. 19A). After 20-week gavage, colonoscopy identified that colon tumor sizes in probiotics treated group were visually smaller than the *E. coli* MG1655 or broth control groups (FIG. 19B). In accordance with this observation, the alleviation of colonic inflammation was observed in the probiotic treated group as reflected by increased colon length. Administration of the probiotics significantly reduced the tumor number and tumor size in the colon AOM/DSS-induced CRC mice (FIG. 19C). Most strikingly, combined *L. gallinarum/C. maltaromaticum* led to an obvious reduction of colon tumor number and tumor size as compared with *L. gallinarum* or *C. maltaromaticum* alone treatment, indicating combined *L. gallinarum/C. maltaromaticum* synergistically abrogates intestinal tumorigenesis in AOM/DSS-induced CRC mice.

Figure 20:
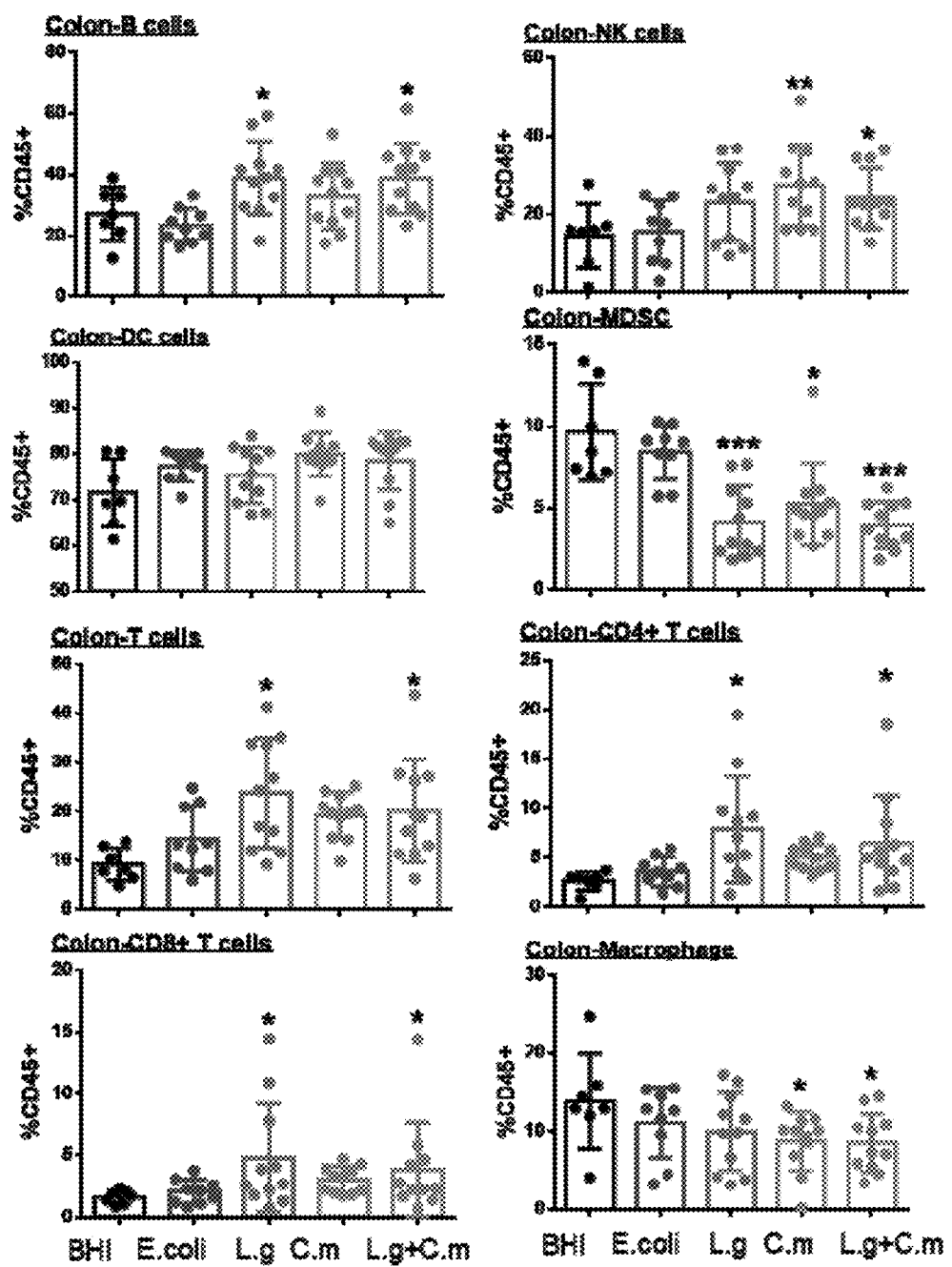
FIG. 20 shows that Combined L. gallinarum and C. maltaromaticum synergistically modified the tumor immune microenvironment in AOM/DSS-induced CRC mice.

Combined *L. gallinarum* and *C. maltaromaticum* Synergistically Modified the Tumor Immune Microenvironment in AOM/DSS-Induced CRC Mice To directly address the effect of probiotics on the tumor immune microenvironment in CRC, the composition of tumor-infiltrating immune cells isolated from the colon of AOM/DSS-induced CRC mice was investigated under different treatments. Enrichment of B cells, tumor-infiltrating $CD8^+$ cytotoxic T cells and depletion of myeloid-derived suppressor cells (MDSCs) was observed after *L. gallinarum* alone treatment as compared with BHI- or *E. coli*-treated mice. Whereby, the nature killer (NK) cells, which could act as a "tumor-killer", accumulated in *C. maltaromaticum*-treated mice, did not infiltrate the *L. gallinarum*-treated mice. In addition, *C. maltaromaticum* alone treatment decreased the MDSCs. Of note, combined *L. gallinarum/C. maltaromaticum* led to a generalized anti-cancer immune modulatory effect as revealed by upregulation of B cells, NK cells, $CD8^+$ cytotoxic T cells and downregulation of MDSCs (FIG. 20). Collectively, the results indicate that combined *L. gallinarum/C. maltaromaticum* affects numerous types of immune cells, which will mediate, at least in part of its synergistic tumor-suppressive effect.

Discussion

In this study, it was demonstrated for the first time that oral administration of a combined *L. gallinarum/C. maltaromaticum* probiotics cocktail suppresses tumor formation in the AOM/DSS mouse model in a synergistic manner. a significant reduction of tumor number and tumor size was observed in the cocktail group as compared with the probiotic alone treatment group. Furthermore, numerous immune cells, including B cells, cytotoxic T cells, NK cells and MDSCs, were identified as being involved in the cocktail-treated mice, which will partially mediate the tumor-suppressive effect of the probiotic cocktail. These results strongly recommend combined *L. gallinarum/C. maltaromaticum* probiotics cocktail as a therapeutic strategy for the prevention and treatment of CRC.

Example IV: *Lactococcus lactis* Inhibits Colorectal Tumorigenesis Through Secreting Aminopeptidase Background of the Invention Colorectal cancer (CRC) is the third most common cancer and constitutes a major health burden worldwide. Developing new prevention strategies with minimal toxicity are highly warranted. The probiotics, which interacting directly with the colon epithelial cells, supported the pivotal role for preventing CRC development by using CRC-depleted probiotics. Using shotgun metagenomic sequencing, *Lactococcus lactis* (*L. lactis*) was identified to be depleted in the stool of CRC patients as compared with healthy subjects, suggesting that the potential protective role in CRC.

In this study, *L. lactis* was shown to inhibit colorectal tumorigenesis in Apc$^{min/+}$ mouse model, human CRC-derived organoids, and CRC cell lines. The tumor-suppressive effect is attributed to the secretion of aminopeptidase by *L. lactis*.

Materials and Methods

Animal Experiments 5-week-old male C57BL/6J-Apc$^{min}$/J mice were purchased from the Jackson Laboratory (Bar Harbor, ME, USA) and maintained in the animal facility at the Chinese University of Hong Kong. 28 mice were divided into 3 groups randomly. $1.0 \times 10^8$ colony-forming units (CFUs) *L. lactis*, *E. coli* MG1655 or the same volume of BHI was administrated to them daily for 12 weeks. Mouse colonoscopy (Karl Storz Endoskope, Tuttlingen, Germany) was performed prior to sacrifice. Total number of tumors in small intestine and colon were recorded after sacrifice. All animal studies were performed in accordance with guidelines approved by the Animal Experimentation Ethics Committee of The Chinese University of Hong Kong.

Bacterial Strains Isolation and Culture Conditions

Healthy human fecal samples were collected and suspended in the PBS within 30 minutes. The obtained suspension was homogenized in beater and filtered through a 100 μm strainer to remove larger particles. The fecal suspension was then plated on the M17 agar plate and incubated in aerobic incubator at 37° C. for 24 hours. All colonies were purified by streak plate method and individually cultured for 24 hours in M17 broth (Thermo Fisher Scientific, West Palm Beach, FL) at 37° C. in aerobic incubator and the 16S rDNA for each isolate was amplified by PCR with the university primers 341F (SEQ ID NO:1:5'-CCTAYGGGRBGCAS-CAG-3') and 806R (SEQ ID NO:2: 5'-GGAC-TACNNGGGTATCTAAT-3'). The PCR product was sent for DNA sequence. *L. lactis* was identified through blasting the 16S rDNA in the GenBank.

*L. lactis* and *E. coli* MG1655 were cultured in BHI broth (Thermo Fisher Scientific, West Palm Beach, FL) at 37° C. under aerobic condition. The bacteria were centrifuged at 5,000 rpm for 10 minutes to obtain the bacteria pallet and resuspended in BHI before gavaging to mice.

Culture Supernatant of *L. lactis*

The density of *L. lactis* or *E. coli* MG1655 was measured using NanoDrop spectrophotometer (NanoDrop Technologies, Wilmington, DE). When the optical density (OD)$_{600}$ reached 0.5, the bacteria culture supernatants were centrifuged (5,000 rpm, 10 minutes) and filtered with a 0.22-μm membrane filter. Filtrates were collected and termed as *L. lactis* conditioned-medium (LL.CM) or *E. coli* MG1655 conditioned-medium (ECCM). The bacterial conditioned-medium were heated at 100° C. for 30 minutes or treated with proteinase k (PK, 50 ug/ml; QIAGEN GmbH, Hilden, Germany) to evaluate the characteristics of the tumor-suppressive molecule(s) secreted from *L. lactis*.

Cell Culture

Colon cancer cell lines, HCT116 and HT29, were purchased from ATCC. A normal colonic epithelial cell line, NCM460, was obtained from INCELL Corporation (San Antonio, TX) as control. All cells were grown in high-glucose Dulbecco's Modified Eagle's Medium (DMEM) (Thermo Fisher Scientific) supplemented with 10% fetal bovine serum (FBS) (Thermo Fisher Scientific), 2 mM L-glutamine, 50 U/ml penicillin and 50 μg/ml streptomycin in a humidified atmosphere containing 5% $CO_2$.

CRC Patient-Derived Organoid Culture

CRC organoids derived from 2 patients (74 and 828) were obtained from Princess Margaret Living Biobank (Toronto, Ontario, Canada), and embedded in Matrigel (Corning Inc, Corning, NY). 5% of the bacteria conditioned medium was used to treat the organoids. Culture medium was changed every 2 days. Organoids' sizes were calculated by using Image J.

Cell Viability Assay

Cell viability was measured by 3-(4,5-dimethylthiazoly-2-yl)-2,5-diphenylte-trazolium bromide (MTT, Sigma-Aldrich) assay. 1,000 cells were seeded on 96-well plates and treated with bacteria conditioned-medium (5%). The amount of MTT formazan product was determined by measuring absorbance at a wavelength of 570 nm (OD570) with a microplate reader (Multiskan GO Microplate Spectrophotometer, Thermo Scientific, Vantaa, Finland).

Colony Formation Assay 500 cells were seeded overnight on 12-well microplates and treated with bacteria conditioned-medium (5%) for 2 weeks. Cells were washed with phosphate-buffered saline (PBS) and fixed in methanol, prior to staining with 0.5% crystal violet. Colonies were counted manually.

Silver Staining and Protein Identification

The anti-tumor molecule(s) were resolved by sodium dodecyl sulfate-polyacrylamide gel electrophoresis (5%) (SDS-PAGE). Silver staining was performed following the instructions provided by the manufacturer (Thermo Scientific, Rockford, USA). After staining, specific bands from the >100-kDa fraction were excised by pipette tips into 1.5 ml plastic tubes for in-gel digestion following the manufacturer's instructions (Thermo Scientific, Rockford, USA). The obtained peptide mixtures were subject to mass spectrometry (MS) analysis. MS spectral data were processed using the Bruker Compass Data Analysis software, and the generated peak lists were converted into the Mascot search engine against the Swiss-Prot 51.6 database. Aminopeptidase was identified as the potential functional protein.

Statistical Analysis

Results are expressed as mean±standard deviation (SD). ANOVA was used to compare differences among multiple groups, and post-hoc analysis was performed by Tukey's multiple comparisons test. P-values<0.05 indicate statistical significances.

L. lactis Protects Against Intestinal Tumorigenesis in $Apc^{Min/+}$ Mice

Figure 21:
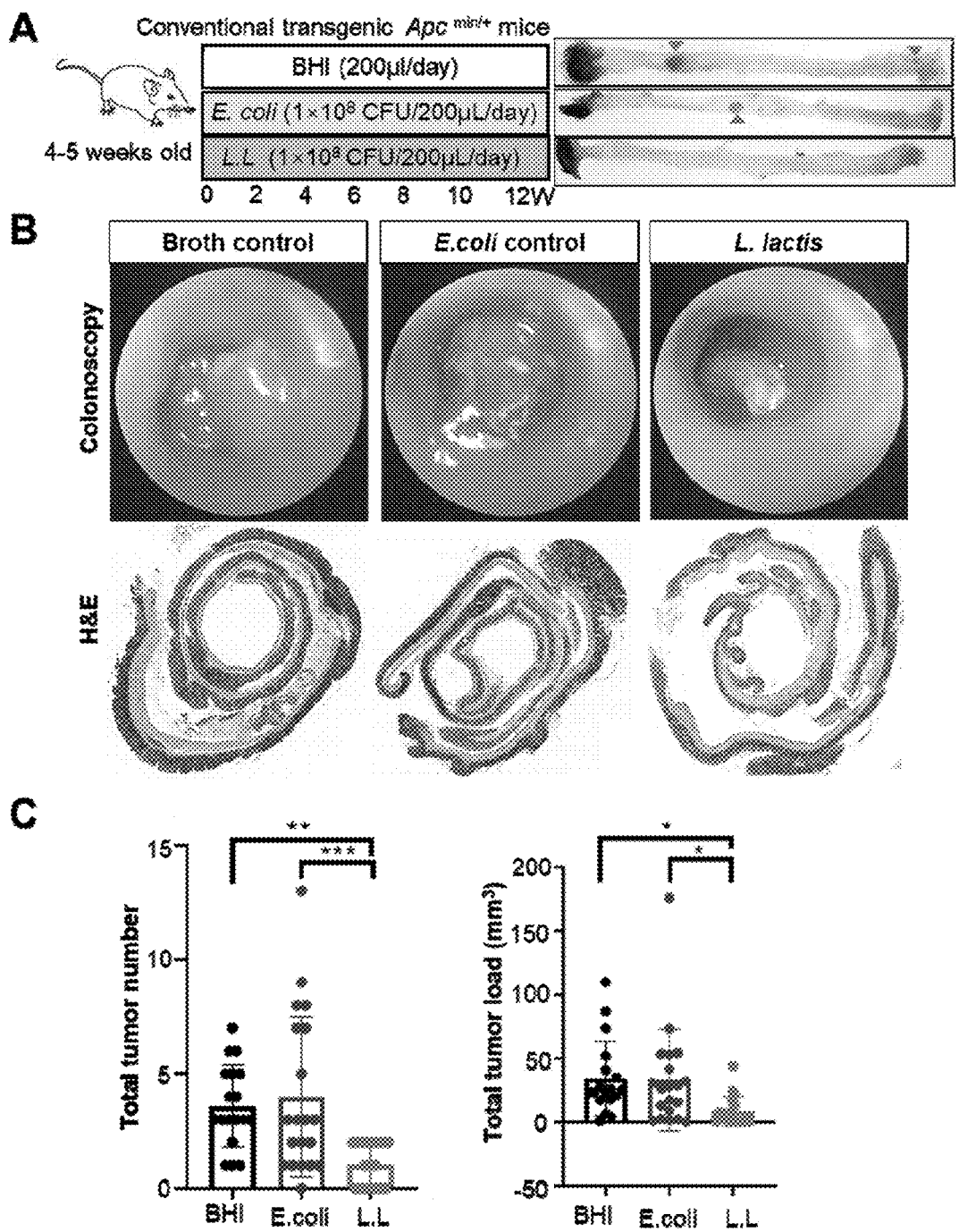
FIG. 21 shows that L. lactis protects against intestinal tumorigenesis in Apc$^{Min/+}$ mice. (A) Schematic diagram showing the experimental design, timeline, and representative colonic morphologies of Apc$^{min/+}$ mice under different treatments. (B) Representative images of colon tumor under colonoscopy (upper panels) and representative H&E-stained histological images (lower panels) from Apc$^{min/+}$ mice under different treatments. (C) Total tumor number and tumor load of Apc$^{min/+}$ mice under different treatments. Results are presented as mean±S.D. Statistical significance was determined by one-way ANOVA. L.L, L. lactis; W, week.

To investigate the potential protective effect of L. lactis on colorectal tumorigenesis 5-week-old $Apc^{Min/+}$ mice were orally gavaged with L. lactis ($1.0 \times 10^8$ CFUs per mouse) or E. coli strain MG1655 ($1.0 \times 10^8$ CFUs per mouse) for 12 weeks. BHI was used as the plain culture broth control (FIG. 21A). Colonoscopy was performed during the period of gavage to monitor the tumor formation (FIG. 21B, upper). The tumor histology was further examined (FIG. 21B, lower) and the obvious reduction of total tumor number and tumor size was observed in L. lactis-treated $Apc^{Min/+}$ mice (FIG. 21C). These results indicate that L. lactis abrogates intestinal tumorigenesis in $Apc^{Min/+}$ mice.

Figure 22:
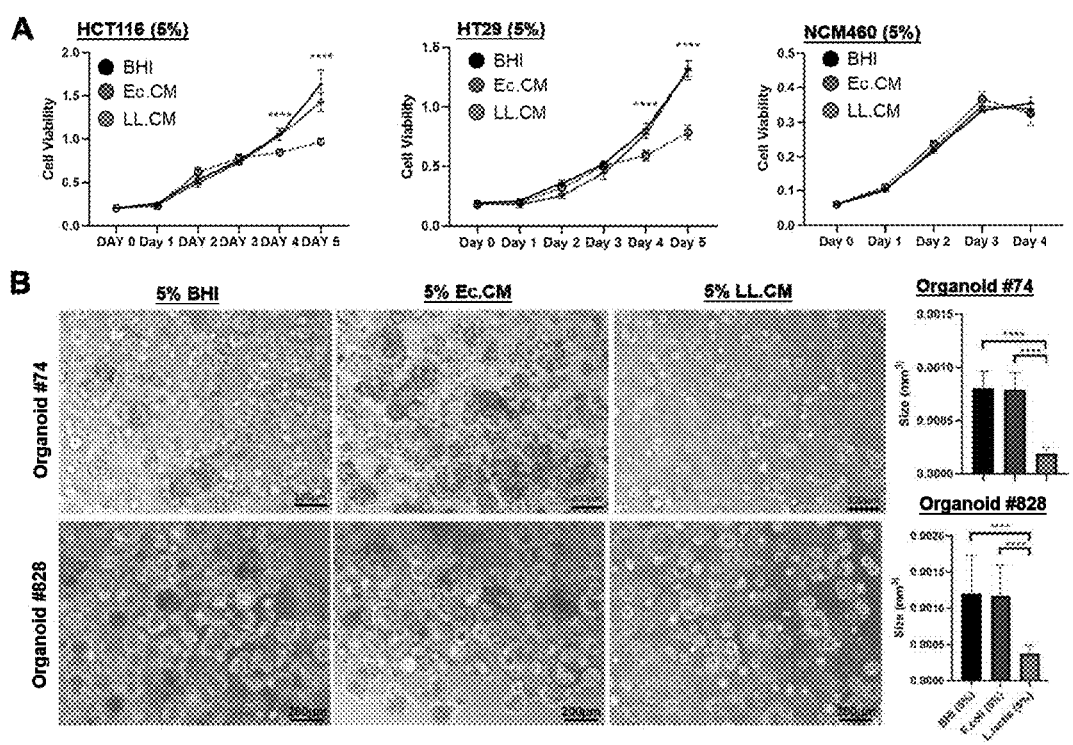
FIG. 22 shows that L. lactis conditioned medium (LL.CM) inhibits the viability of colon cancer cells. The proliferation of cells was measured by MTT assay. (A) LL.CM at 5% concentration significantly suppressed the CRC cells (HCT116 and HT29) growth but not the normal colonic epithelial cell line NCM460. (B) 5% LL.CM suppressed patient-derived organoids' size significantly. P-values are calculated by two-way ANOVA or one-way ANOVA where appropriate. *****p<0.0001. Ec.CM, E. coli conditioned medium; LL.CM, L. lactis conditioned medium.

L. lactis Conditioned Medium (LL.CM) Inhibits the Viability of Colon Cancer Cells To determine the tumor-suppressive effect of L. lactis in vitro, colon cancer cell lines (HCT116 and HT29) and a normal colonic epithelial cell line (NCM460) were co-cultured with or without LL.CM. As shown in FIG. 22A, co-culture with LL.CM significantly reduced the viability of CRC cell lines, but not in normal colonic epithelial cell line as determined by MTT assay. This inhibitory effect of LL.CM was further confirmed on CRC patient derived organoids. Consistent results were observed that LL.CM suppresses the organoids' size significantly as compared with BHI and Ec.CM (FIG. 22B). These data indicate that the secreted molecules from L. lactis, can suppress the viability of CRC cells in vitro.

Figure 23:
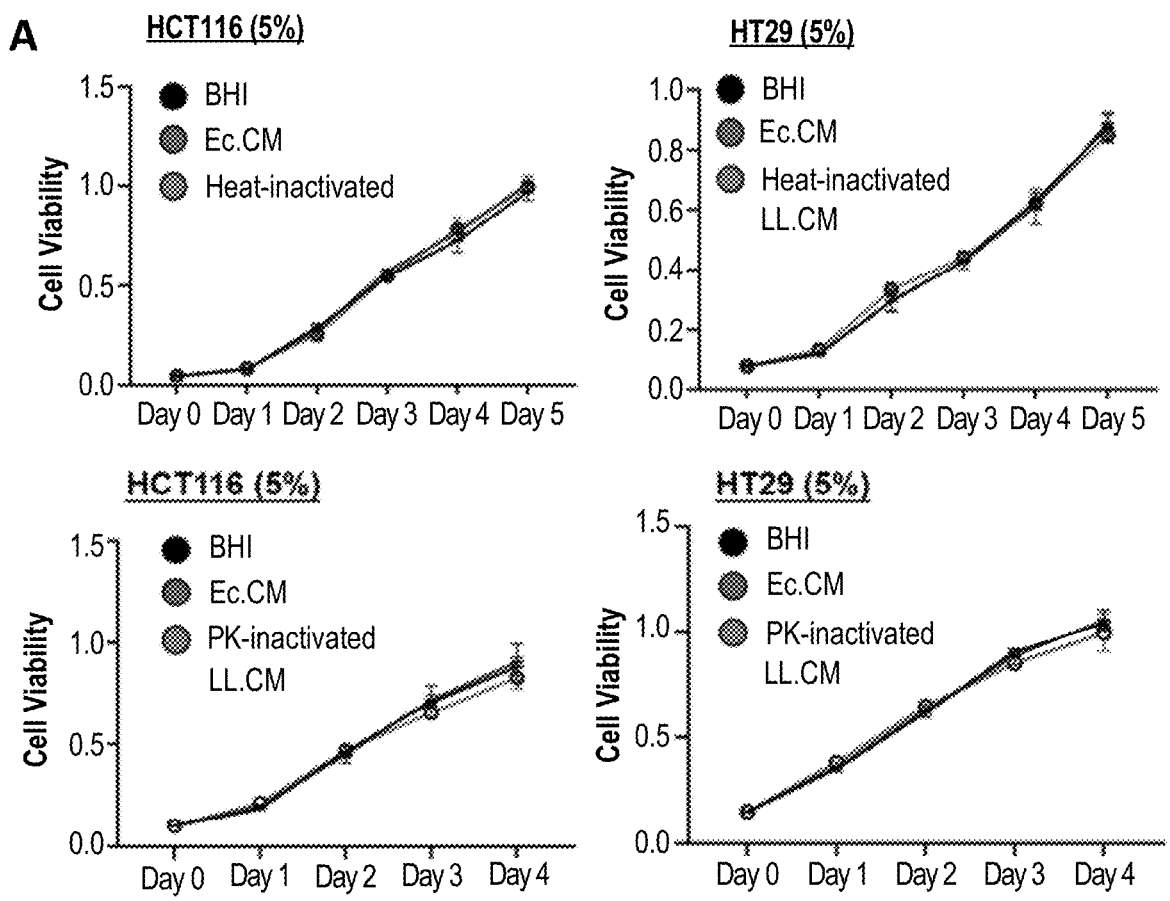
FIG. 23 shows that anti-tumor molecules produced from L. lactis are protein(s)>100 kDa in molecular weight. (A) Decrease in proliferation of CRC cells was not observed in heat- and PK-inactivated-LL.CM. (B) Decrease in colony formation of CRC cells was not observed in heat- and PK-inactivated-LL.CM. (C) Decrease in proliferation of CRC cells was only observed in LL.CM>100 kDa. P-values are calculated by two-way ANOVA or one-way ANOVA where appropriate. ****p<0.0001. Ec.CM, E. coli conditioned medium; LL.CM, L. lactis conditioned medium.; PK, proteinase K.
Figure 23:
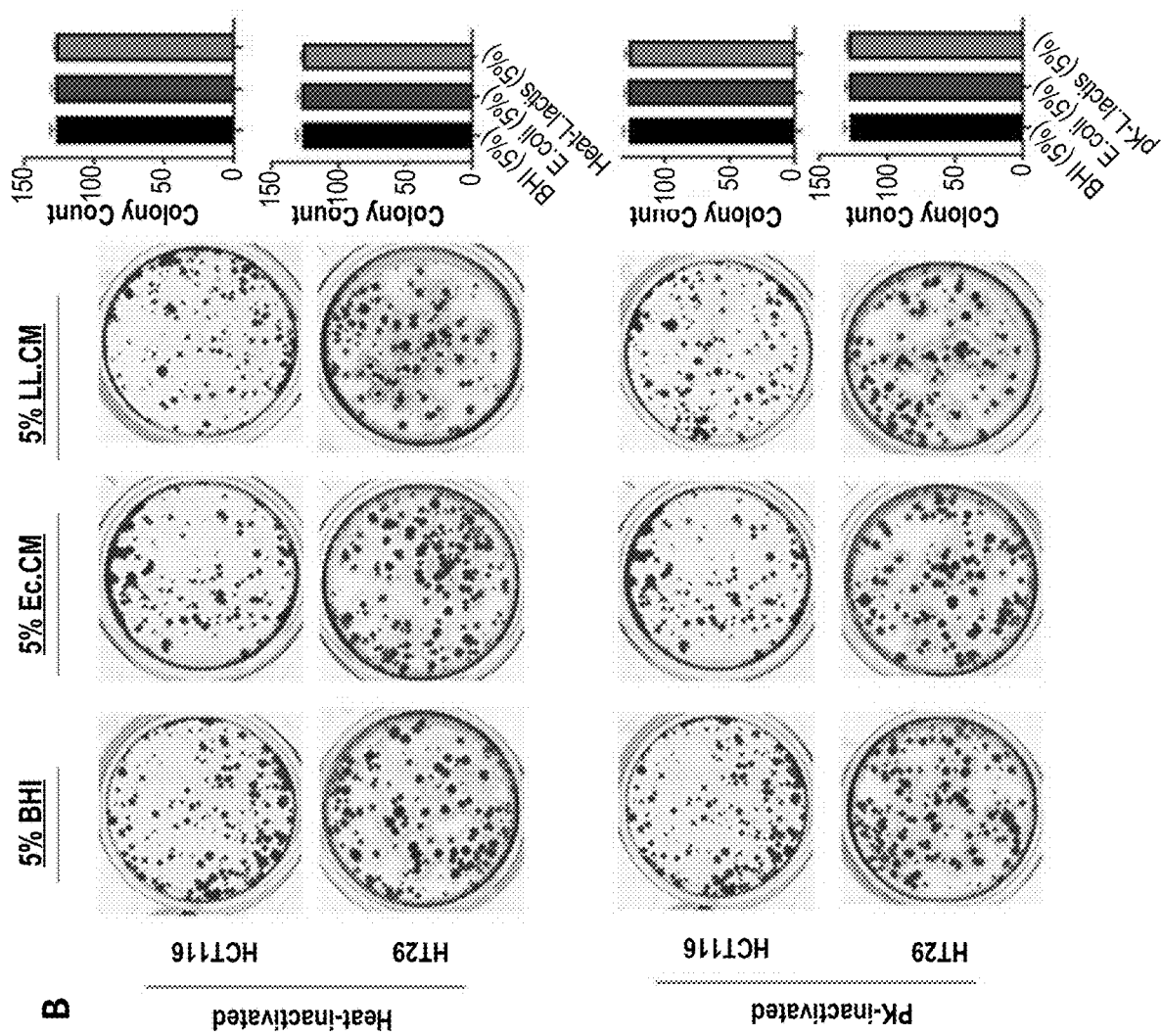

Anti-Tumor Molecules Produced from L. lactis are Protein(s) with a Molecular Weight>100 kDa To determine the characteristic of molecules produced from L. lactis responsible for anti-CRC activity, the LL.CM was inactivated by heating at 100° C. for 30 minutes, the inhibitory effect of LL.CM disappeared (FIG. 23A, upper). Consistently, digestion LL.CM by protease K (PK, 50 µg/mL) further neutralized the tumor-suppressive effect of LL.CM (FIG. 23A, lower), indicating the protein nature of the anti-tumor molecule(s) in the LL.CM. The colony formation was further performed to confirm the anti-tumor fraction separated from the LL.CM was protein (FIG. 23B). LL.CM was further separated into LMW 100 kDa) and HMW (>100 kDa) fractions using 100-kDa filter units. As shown in FIG. 23C, decrease in viability of CRC cells was observed only in those treated with LL.CM HMW fraction, while LL.CM LMW fraction had no suppressive effect on CRC cells. Collectively, these results indicate that the anti-CRC properties of L. lactis could be induced by one or more proteins with a molecular weight>100 kDa.

Anti-Tumor Molecules Produced from L. lactis Contains Aminopeptidase

Figure 24:
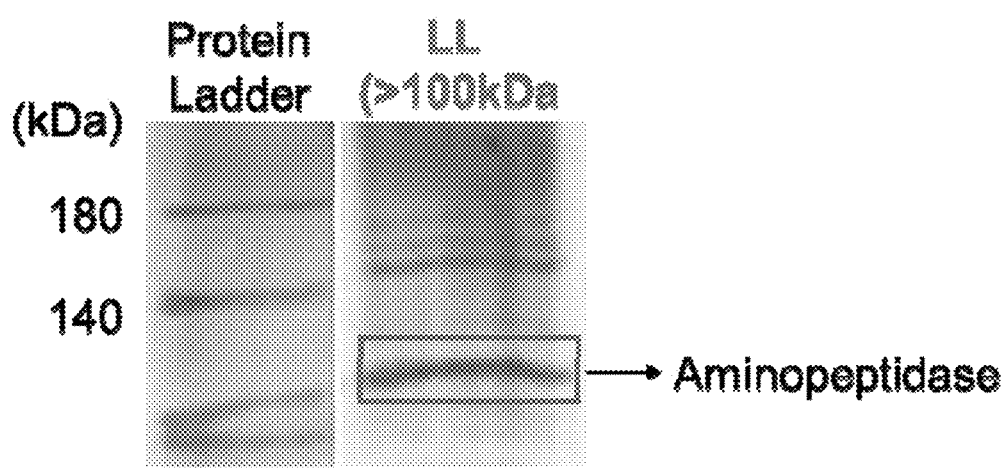
FIG. 24 shows that anti-tumor molecules produced from L. lactis contain aminopeptidase. L.L, L. lactis.

The potential functional secreted proteins were separated by 5% SDS-PAGE and in-gel digestion, which was then analyzed by mass spectrometry. The results show that aminopeptidase was enriched in the LL.CM>100 kDa faction (FIG. 24). These results indicate that the anti-tumor fraction secreted from L. lactis might be an aminopeptidase.

Discussion

In this study, oral administration of L. lactis was demonstrated to reduce intestinal tumor number and size in $Apc^{Min/+}$ mice. Further in vitro experiments revealed that a protein with molecular weight>100 kDa attributes to the tumor-suppressive effect, and this protein might be aminopeptidase. This healthy human isolated probiotic could be used as a potential prophylactic for preventing CRC in human with minimal side effects.

LIST OF REFERENCES

1. Coker O O, Wu W K K, Wong S H, Sung J J Y, Yu J. Altered Gut Archaea Composition and Interaction With Bacteria Are Associated With Colorectal Cancer. *Gastroenterology*. October 2020; 159(4):1459-1470 e1455.
2. Fong W, Li Q, Yu J. Gut microbiota modulation: a novel strategy for prevention and treatment of colorectal cancer. *Oncogene*. June 2020; 39(26):4925-4943.
3. Brennan C A, Garrett W S. Gut Microbiota, Inflammation, and Colorectal Cancer. *Annual review of microbiology*. Sep. 8, 2016; 70:395-411.
4. Sivan A, Corrales L, Hubert N, et al. Commensal *Bifidobacterium* promotes antitumor immunity and facilitates anti-PD-L1 efficacy. *Science*. Nov. 27, 2015; 350(6264):1084-1089.
5. Liu Q, Yu Z, Tian F, et al. Surface components and metabolites of probiotics for regulation of intestinal epithelial barrier. *Microbial cell factories*. Feb. 5, 2020; 19(1):23.
6. Li Q, Hu W, Liu W X, et al. *Streptococcus thermophilus* Inhibits Colorectal Tumorigenesis Through Secreting beta-Galactosidase. *Gastroenterology*. Sep. 11, 2020.
7. Nakatsu G, Li X, Zhou H, et al. Gut mucosal microbiome across stages of colorectal carcinogenesis. *Nature communications*. Oct. 30, 2015; 6:8727.
8. Ho J, Chan H, Liang Y, et al. Cathelicidin preserves intestinal barrier function in polymicrobial sepsis. *Critical care*. Feb. 10, 2020; 24(1):47.

9. Colaprico A, Silva T C, Olsen C, et al. TCGAbiolinks: an R/Bioconductor package for integrative analysis of TCGA data. *Nucleic acids research*. May 5, 2016; 44(8):e71.
10. Cancer Genome Atlas N. Comprehensive molecular characterization of human colon and rectal cancer. *Nature*. Jul. 18, 2012; 487(7407):330-337.
11. Walker M A, Pedamallu C S, Ojesina A I, et al. GATK PathSeq: a customizable computational tool for the discovery and identification of microbial sequences in libraries from eukaryotic hosts. *Bioinformatics*. Dec. 15, 2018; 34(24):4287-4289.
12. Zou Y, Xue W, Luo G, et al. 1,520 reference genomes from cultivated human gut bacteria enable functional microbiome analyses. *Nature biotechnology*. February 2019; 37(2):179-185.
13. Dai Z, Coker O O, Nakatsu G, et al. Multi-cohort analysis of colorectal cancer metagenome identified altered bacteria across populations and universal bacterial markers. *Microbiome*. Apr. 11, 2018; 6(1):70.
14. Deeb K K, Trump D L, Johnson C S. Vitamin D signalling pathways in cancer: potential for anticancer therapeutics. *Nature reviews. Cancer*. September 2007; 7(9):684-700.
15. Wagner D, Dias A G, Schnabl K, Van der Kwast T, Vieth R. Determination of 1,25-dihydroxyvitamin D concentrations in human colon tissues and matched serum samples. *Anticancer research*. January 2012; 32(1):259-263.
16. Liu X, Cheng Y, Shao L, Ling Z. Alterations of the Predominant Fecal Microbiota and Disruption of the Gut Mucosal Barrier in Patients with Early-Stage Colorectal Cancer. *BioMed research international*. 2020; 2020:2948282.
17. Ji J, Qu H, Shu D. Crosstalk Between Bioactive Peptide and Intestinal Barrier in Gut Homeostasis. *Current protein & peptide science*. 2015; 16(7):604-612.
18. Long X, Wong C C, Tong L, et al. *Peptostreptococcus anaerobius* promotes colorectal carcinogenesis and modulates tumour immunity. *Nature microbiology*. December 2019; 4(12):2319-2330.
19. Xia X, Wu W K K, Wong S H, et al. Bacteria pathogens drive host colonic epithelial cell promoter hypermethylation of tumor suppressor genes in colorectal cancer. *Microbiome*. Jul. 16, 2020; 8(1):108.
20. Thomaz F S, Altemani F, Panchal S K, Worrall S, Dekker Nitert M. The influence of wasabi on the gut microbiota of high-carbohydrate, high-fat diet-induced hypertensive Wistar rats. *Journal of human hypertension*. February 2021; 35(2):170-180.
21. Kim S J, Kim S E, Kim A R, Kang S, Park M Y, Sung M K. Dietary fat intake and age modulate the composition of the gut microbiota and colonic inflammation in C57BL/6J mice. *BMC microbiology*. Aug. 20, 2019; 19(1):193.
22. Santiago A, Sanchez E, Clark A, et al. Sequential Changes in the Mesenteric Lymph Node Microbiome and Immune Response during Cirrhosis Induction in Rats. *mSystems*. January-February 2019; 4(1).
23. Hofer U. Microbiome: pro-inflammatory *Prevotella*? *Nature reviews. Microbiology*. January 2014; 12(1):5.
24. Jia W, Rajani C, Xu H, Zheng X. Gut microbiota alterations are distinct for primary colorectal cancer and hepatocellular carcinoma. *Protein & cell*. Aug. 14, 2020.
25. Fan Y, Zhang J. Dietary Modulation of Intestinal Microbiota: Future Opportunities in Experimental Autoimmune Encephalomyelitis and Multiple Sclerosis. *Frontiers in microbiology*. 2019; 10:740.
26. Yuan C, Ng K. Vitamin D supplementation: a potential therapeutic agent for metastatic colorectal cancer. *British journal of cancer*. October 2020; 123(8):1205-1206.
27. Xu Y, Qian M, Hong J, et al. The effect of vitamin D on the occurrence and development of colorectal cancer: a systematic review and meta-analysis. *International journal of colorectal disease*. Feb. 17, 2021.
28. Vidigal V M, Silva T D, de Oliveira J, Pimenta C A M, Felipe A V, Forones N M. Genetic polymorphisms of vitamin D receptor (VDR), CYP27B1 and CYP24A1 genes and the risk of colorectal cancer. *The International journal of biological markers*. May 4, 2017; 32(2):e224-e230.
29. Shang M, Sun J. Vitamin D/VDR, Probiotics, and Gastrointestinal Diseases. *Current medicinal chemistry*. 2017; 24(9):876-887.
30. Stubbins R E, Hakeem A, Nunez N P. Using components of the vitamin D pathway to prevent and treat colon cancer. *Nutrition reviews*. December 2012; 70(12):721-729.
31. Sun J. Dietary vitamin D, vitamin D receptor, and microbiome. *Current opinion in clinical nutrition and metabolic care*. November 2018; 21(6):471-474.
32. Siegel R L, Miller K D, Jemal A. Cancer statistics, 2019. *CA: a cancer journal for clinicians*. January 2019; 69(1):7-34.
33. Rawla P, Sunkara T, Barsouk A. Epidemiology of colorectal cancer: incidence, mortality, survival, and risk factors. *Przeglad gastroenterologiczny*. 2019; 14(2):89-103.
34. Li Q, Hu W, Liu W X, et al. *Streptococcus thermophilus* Inhibits Colorectal Tumorigenesis Through Secreting beta-Galactosidase. *Gastroenterology*. Sep. 11, 2020.
35. Mao J, Qi S, Cui Y, et al. *Lactobacillus rhamnosus* GG Attenuates Lipopolysaccharide-Induced Inflammation and Barrier Dysfunction by Regulating MAPK/NF-kappaB Signaling and Modulating Metabolome in the Piglet Intestine. The Journal of nutrition. May 1, 2020; 150(5):1313-1323.
36. Lin R, Sun Y, Mu P, et al. *Lactobacillus rhamnosus* GG supplementation modulates the gut microbiota to promote butyrate production, protecting against deoxynivalenol exposure in nude mice. *Biochemical pharmacology*. May 2020; 175:113868.
37. Soltan Dallal M M, Mojarrad M, Baghbani F, Raoofian R, Mardaneh J, Salehipour Z. Effects of probiotic *Lactobacillus acidophilus* and *Lactobacillus casei* on colorectal tumor cells activity (CaCo-2). *Archives of Iranian medicine*. March 2015; 18(3):167-172.
38. Zhuo Q, Yu B, Zhou J, et al. Lysates of *Lactobacillus acidophilus* combined with CTLA-4-blocking antibodies enhance antitumor immunity in a mouse colon cancer model. *Scientific reports*. Dec. 27, 2019; 9(1):20128.
39. Salva S, Marranzino G, Villena J, Aguero G, Alvarez S. Probiotic *Lactobacillus* strains protect against myelosuppression and immunosuppression in cyclophosphamide-treated mice. *International immunopharmacology*. September 2014; 22(1):209-221.
40. Shin R, Itoh Y, Kataoka M, et al. Anti-tumor activity of heat-killed *Lactobacillus plantarum* BF-LP284 on Meth-A tumor cells in BALB/c mice. *International journal of food sciences and nutrition*. September 2016; 67(6):641-649.
41. Moser A R, Pitot H C, Dove W F. A dominant mutation that predisposes to multiple intestinal neoplasia in the mouse. *Science*. Jan. 19, 1990; 247(4940):322-324.
42. Sapi J, Kovacs L, Drexler D A, Kocsis P, Gajari D, Sapi Z. Tumor Volume Estimation and Quasi-Continuous Administration for Most Effective Bevacizumab Therapy. *PloS one*. 2015; 10(11):e0142190.
43. Schloss P D, Westcott S L, Ryabin T, et al. Introducing mothur: open-source, platform-independent, community-supported software for describing and comparing microbial communities. *Appl Environ Microbiol*. December 2009; 75(23):7537-7541.

44. Needleman S B, Wunsch C D. A general method applicable to the search for similarities in the amino acid sequence of two proteins. *J Mol Biol*. March 1970; 48(3):443-453.
45. Quast C, Pruesse E, Yilmaz P, et al. The SILVA ribosomal RNA gene database project: improved data processing and web-based tools. *Nucleic Acids Res*. January 2013; 41(Database issue):D590-596.
46. DeSantis T Z, Jr., Hugenholtz P, Keller K, et al. NAST: a multiple sequence alignment server for comparative analysis of 16S rRNA genes. *Nucleic Acids Res*. Jul. 1, 2006; 34(Web Server issue):W394-399.
47. Edgar R C, Haas B J, Clemente J C, Quince C, Knight R. UCHIME improves sensitivity and speed of chimera detection. Bioinformatics. Aug. 15, 2011; 27(16):2194-2200.
48. Dembele D, Kastner P. Fold change rank ordering statistics: a new method for detecting differentially expressed genes. *BMC Bioinformatics*. Jan. 15, 2014; 15:14.
49. Jin Y, Tang S, Li W, et al. Hemolytic *E. coli* Promotes Colonic Tumorigenesis in Females. *Cancer Res*. May 15, 2016; 76(10):2891-2900.
50. Roager H M, Licht T R. Microbial tryptophan catabolites in health and disease. *Nature communications*. Aug. 17, 2018; 9(1):3294.
51. Jan G, Belzacq A S, Haouzi D, et al. Propionibacteria induce apoptosis of colorectal carcinoma cells via short-chain fatty acids acting on mitochondria. *Cell Death Differ*. February 2002; 9(2):179-188.
52. Tiptiri-Kourpeti A, Spyridopoulou K, Santarmaki V, et al. *Lactobacillus casei* Exerts Anti-Proliferative Effects Accompanied by Apoptotic Cell Death and Up-Regulation of TRAIL in Colon Carcinoma Cells. *PLoS One*. 2016; 11(2):e0147960.
53. Saxami G, Karapetsas A, Chondrou P, et al. Potentially probiotic *Lactobacillus* strains with anti-proliferative activity induce cytokine/chemokine production and neutrophil recruitment in mice. *Benef Microbes*. Aug. 24, 2017; 8(4):615-623.
54. Elfahri K R, Vasiljevic T, Yeager T, Donkor O N. Anti-colon cancer and antioxidant activities of bovine skim milk fermented by selected *Lactobacillus helveticus* strains. *Journal of dairy science*. January 2016; 99(1):31-40.
55. El-Deeb N M, Yassin A M, Al-Madboly L A, El-Hawiet A. A novel purified *Lactobacillus acidophilus* 20079 exopolysaccharide, LA-EPS-20079, molecularly regulates both apoptotic and NF-kappaB inflammatory pathways in human colon cancer. *Microb Cell Fact*. Feb. 21, 2018; 17(1):29.
56. Agah S, Alizadeh A M, Mosavi M, et al. More Protection of *Lactobacillus acidophilus* Than *Bifidobacterium bifidum* Probiotics on Azoxymethane-Induced Mouse Colon Cancer. *Probiotics Antimicrob Proteins*. September 2019; 11(3):857-864.
57. Orlando A, Refolo M G, Messa C, et al. Antiproliferative and proapoptotic effects of viable or heat-killed *Lactobacillus paracasei* IMPC2.1 and *Lactobacillus rhamnosus* GG in HGC-27 gastric and DLD-1 colon cell lines. *Nutr Cancer*. 2012; 64(7):1103-1111.
58. Gamallat Y, Meyiah A, Kuugbee E D, et al. *Lactobacillus rhamnosus* induced epithelial cell apoptosis, ameliorates inflammation and prevents colon cancer development in an animal model. *Biomed Pharmacother*. October 2016; 83:536-541.
59. Hatakka K, Holma R, El-Nezami H, et al. The influence of *Lactobacillus rhamnosus* LC705 together with *Propionibacterium freudenreichii* ssp. *shermanii* JS on potentially carcinogenic bacterial activity in human colon. *Int J Food Microbiol*. Dec. 10, 2008; 128(2):406-410.
60. Ohara T, Yoshino K, Kitajima M. Possibility of preventing colorectal carcinogenesis with probiotics. *Hepatogastroenterology*. November-December 2010; 57(104):1411-1415.
61. Liu Z, Qin H, Yang Z, et al. Randomised clinical trial: the effects of perioperative probiotic treatment on barrier function and post-operative infectious complications in colorectal cancer surgery—a double-blind study. *Aliment Pharmacol Ther*. January 2011; 33(1):50-63.
62. Jeon H J, Yeom Y, Kim Y S, et al. Effect of vitamin C on azoxymethane (AOM)/dextran sulfate sodium (DSS)-induced colitis-associated early colon cancer in mice. *Nutrition research and practice*. April 2018; 12(2):101-109.
63. Koh G Y, Kane A V, Wu X, Crott J W. *Parabacteroides distasonis* attenuates tumorigenesis, modulates inflammatory markers and promotes intestinal barrier integrity in azoxymethane-treated A/J mice. *Carcinogenesis*. Jul. 14, 2020; 41(7):909-917.
64. Song H, Wang W, Shen B, et al. Pretreatment with probiotic Bifico ameliorates colitis-associated cancer in mice: Transcriptome and gut flora profiling. *Cancer science*. March 2018; 109(3):666-677.
65. Gao C, Ganesh B P, Shi Z, et al. Gut Microbe-Mediated Suppression of Inflammation-Associated Colon Carcinogenesis by Luminal Histamine Production. *The American journal of pathology*. October 2017; 187(10):2323-2336.
66. Wong S H, Zhao L, Zhang X, et al. Gavage of Fecal Samples From Patients With Colorectal Cancer Promotes Intestinal Carcinogenesis in Germ-Free and Conventional Mice. *Gastroenterology*. December 2017; 153(6):1621-1633 e1626.
67. Zackular J P, Baxter N T, Iverson K D, et al. The gut microbiome modulates colon tumorigenesis. *mBio*. Nov. 5, 2013; 4(6):e00692-00613.
68. Zhang M, Fan X, Fang B, Zhu C, Zhu J, Ren F. Effects of *Lactobacillus salivarius* Ren on cancer prevention and intestinal microbiota in 1, 2-dimethylhydrazine-induced rat model. *J Microbiol*. June 2015; 53(6):398-405.
69. Zhu J, Zhu C, Ge S, et al. *Lactobacillus salivarius* Ren prevent the early colorectal carcinogenesis in 1, 2-dimethylhydrazine-induced rat model. *J Appl Microbiol*. July 2014; 117(1):208-216.
70. Meng D, Sommella E, Salviati E, et al. Indole-3-lactic acid, a metabolite of tryptophan, secreted by *Bifidobacterium longum* subspecies *infantis* is anti-inflammatory in the immature intestine. *Pediatric research*. August 2020; 88(2):209-217.
71. Ou J, Carbonero F, Zoetendal E G, et al. Diet, microbiota, and microbial metabolites in colon cancer risk in rural Africans and African Americans. *Am J Clin Nutr*. July 2013; 98(1):111-120.
72. Lupton J R. Microbial degradation products influence colon cancer risk: the butyrate controversy. *J Nutr*. February 2004; 134(2):479-482.
73. Putaala H, Makivuokko H, Tiihonen K, Rautonen N. Simulated colon fiber metabolome regulates genes involved in cell cycle, apoptosis, and energy metabolism in human colon cancer cells. *Mol Cell Biochem*. November 2011; 357(1-2):235-245.
74. Chuah L O, Foo H L, Loh T C, et al. Postbiotic metabolites produced by *Lactobacillus plantarum* strains exert selective cytotoxicity effects on cancer cells. *BMC complementary and alternative medicine*. Jun. 3, 2019; 19(1):114.
75. Konishi H, Fujiya M, Tanaka H, et al. Probiotic-derived ferrichrome inhibits colon cancer progression via JNK-mediated apoptosis. *Nature communications*. Aug. 10, 2016; 7:12365.

All patents, patent applications, and other publications, including GenBank Accession Numbers and equivalents, cited in this application are incorporated by reference in the entirety for all purposes.

What is claimed is:

1. A method for treating or reducing risk of colorectal cancer in a subject, comprising administering to the subject an effective amount of *Lactobacillus gallinarum, Lactococcus lactis*, and *Carnobacterium maltaromaticum*.

2. The method of claim 1, wherein the subject is administered a composition comprising (1) an effective amount of *Lactobacillus gallinarum, Lactococcus lactis*, and *Carnobacterium maltaromaticum*; and (2) a physiologically acceptable excipient.

3. The method of claim 1, further comprising administering to the subject an effective amount of indole-3-lactic acid (ILA) or an aminopeptidase produced by *L. lactis* having a molecular weight greater than 100 kDa.

4. The method of claim 3, wherein the administering step comprises administering to the subject a first composition comprising an effective amount of (i) *L. gallinarum* or *L. lactis*; (ii) *L. gallinarum* or *L. lactis* culture supernatant; (iii) ILA; or (iv) an aminopeptidase produced by *L. lactis* with a molecular weight of greater than 100 kDa, and administering to the subject a second composition comprising an effective amount of *C. maltaromaticum*.

5. The method of claim 1, wherein the CFU ratio of *L. gallinarum* or *L. lactis* to *C. maltaromaticum* ranges from about 1:5 to about 5:1.

6. The method of claim 1, wherein the administering step comprises oral administration.

7. The method of claim 1, wherein the subject is not diagnosed with colitis.

8. The method of claim 2, wherein the composition is in the form of a food or beverage item, or a food or beverage additive.

9. The method of claim 2, wherein the composition is in the form of a powder, liquid, paste, cream, tablet, capsule, or caplet.

10. The method of claim 2, wherein *L. gallinarum* or *L. lactis* is present in the range of about $1 \times 10^8$ to about $1 \times 10^{12}$ CFU per gram weight of the composition.

11. The method of claim 2, wherein *C. maltaromaticum* is present in the range of about $1 \times 10^8$ to about $1 \times 10^{12}$ CFU per gram weight of the composition.

12. The method of claim 2, wherein in the composition the CFU ratio of *L. gallinarum* or *L. lactis* to *C. maltaromaticum* ranges from about 1:5 to about 5:1.

13. The method of claim 2, wherein the composition is formulated in a daily dosage.

* * * * *